United States Patent
Garbers et al.

(10) Patent No.: US 12,241,075 B2
(45) Date of Patent: Mar. 4, 2025

(54) INSECT RESISTANT GENES AND METHODS OF USE

(71) Applicant: BASF Agricultural Solutions Seed US LLC, Florham Park, NJ (US)

(72) Inventors: Amanda Marie Garbers, Westfield, IN (US); Duane Lehtinen, Cary, NC (US); Nanasaheb Chougule, Apex, NC (US); Aaron Beyerlein, Carrboro, NC (US); Jelena Zaitseva, Cary, NC (US); Timothy Eberle, Cary, NC (US); Lei Ding, Cary, NC (US)

(73) Assignee: BASF Agricultural Solutions US LLC, Research Triangle Park, NC (US)

( * ) Notice: Subject to any disclaimer, the term of this patent is extended or adjusted under 35 U.S.C. 154(b) by 75 days.

(21) Appl. No.: 17/768,157

(22) PCT Filed: Oct. 12, 2020

(86) PCT No.: PCT/US2020/055258
§ 371 (c)(1),
(2) Date: Apr. 11, 2022

(87) PCT Pub. No.: WO2021/076452
PCT Pub. Date: Apr. 22, 2021

(65) Prior Publication Data
US 2023/0183735 A1 Jun. 15, 2023

Related U.S. Application Data

(60) Provisional application No. 62/914,765, filed on Oct. 14, 2019.

(51) Int. Cl.
| | |
|---|---|
| *C12N 15/82* | (2006.01) |
| *A01N 63/23* | (2020.01) |
| *A01P 7/04* | (2006.01) |
| *C07K 14/325* | (2006.01) |
| *C12N 15/75* | (2006.01) |

(52) U.S. Cl.
CPC ......... *C12N 15/8286* (2013.01); *A01N 63/23* (2020.01); *A01P 7/04* (2021.08); *C07K 14/325* (2013.01); *C12N 15/75* (2013.01)

(58) Field of Classification Search
None
See application file for complete search history.

(56) References Cited

U.S. PATENT DOCUMENTS

| | | | |
|---|---|---|---|
| 8,829,279 | B2 | 9/2014 | Carozzi et al. |
| 2006/0156432 | A1 | 7/2006 | Arnaut et al. |
| 2011/0030096 | A1 | 2/2011 | Sampson et al. |
| 2011/0203015 | A1* | 8/2011 | Sampson ............... A01N 63/50 435/468 |
| 2011/0263488 | A1 | 10/2011 | Carozzi et al. |
| 2016/0311865 | A1* | 10/2016 | Lehtinen .............. C07K 14/325 |
| 2018/0371032 | A1 | 12/2018 | Lehtinen et al. |

FOREIGN PATENT DOCUMENTS

WO  WO-2013/134734 A2  9/2013

OTHER PUBLICATIONS

International Search Report for PCT Patent Application No. PCT/US2020/055258, Issued on Feb. 2, 2021, 6 pages.
Written Opinion of the International Searching Authority for PCT Patent Application No. PCT/US2020/055258, Issued on Feb. 2, 2021, 8 pages.
International Preliminary Report on Patentability for PCT Patent Application No. PCT/US2020/055258, Issued on Apr. 19, 2022, 9 pages.

* cited by examiner

*Primary Examiner* — Amjad Abraham
*Assistant Examiner* — Kelsey L McWilliams
(74) *Attorney, Agent, or Firm* — BASF Corporation; Barbara Campbell

(57) ABSTRACT

Compositions and methods for conferring pesticidal activity to bacteria, plants, plant cells, tissues and seeds are provided. Compositions comprising a coding sequence for a toxin polypeptide are provided. The coding sequences can be used in DNA constructs or expression cassettes for transformation and expression in plants and bacteria. Compositions also comprise transformed bacteria, plants, plant cells, tissues, and seeds. In particular, isolated toxin nucleic acid molecules are provided. Additionally, amino acid sequences corresponding to the polynucleotides are encompassed, and antibodies specifically binding to those amino acid sequences. In particular, the present invention provides for isolated nucleic acid molecules comprising nucleotide sequences encoding the amino acid sequence shown in any of SEQ ID NO: 16 to 30, or the nucleotide sequence set forth in any of SEQ ID NO: 1 to 15, as well as variants and fragments thereof.

22 Claims, 12 Drawing Sheets

Specification includes a Sequence Listing.

INSECT RESISTANT GENES AND METHODS OF USE

RELATED APPLICATIONS

This application is a national stage application under 35 U.S.C. § 371 of PCT/US2020/055258, filed Oct. 12, 2020, which claims benefit of U.S. provisional application No. 62/914,765, filed Oct. 14, 2019.

SUBMISSION OF SEQUENCE LISTING

The Sequence Listing associated with this application is filed in electronic format via EFS-Web and hereby incorporated by reference into the specification in its entirety. The name of the text file containing the Sequence Listing is 1 90770US02 Sequence_Listing.txt. The size of the text file is 70 KB, and the text file was created on Apr. 6, 2022.

FIELD OF THE INVENTION

This invention relates to the field of molecular biology. Provided are novel genes that encode pesticidal proteins. These proteins and the nucleic acid sequences that encode them are useful in preparing pesticidal formulations and in the production of transgenic pest-resistant plants.

BACKGROUND OF THE INVENTION

Plant pests are a major factor in the loss of the world's important agricultural crops. About $8 billion are lost every year in the U.S. alone due to infestations of non-mammalian pests including insects. Insect pests are mainly controlled by intensive applications of chemical pesticides, which are active through inhibition of insect growth, prevention of insect feeding or reproduction, or cause death. Good insect control can thus be reached, but these chemicals can sometimes also affect other, beneficial insects. Another problem resulting from the wide use of chemical pesticides is the appearance of resistant insect varieties. This has been partially alleviated by various resistance management practices, but there is an increasing need for alternative pest control agents. Biological pest control agents, such as *Bacillus thuringiensis* strains expressing pesticidal toxins like δ-endotoxins, have also been applied to crop plants with satisfactory results, offering an alternative or complement to chemical pesticides. In particular, the expression of insecticidal toxins in transgenic plants, such as *B. thuringiensis* δ-endotoxins, has provided efficient protection against selected insect pests, and transgenic plants expressing such toxins have been commercialized, allowing farmers to reduce applications of chemical insect control agents.

*Bacillus thuringiensis* is a Gram-positive spore forming soil bacterium characterized by its ability to produce crystalline inclusions that are specifically toxic to certain orders and species of insects, but are harmless to plants and other non-targeted organisms. For this reason, compositions including *Bacillus thuringiensis* strains or their insecticidal proteins can be used as environmentally-acceptable insecticides to control agricultural insect pests or insect vectors for a variety of human or animal diseases.

Crystal (Cry) proteins (delta-endotoxins) from *Bacillus thuringiensis* have potent insecticidal activity against predominantly Lepidopteran, Hemipteran, Dipteran, and Coleopteran larvae. These proteins also have shown activity against Hymenoptera, Homoptera, Phthiraptera, Mallophaga, and Acari pest orders, as well as other invertebrate orders such as Nemathelminthes, Platyhelminthes, and Sarcomastigorphora (Feitelson (1993) The *Bacillus thuringiensis* family tree. In *Advanced Engineered Pesticides*, Marcel Dekker, Inc., New York, N.Y.) These proteins were originally classified as CryI to CryV based primarily on their insecticidal activity. The major classes were Lepidoptera-specific (I), Lepidoptera- and Diptera-specific (II), Coleoptera-specific (III), Diptera-specific (IV), and nematode-specific (V) and (VI). The proteins were further classified into subfamilies; more highly related proteins within each family were assigned divisional letters such as Cry1A, Cry1B, Cry1C, etc. Even more closely related proteins within each division were given names such as Cry1C1, Cry1C2, etc.

A nomenclature was described for the Cry genes based upon amino acid sequence homology rather than insect target specificity (Crickmore et al. (1998) *Microbiol. Mol. Biol. Rev.* 62:807-813). In this classification, each toxin is assigned a unique name incorporating a primary rank (an Arabic number), a secondary rank (an uppercase letter), a tertiary rank (a lowercase letter), and a quaternary rank (another Arabic number). Roman numerals have been exchanged for Arabic numerals in the primary rank. Proteins with less than 45% sequence identity have different primary ranks, and the criteria for secondary and tertiary ranks are 78% and 95%, respectively.

The crystal protein does not exhibit insecticidal activity until it has been ingested and solubilized in the insect midgut. The ingested protoxin is hydrolyzed by proteases in the insect digestive tract to an active toxic molecule. (Höfte and Whiteley (1989) *Microbiol. Rev.* 53:242-255). This toxin binds to apical brush border receptors in the midgut of the target larvae and inserts into the apical membrane creating ion channels or pores, resulting in larval death.

Delta-endotoxins generally have five conserved sequence domains, and three conserved structural domains (see, for example, de Maagd et al. (2001) *Trends Genetics* 17:193-199). The first conserved structural domain consists of seven alpha helices and is involved in membrane insertion and pore formation. Domain II consists of three beta-sheets arranged in a Greek key configuration, and domain III consists of two antiparallel beta-sheets in "jelly-roll" formation (de Maagd et al., 2001, supra). Domains II and III are involved in receptor recognition and binding, and are therefore considered determinants of toxin specificity.

Aside from delta-endotoxins, there are several other known classes of pesticidal protein toxins. The VIP1/VIP2 toxins (see, for example, U.S. Pat. No. 5,770,696) are binary pesticidal toxins that exhibit strong activity on insects by a mechanism believed to involve receptor-mediated endocytosis followed by cellular toxification, similar to the mode of action of other binary ("A/B") toxins. A/B toxins such as VIP, C2, CDT, CST, or the *B. anthracis* edema and lethal toxins initially interact with target cells via a specific, receptor-mediated binding of "B" components as monomers. These monomers then form homoheptamers. The "B" heptamer-receptor complex then acts as a docking platform that subsequently binds and allows the translocation of an enzymatic "A" component(s) into the cytosol via receptor-mediated endocytosis. Once inside the cell's cytosol, "A" components inhibit normal cell function by, for example, ADP-ribosylation of G-actin, or increasing intracellular levels of cyclic AMP (cAMP). See Barth et al. (2004) *Microbiol Mol Biol Rev* 68:373-402.

The intensive use of *B. thuringiensis*-based insecticides has already given rise to resistance in field populations of the diamondback moth, *Plutella xylostella* (Ferre and Van Rie (2002) *Annu. Rev. Entomol.* 47:501-533). The most common mechanism of resistance is the reduction of binding of the toxin to its specific midgut receptor(s). This may also confer cross-resistance to other toxins that share the same receptor (Ferre and Van Rie (2002)).

A further challenge is the fact that in some cases modifications to pesticidal protein domains might allow for improved control of one pest but at the same time diminish or reduce resistance to another pest that was previously controlled by the unmodified protein. Therefore, it is critical to not only consider new pesticidal activity derived from gene modifications but also ensure that the protein maintains resistance to other pest(s) that it was previously active against prior to the gene modifications.

Because of the devastation that insects can confer, and the improvement in yield by controlling a variety of insect pests, there is a continual need to discover new forms of pesticidal toxins.

SUMMARY OF INVENTION

Compositions and methods for conferring pesticidal activity to bacteria, plants, plant cells, tissues and seeds are provided. Compositions include nucleic acid molecules encoding sequences for pesticidal and insecticidal polypeptides, vectors comprising those nucleic acid molecules, and host cells comprising the vectors. Compositions also include the pesticidal polypeptide sequences and antibodies to those polypeptides. The nucleotide sequences can be used in DNA constructs or expression cassettes for transformation and expression in organisms, including microorganisms and plants. The nucleotide or amino acid sequences may be synthetic sequences that have been designed for expression in an organism including, but not limited to, a microorganism or a plant. Compositions also comprise bacteria, plants, plant cells, tissues, and seeds comprising the nucleotide sequence of the invention.

In particular, isolated, recombinant and chimeric nucleic acid molecules are provided that encode pesticidal proteins that are variations of Axmi486 as disclosed in U.S. Patent Application Publication US 2016 0311865 (herein, incorporated by reference in its entirety). Surprisingly, these variations increased resistance to *Spodoptera* species while at the same time maintaining resistance to *Plutella xylostella, Anticarsia, gemmatalis, Diatraea grandiosella, Diatraea saccharalis, Heliothis virescens, Helicoverpa zea,* and *Pseudoplusia includens.* Additionally, amino acid sequences corresponding to the pesticidal protein are encompassed. In particular, the present invention provides for an isolated, recombinant or chimeric nucleic acid molecule comprising a nucleotide sequence encoding the amino acid sequence shown in any of SEQ ID NO:16-30 or a nucleotide sequence set forth in SEQ ID NO:1-15, as well as biologically-active variants and fragments thereof. Nucleotide sequences that are complementary to a nucleotide sequence of the invention, or that hybridize to a sequence of the invention or a complement thereof are also encompassed. Further provided are vectors, host cells, plants, and seeds comprising the nucleotide sequences of the invention, or nucleotide sequences encoding the amino acid sequences of the invention, as well as biologically-active variants and fragments thereof.

Methods are provided for producing the polypeptides of the invention, and for using those polypeptides for controlling or killing a lepidopteran, hemipteran, coleopteran, nematode, or dipteran pest. Methods and kits for detecting the nucleic acids and polypeptides of the invention in a sample are also included.

The compositions and methods of the invention are useful for the production of organisms with enhanced pest resistance or tolerance. These organisms and compositions comprising the organisms are desirable for agricultural purposes. The compositions of the invention are also useful for generating altered or improved proteins that have pesticidal activity, or for detecting the presence of pesticidal proteins or nucleic acids in products or organisms.

BRIEF DESCRIPTION OF THE DRAWINGS

Each Figure contains a legend to the far right describing the samples being tested from top to bottom. The top variant is, in all cases, the wildtype control Axmi486 (indicated as "WT") followed by the experimental variants being compared to the WT. Each Figure also shows four series of dilutions indicated on the X axis. The data bars/columns for each series follow the legend from top to bottom. For example, for FIG. 1A the 1X series is interpreted as the following in the "1X" series: first column WT, second column R60S, third column R60T and fourth column E275D (as indicated top to bottom in legend). This same order proceeds for series "I0X", "30X", and "SOX" for FIG. 1A. All other Figures follow this same structure.

DETAILED DESCRIPTION

Figure 1A:
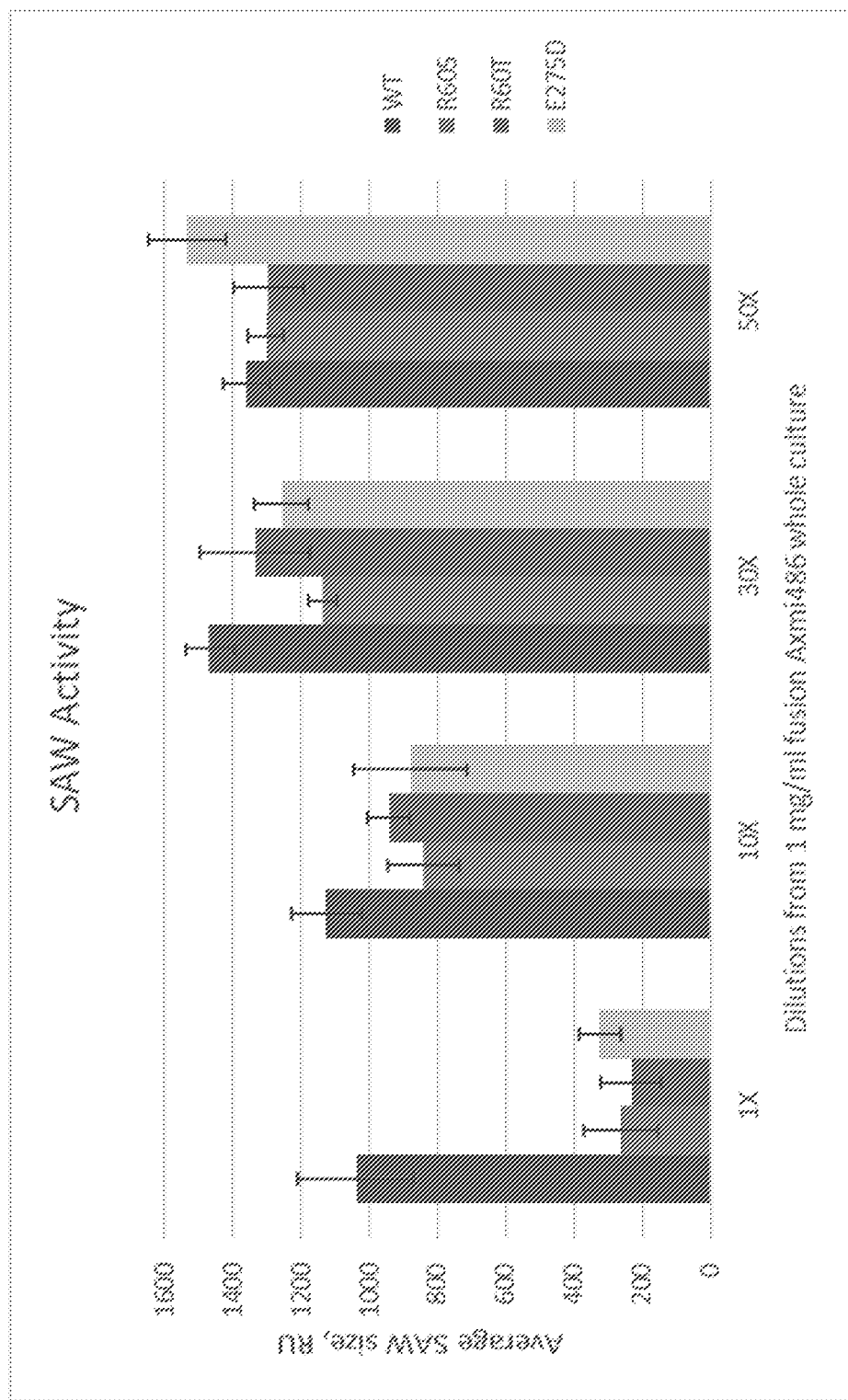
FIG. 1A—Axmi486 variant (respectively, R60S, R60T, and E275D) dosage experiments and effects on Southern armyworm growth rates as compared to controls treated with wildtype Axmi486 (WT)
Figure 1B:
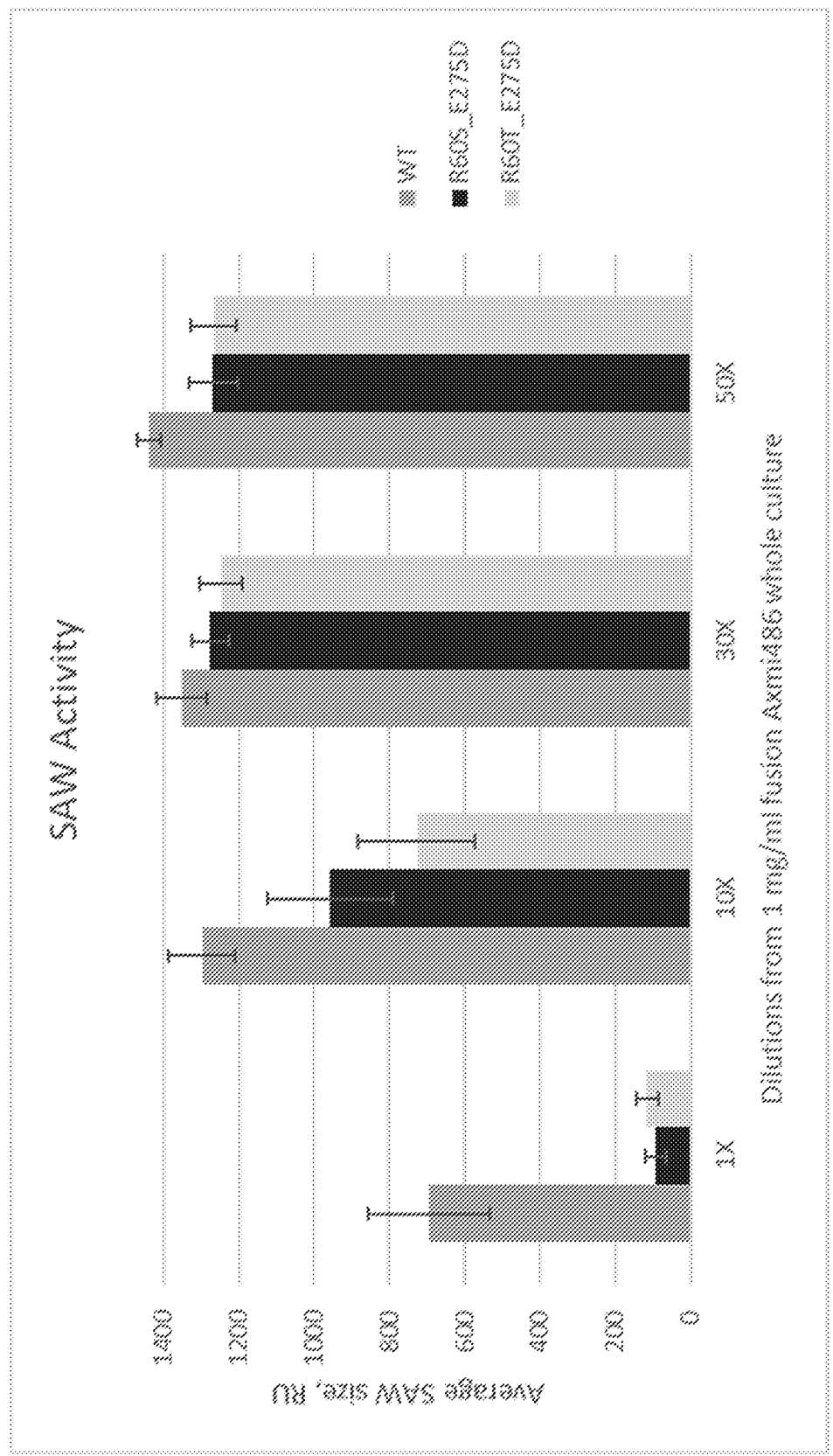
FIG. 1B—Axmi486 variant (respectively, R60S+E275D and R60T+E275D) dosage experiments and effects on Southern armyworm growth rates as compared to controls treated with wildtype Axmi486 (WT)
Figure 1C:
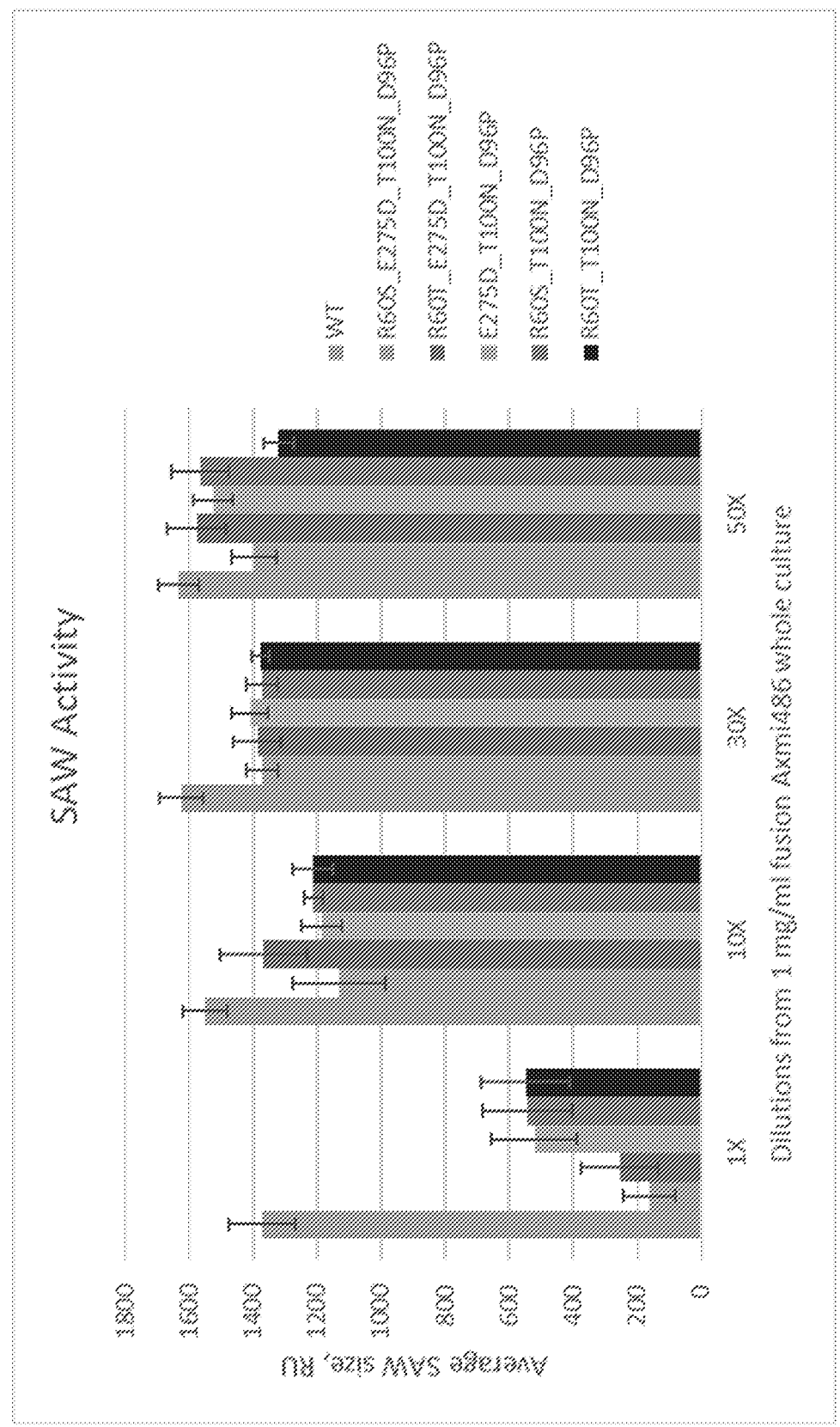
FIG. 1C—Axmi486 variant (respectively, R60S+E275D+TI00N+D96P; R60T+E275D+TI00N+D96P; E275D+TI00N+D96P; R60T+TI00N+D96P) dosage experiments and effects on Southern armyworm growth rates as compared to controls treated with wildtype Axmi486 (WT)
Figure 1D:
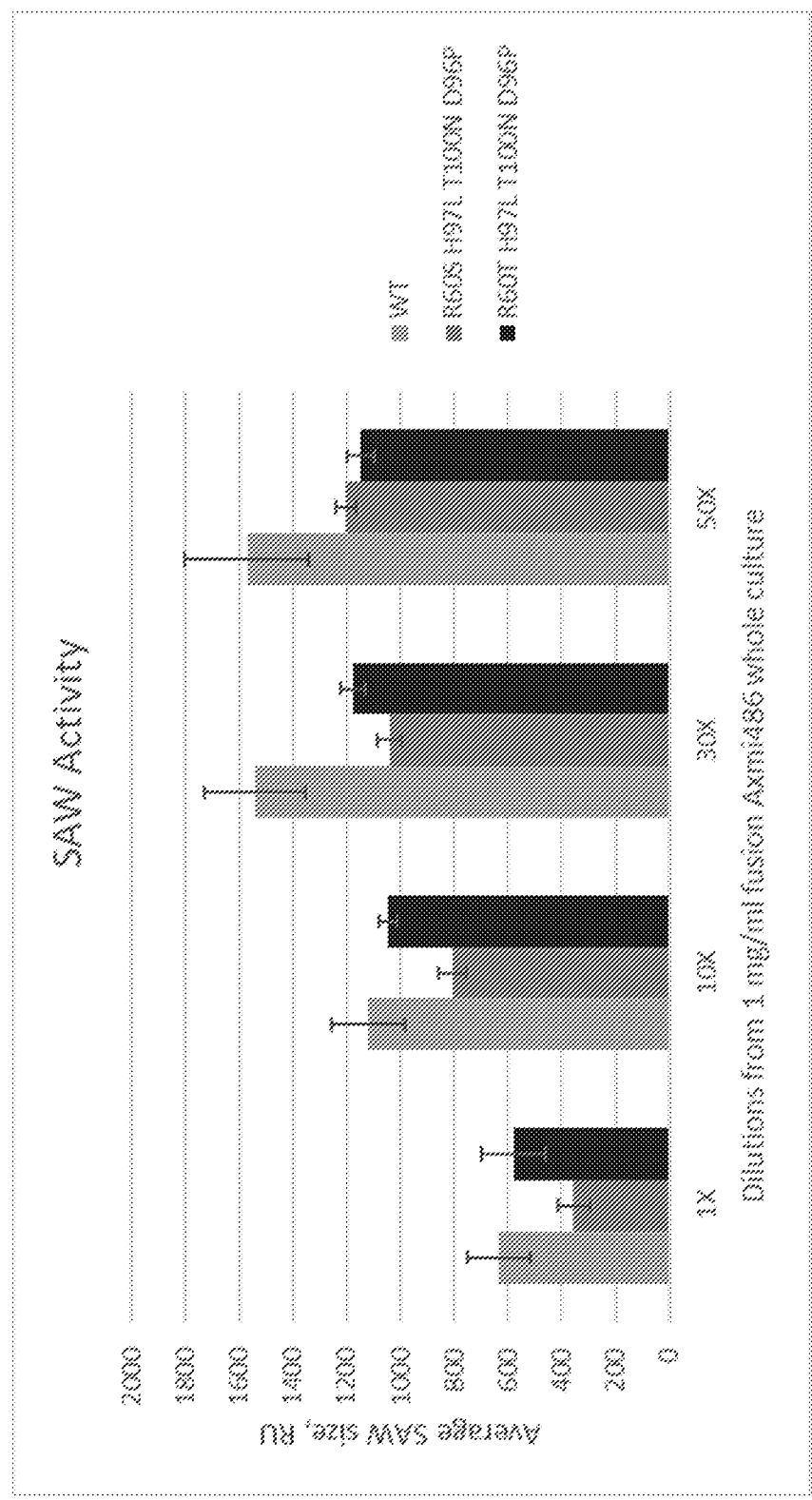
FIG. 1D—Axmi486 variant (respectively, R60S+H97L+TI00N+D96P; R60T+H97L+TI00N+D96P) dosage experiments and effects on Southern armyworm growth rates as compared to controls treated with wildtype Axmi486 (WT)
Figure 1E:
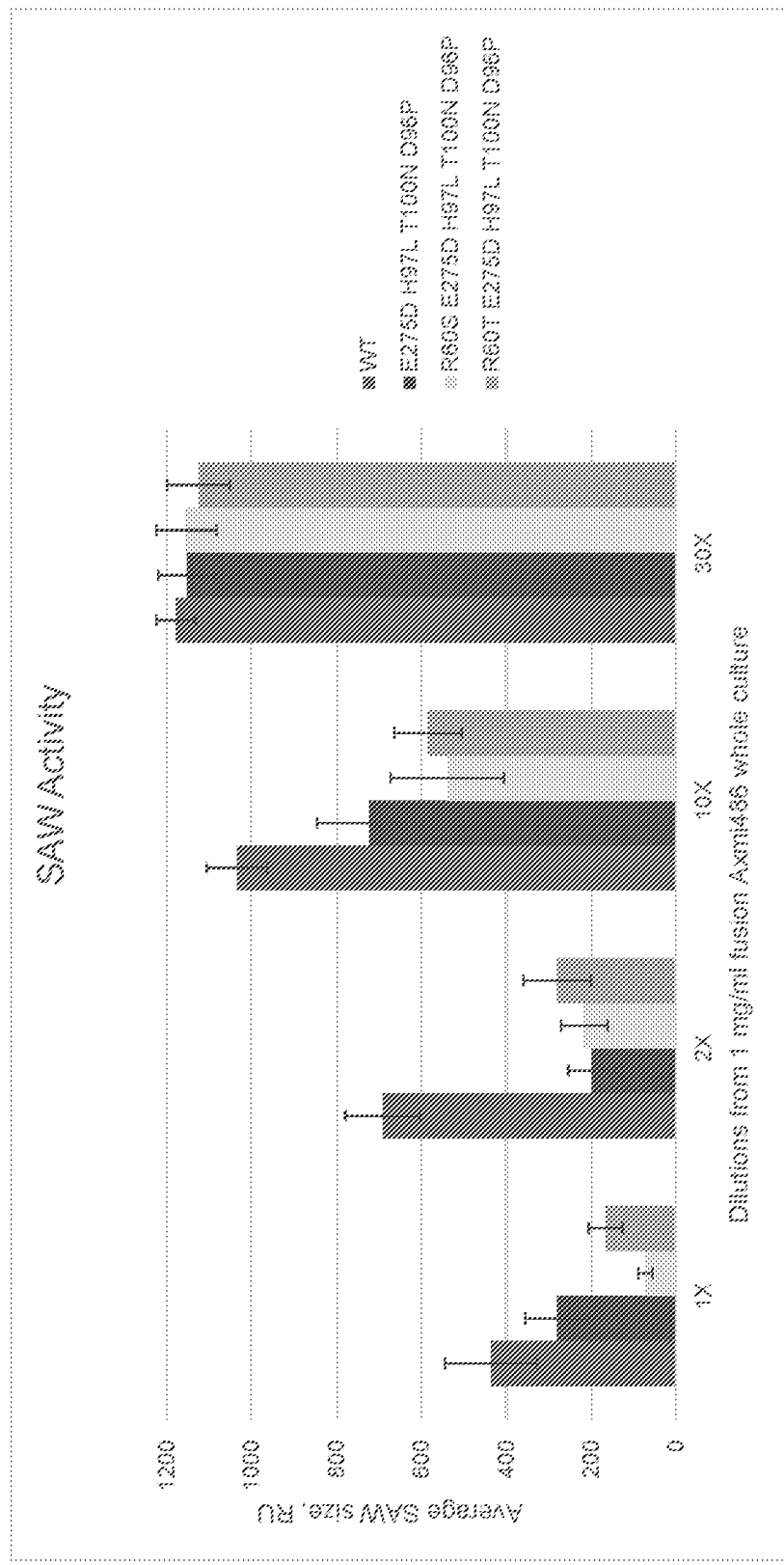
FIG. 1E—Axmi486 variant (respectively, E275+H97I+TI00N+D96P; R60S+E275D+H97L+TI00N+D96P; R60T+E275D+H97L+TI00N+D96P) dosage experiments and effects on Southern armyworm growth rates as compared to controls treated with wildtype Axmi486 (WT)
Figure 2A:
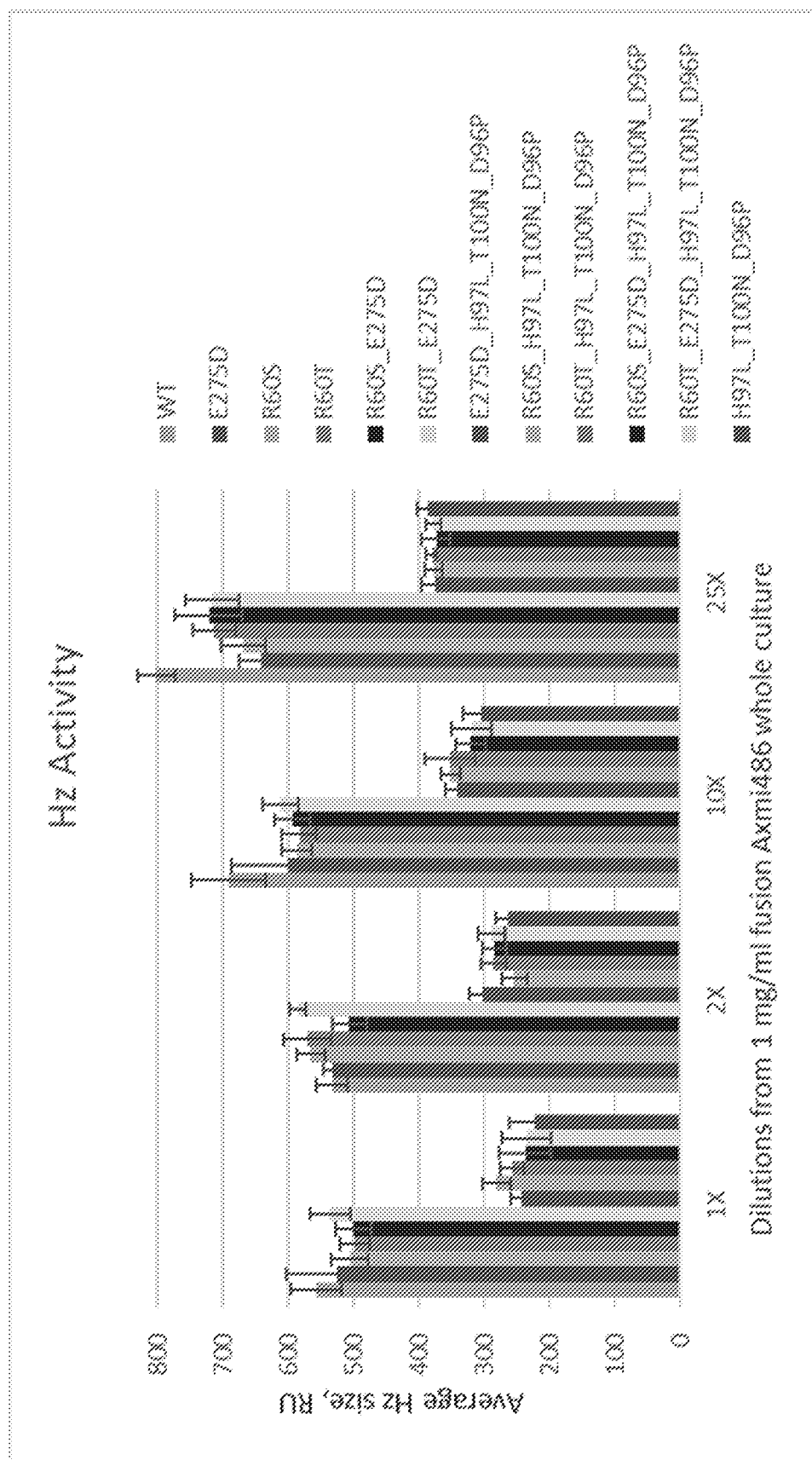
FIG. 2A—Axmi486 variant (respectively, E275D; R60S; R60T; R60S+E275D; R60T+E275D; E275D+H97L+TI00N+D96P; R60S+H97L+TI00N+D96P; R60T+H97L+TI00N+D96P; R60S+E275D+H97L+TI00N+D96P; R60T+E275D+H97L+TI00N+D96P; H97L+TI00N+D96P) dosage experiments and effects on *Helicoverpa zea* growth rates as compared to controls treated with wildtype Axmi486 (WT)
Figure 2B:
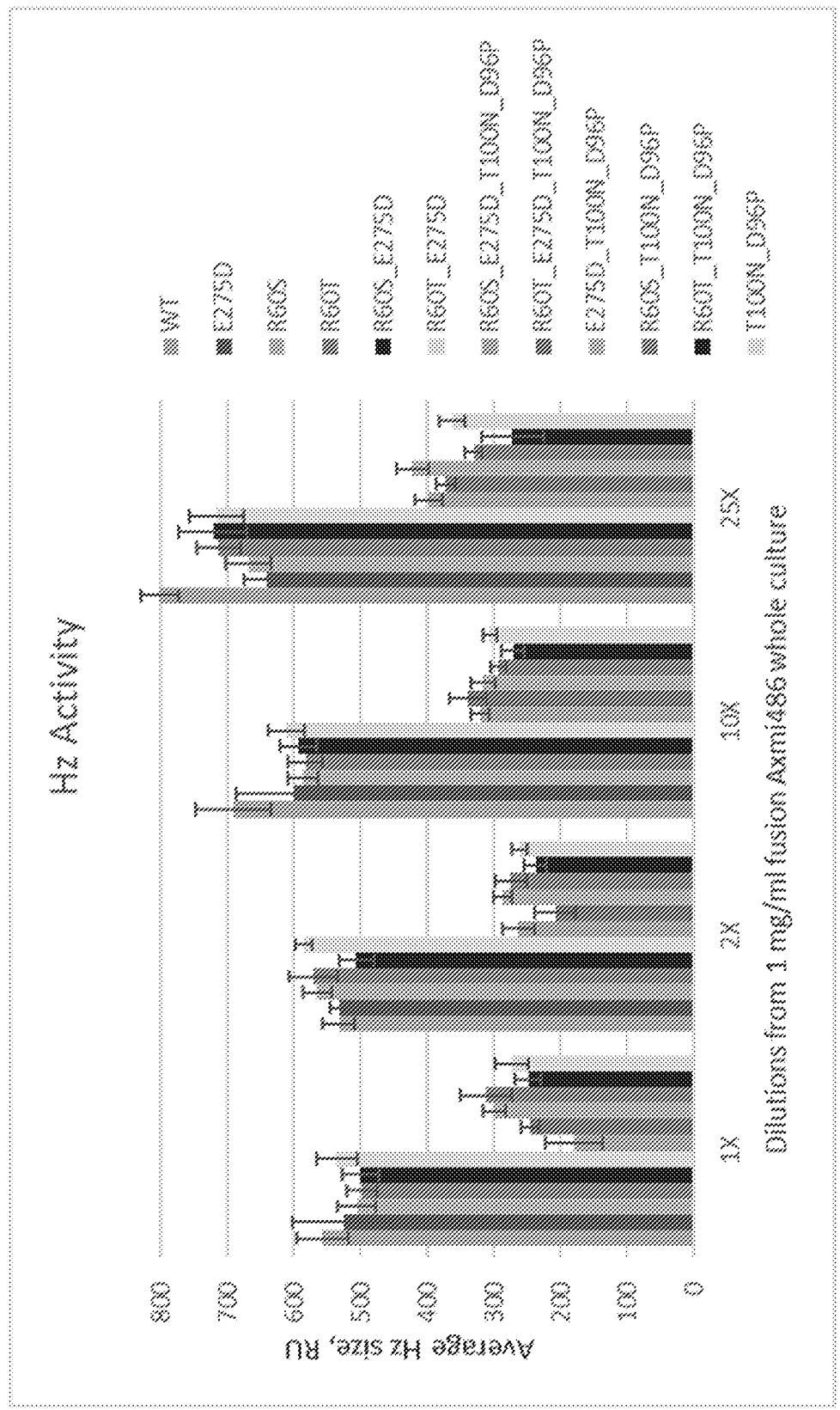
FIG. 2B—Axmi486 variant (respectively, E275D; R60S; R60T; R60S+E275D; R60T+E275D; R60S+E275D+TI00N+D96P; R60T+E275D+TI00N+D96P; E275D+TI00N+D96P; R60S+TI00N+D96P; R60T+TI00N+D96P; TI00N+D96P) dosage experiments and effects on *Helicoverpa zea* growth rates as compared to controls treated with wildtype Axmi486 (WT)
Figure 3A:
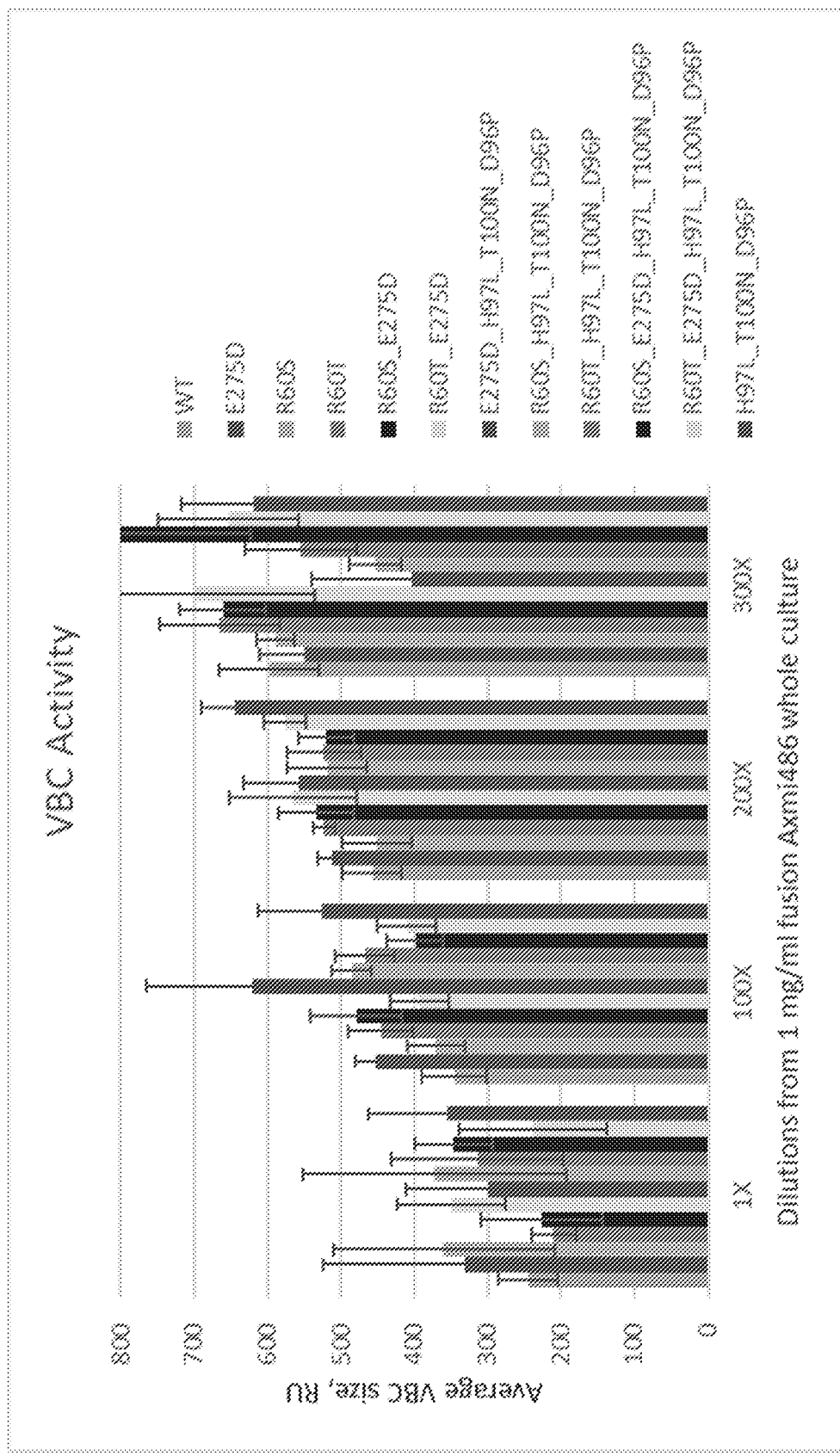
FIG. 3A—Axmi486 variant (respectively, E275D; R60S; R60T; R60S+E275D; R60T+E275D; E275D+H97L+TI00N+D96P; R60S+H97L+TI00N+D96P; R60T+H97L+TI00N+D96P; R60S+E275D+H97L+TI00N+D96P; R60T+E275D+H97L+TI00N+D96P; H97L+TI00N+D96P) dosage experiments and effects on *Anticarsia gemmatalis* growth rates as compared to controls treated with wildtype Axmi486 (WT)
Figure 3B:
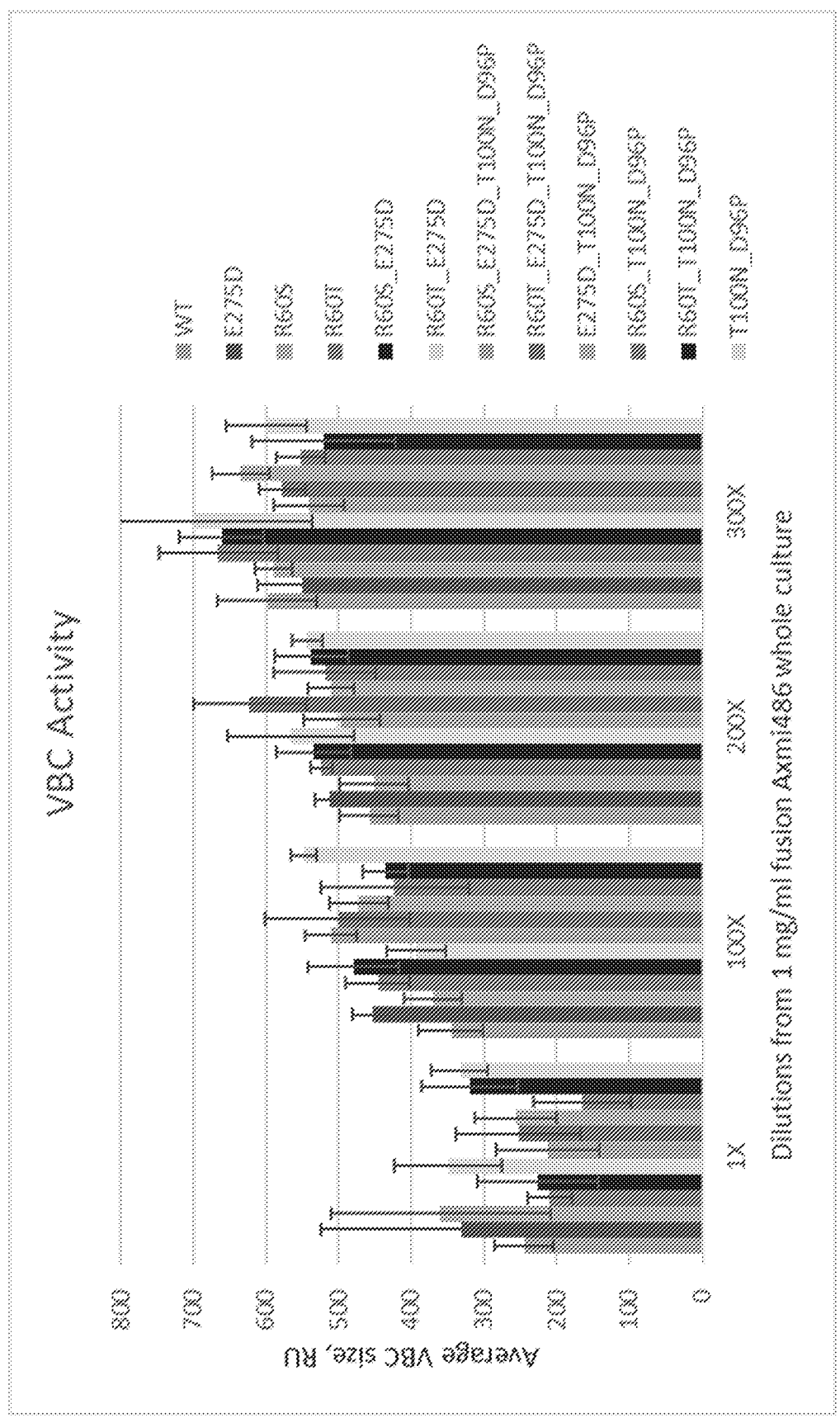
FIG. 3B—Axmi486 variant (respectively, E275D; R60S; R60T; R60S+E275D; R60T+E275D; R60S+E275D+ TI00N+D96P; R60T+E275D+TI00N+D96P; E275D+ TI00N+D96P; R60S+TI00N+D96P; R60T+TI00N+D96P; TI00N+D96P) dosage experiments and effects on *Anticarsia gemmatalis* growth rates as compared to controls treated with wildtype Axmi486 (WT)
Figure 4A:
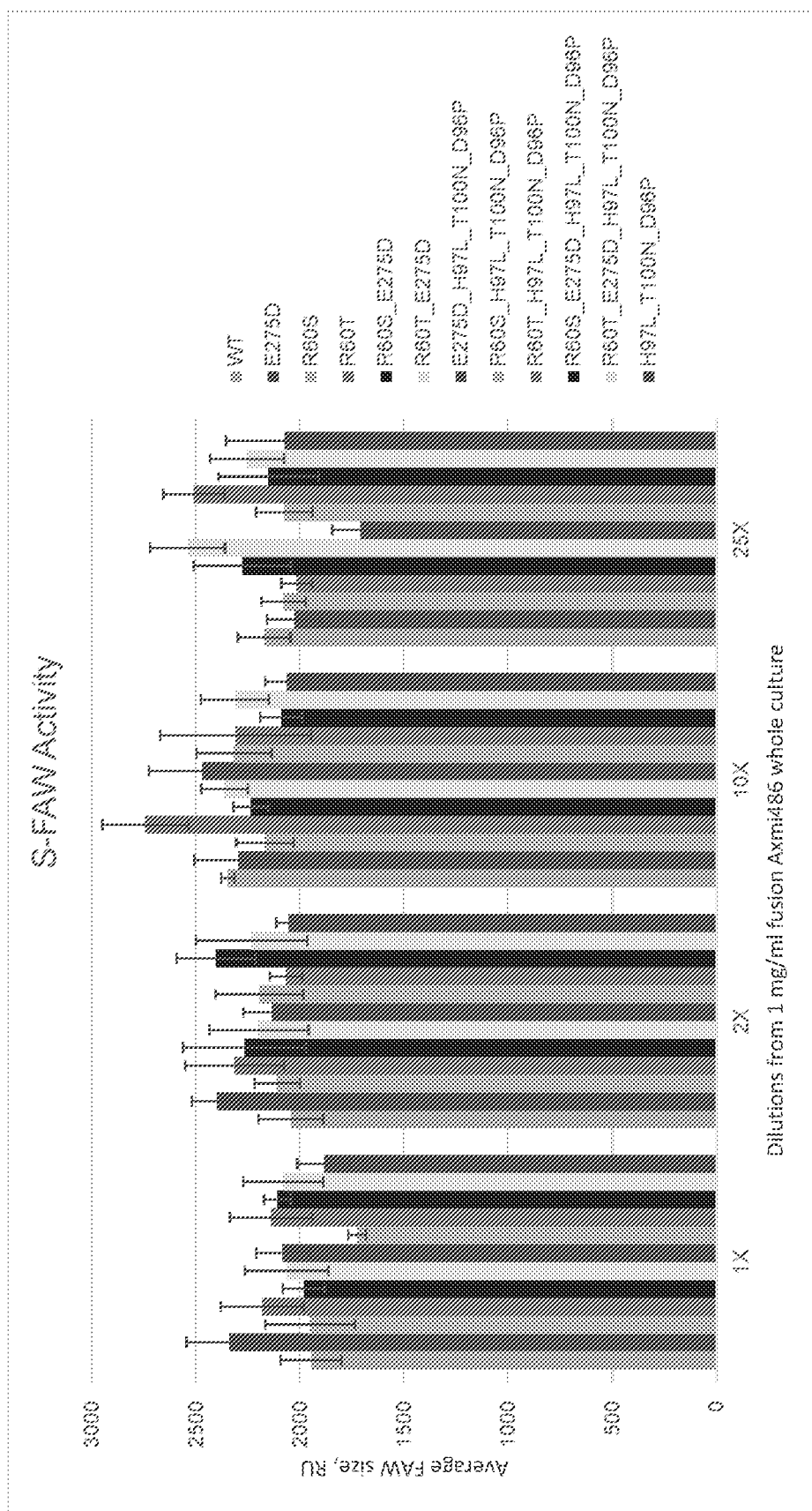
FIG. 4A—Axmi486 variant (respectively, E275D; R60S; R60T; R60S+E275D; R60T+E275D; E275D+H97L+ TI00N+D96P; R60S+H97L+TI00N+D96P; R60T+H97L+ TI00N+D96P; R60S+E275D+H97L+TI00N+D96P; R60T+ E275D+H97L+TI00N+D96P; H97L+TI00N+D96P) dosage experiments and effects on *Spodoptera frugiperda* growth rates as compared to controls treated with wildtype Axmi486 (WT)
Figure 4B:
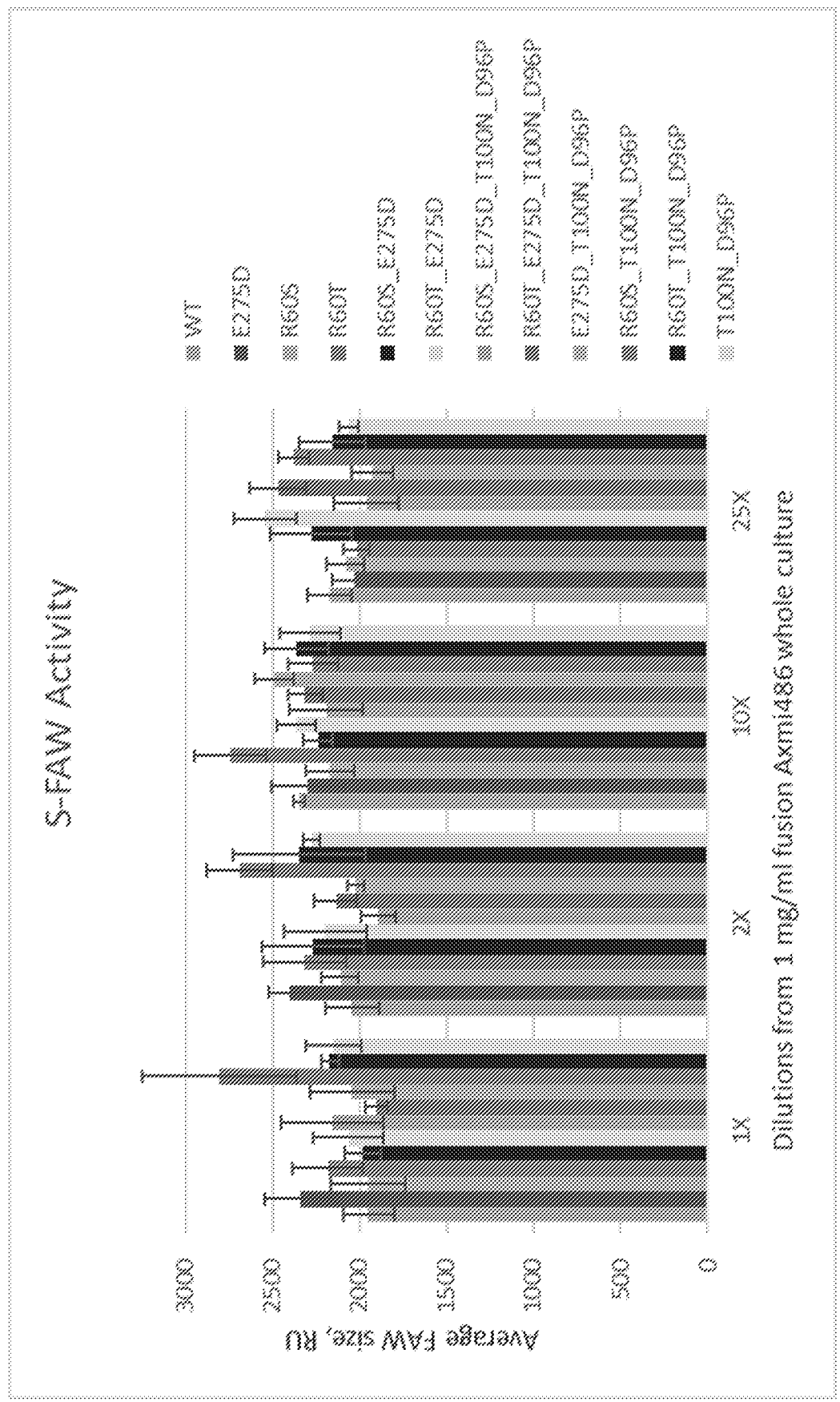
FIG. 4B—Axmi486 variant (respectively, E275D; R60S; R60T; R60S+E275D; R60T+E275D; R60S+E275D+ TI00N+D96P; R60T+E275D+TI00N+D96P; E275D+ TI00N+D96P; R60S+TI00N+D96P; R60T+TI00N+D96P; TI00N+D96P) dosage experiments and effects on *Spodoptera frugiperda* growth rates as compared to controls treated with wildtype Axmi486 (WT)
Figure 5:
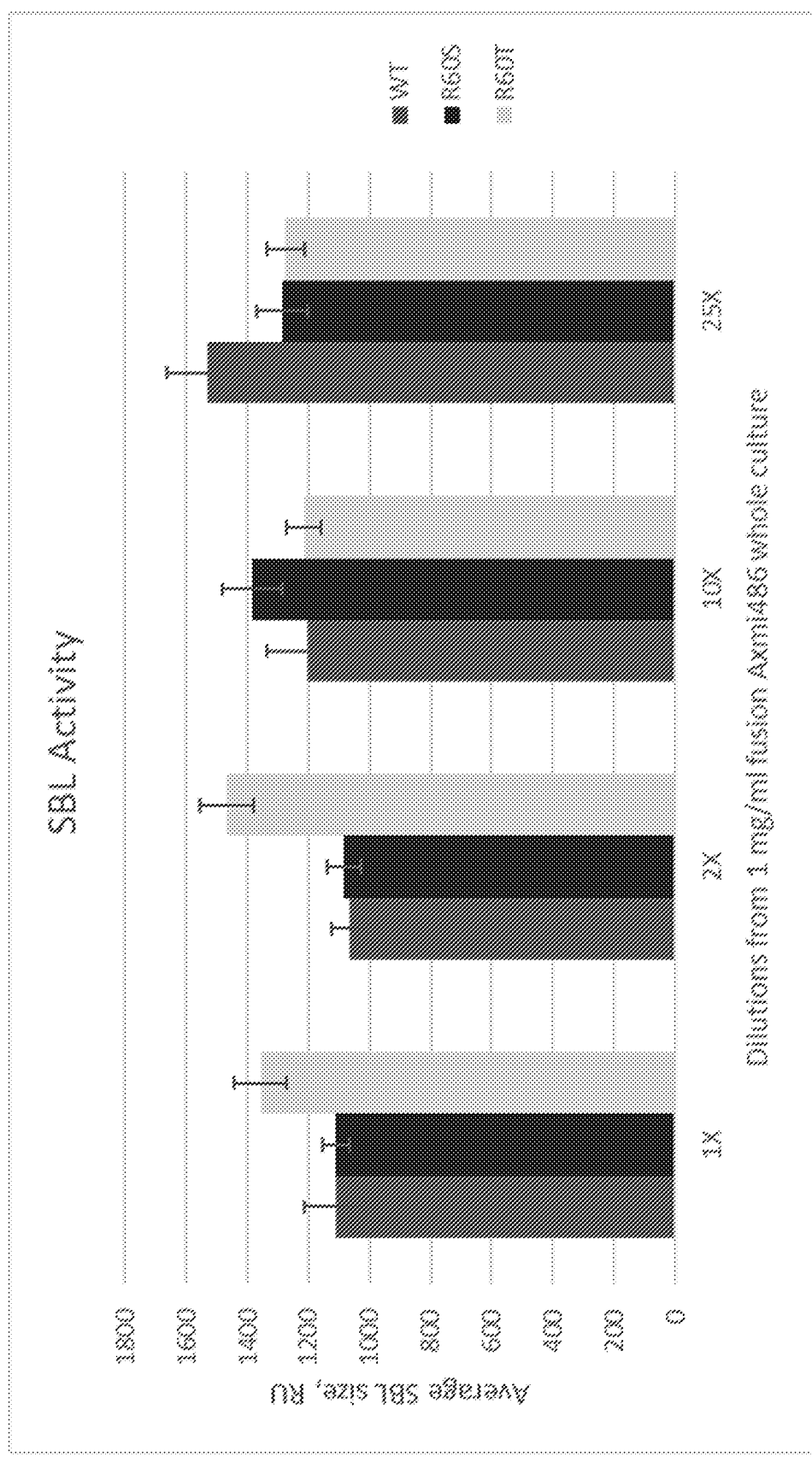
FIG. 5A—Axmi486 variant (respectively, R60S; R60T) dosage experiments and effects on *Chrysodeixis includens* growth rates as compared to controls treated with wildtype Axmi486 (WT)

The present invention is drawn to compositions and methods for regulating pest resistance or tolerance in organisms, particularly plants or plant cells. By "resistance" is intended that the pest (e.g., insect) is killed upon ingestion or other contact with the polypeptides of the invention. By "tolerance" is intended an impairment or reduction in the movement, feeding, reproduction, or other functions of the pest. The methods involve transforming organisms with a nucleotide sequence encoding a pesticidal protein of the invention. In particular, the nucleotide sequences of the invention are useful for preparing plants and microorganisms that possess pesticidal activity. Thus, transformed bacteria, plants, plant cells, plant tissues and seeds are provided. Compositions are pesticidal nucleic acids and proteins of *Bacillus* or other species. The sequences herein find use in the construction of expression vectors for subsequent transformation into organisms of interest, as probes for the isolation of other homologous (or partially homologous) genes, and for the generation of altered pesticidal proteins by methods known in the art, such as domain swapping or DNA shuffling. The proteins find use in controlling or killing lepidopteran, hemipteran, coleopteran, dipteran, and nematode pest populations and for producing compositions with pesticidal activity.

By "pesticidal toxin" or "pesticidal protein" is intended a toxin that has toxic activity against one or more pests, including, but not limited to, members of the Lepidoptera, Diptera, Hemiptera, and Coleoptera orders, or the Nematoda phylum, or a protein that has homology to such a protein. Pesticidal proteins include amino acid sequences deduced from the full-length nucleotide sequences disclosed herein, and amino acid sequences that are shorter than the full-length sequences, either due to the use of an alternate downstream start site, or due to processing that produces a shorter protein having pesticidal activity. Processing may occur in the organism the protein is expressed in, or in the pest after ingestion of the protein.

Thus, provided herein are novel isolated, recombinant or chimeric nucleotide sequences that confer pesticidal activity. Also provided are the amino acid sequences of the pesticidal proteins. The protein resulting from translation of this gene allows cells to control or kill pests that ingest it.

Isolated Nucleic Acid Molecules, and Variants and Fragments Thereof

One aspect of the invention pertains to isolated, recombinant or chimeric nucleic acid molecules comprising nucleotide sequences encoding pesticidal proteins and polypeptides or biologically active portions thereof, as well as nucleic acid molecules sufficient for use as hybridization probes to identify nucleic acid molecules encoding proteins with regions of sequence homology. Also encompassed herein are nucleotide sequences capable of hybridizing to the nucleotide sequences of the invention under stringent conditions as defined elsewhere herein. As used herein, the term "nucleic acid molecule" is intended to include DNA molecules (e.g., recombinant DNA, cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. The term "recombinant" encompasses polynucleotides or polypeptides that have been manipulated with respect to the native polynucleotide or polypeptide, such that the polynucleotide or polypeptide differs (e.g., in chemical composition or structure) from what is occurring in nature. In another embodiment, a "recombinant" polynucleotide is free of internal sequences (i.e. introns) that naturally occur in the genomic DNA of the organism from which the polynucleotide is derived. A typical example of such polynucleotide is a so-called Complementary DNA (cDNA).

An isolated, recombinant or chimeric nucleic acid (or DNA) is used herein to refer to a nucleic acid (or DNA) that is no longer in its natural environment, for example in an in vitro or in a recombinant bacterial or plant host cell. In some embodiments, an isolated, recombinant or chimeric nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated Axmi486 Variants nucleic acid molecules can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. Herein, "Axmi486 Variants" refers to the nucleic acid variants as indicated in SEQ ID Nos: 1-15 or a protein encoded by such nucleic acid variants (e.g. SEQ ID Nos: 16-30). In various embodiments, a Axmi486 Variant protein that is substantially free of cellular material includes preparations of protein having less than about 30%, 20%, 10%, or 5% (by dry weight) of non Axmi486 Variant protein (also referred to herein as a "contaminating protein"). In some embodiments, the recombinant nucleic acid of the invention comprises one or more nucleotide substitutions relative to any of SEQ ID NO:1 to 15, or a variant or fragment thereof wherein, said Axmi486 Variant shows improved resistance to a *Spodoptera* species as compared to a Axmi486 gene not comprising the indicated variations (e.g. nucleic acid SEQ ID Nos: 31 and/or variant proteins such as SEQ ID Nos 32-36 (Herein, "Axmi486")

Nucleotide sequences encoding the proteins of the present invention include the sequence set forth in any of SEQ ID NO: 1 to 15, and variants, fragments, and complements thereof that demonstrate increased resistance to *Spodoptera* species as compared to a Axmi486 gene not comprising the indicated variations. By "complement" is intended a nucleotide sequence that is sufficiently complementary to a given nucleotide sequence such that it can hybridize to the given nucleotide sequence to thereby form a stable duplex. The corresponding amino acid sequences for the pesticidal proteins encoded by these nucleotide sequences are set forth in any of SEQ ID NO: 16 to 30.

Nucleic acid molecules that are fragments of these nucleotide sequences encoding pesticidal proteins are also encompassed by the present invention. By "fragment" is intended a portion of the nucleotide sequence encoding a pesticidal protein. A fragment of a nucleotide sequence may encode a biologically active portion of a pesticidal protein, or it may be a fragment that can be used as a hybridization probe or PCR primer using methods disclosed below. Nucleic acid molecules that are fragments of a nucleotide sequence encoding a pesticidal protein comprise at least about 50, 100, 200, 300, 400, 500, 600, 700, 800, 900_contiguous nucleotides, or up to the number of nucleotides present in a full-length nucleotide sequence encoding a pesticidal protein disclosed herein, depending upon the intended use. By "contiguous" nucleotides is intended nucleotide residues that are immediately adjacent to one another. Fragments of the nucleotide sequences of the present invention will encode protein fragments that retain the biological activity of the pesticidal protein and, hence, retain pesticidal activity. Thus, biologically-active fragments of the polypeptides disclosed herein are also encompassed. By "retains activity" is intended that the fragment will have at least about 30%, at least about 50%, at least about 70%, 80%, 90%, 95% or higher of the pesticidal activity of the pesticidal protein. In one embodiment, the pesticidal activity is coleoptericidal activity. In another embodiment, the pesticidal activity is lepidoptericidal activity. In another embodiment, the pesticidal activity is nematocidal activity. In another embodiment, the pesticidal activity is diptericidal activity. In another embodiment, the pesticidal activity is hemiptericidal activity. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

A fragment of a nucleotide sequence encoding a pesticidal protein that encodes a biologically active portion of a protein of the invention will encode at least about 15, 25, 30, 50, 75, 100, 125, 150, 175, 200, 250, 300, 350, 400, 450 contiguous amino acids, or up to the total number of amino acids present in a full-length pesticidal protein of the invention. In some embodiments, the fragment is a proteolytic cleavage fragment. For example, the proteolytic cleavage fragment may have an N-terminal or a C-terminal truncation of at least about 100 amino acids, about 120, about 130, about 140, about 150, or about 160 amino acids relative to any of SEQ ID NO: 1 to 15. In some embodiments, the fragments encompassed herein result from the removal of the C-terminal crystallization domain, e.g., by proteolysis or by insertion of a stop codon in the coding sequence.

In various embodiments, the nucleic acid of the invention comprises a degenerate nucleic acid of any of SEQ ID NO:1 to 15, wherein said degenerate nucleotide sequence encodes the same amino acid sequence as any of SEQ ID NO:16 to 30.

Preferred pesticidal proteins of the present invention are encoded by a nucleotide sequence sufficiently identical to the nucleotide sequence of any of SEQ ID NO:1 to 15, or the pesticidal proteins are sufficiently identical to the amino acid sequence set forth in any of SEQ ID NO:16 to 30. By "sufficiently identical" is intended an amino acid or nucleotide sequence that has at least about 60% or 65% sequence identity, about 70% or 75% sequence identity, about 80% or 85% sequence identity, about 90%, 91%, 92%, 93%, 94%, 95%, 96%, 97%, 98%, 99% or greater sequence identity compared to a reference sequence using one of the alignment programs described herein using standard parameters. One of skill in the art will recognize that these values can be appropriately adjusted to determine corresponding identity of proteins encoded by two nucleotide sequences by taking into account codon degeneracy, amino acid similarity, reading frame positioning, and the like.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. In another embodiment, the percent identity is calculated across the entirety of the reference sequence (i.e., the sequence disclosed herein as any of SEQ ID NO: 1 to 30). The percent identity between two sequences can be determined using techniques similar to those described below, with or without allowing gaps. In calculating percent identity, typically exact matches are counted. A gap, i.e. a position in an alignment where a residue is present in one sequence but not in the other, is regarded as a position with non-identical residues.

The determination of percent identity between two sequences can be accomplished using a mathematical algorithm. A nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the BLASTN and BLASTX programs of Altschul et al. (1990) *J. Mol. Biol.* 215:403. BLAST nucleotide searches can be performed with the BLASTN program, score=100, wordlength=12, to obtain nucleotide sequences homologous to pesticidal-like nucleic acid molecules of the invention. BLAST protein searches can be performed with the BLASTX program, score=50, wordlength=3, to obtain amino acid sequences homologous to pesticidal protein molecules of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. Alignment may also be performed manually by inspection.

Another non-limiting example of a mathematical algorithm utilized for the comparison of sequences is the ClustalW algorithm (Higgins et al. (1994) *Nucleic Acids Res.*

22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the Vector NTI Program Suite (Invitrogen Corporation, Carlsbad, CA). After alignment of amino acid sequences with ClustalW, the percent amino acid identity can be assessed. A non-limiting example of a software program useful for analysis of ClustalW alignments is GENEDOC™ (a software program). GENEDOC™ (Karl Nicholas) allows assessment of amino acid (or DNA) similarity and identity between multiple proteins. Another non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG Wisconsin Genetics Software Package, Version 10 (available from Accelrys, Inc., 9685 Scranton Rd., San Diego, CA, USA). When utilizing the ALIGN program for comparing amino acid sequences, a PAM120 weight residue table, a gap length penalty of 12, and a gap penalty of 4 can be used.

Unless otherwise stated, GAP Version 10, which uses the algorithm of Needleman and Wunsch (1970) *J. Mol. Biol.* 48(3):443-453, will be used to determine sequence identity or similarity using the following parameters: % identity and % similarity for a nucleotide sequence using GAP Weight of 50 and Length Weight of 3, and the nwsgapdna.cmp scoring matrix; % identity or % similarity for an amino acid sequence using GAP weight of 8 and length weight of 2, and the BLOSUM62 scoring program. Equivalent programs may also be used. By "equivalent program" is intended any sequence comparison program that, for any two sequences in question, generates an alignment having identical nucleotide residue matches and an identical percent sequence identity when compared to the corresponding alignment generated by GAP Version 10.

The invention also encompasses variant nucleic acid molecules. "Variants" of the pesticidal protein encoding nucleotide sequences include those sequences that encode the pesticidal proteins disclosed herein but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the pesticidal proteins disclosed in the present invention as discussed below. Variant proteins encompassed by the present invention are biologically active, that is they continue to possess the desired biological activity of the native protein, that is, pesticidal activity. By "retains activity" is intended that the variant will have at least about 30%, at least about 50%, at least about 70%, or at least about 80% of the pesticidal activity of the native protein. A preferred embodiment of the invention are Axmi486 Variants that show increased activity to *Spodoptera* species pest (e.g. *Spodoptera eriadae*). Methods for measuring pesticidal activity are well known in the art. See, for example, Czapla and Lang (1990) *J. Econ. Entomol.* 83: 2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

The skilled artisan will further appreciate that changes can be introduced by mutation of the nucleotide sequences of the invention thereby leading to changes in the amino acid sequence of the encoded pesticidal proteins, without altering the biological activity of the proteins. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, conservative amino acid substitutions may be made at one or more, predicted, nonessential amino acid residues. A "nonessential" amino acid residue is a residue that can be altered from the wild-type sequence of a pesticidal protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Amino acid substitutions may be made in non-conserved regions that retain function. In general, such substitutions would not be made for conserved amino acid residues, or for amino acid residues residing within a conserved motif, where such residues are essential for protein activity. Examples of residues that are conserved and that may be essential for protein activity include, for example, residues that are identical between all proteins contained in an alignment of similar or related toxins to the sequences of the invention (e.g., residues that are identical in an alignment of homologous proteins). Examples of residues that are conserved but that may allow conservative amino acid substitutions and still retain activity include, for example, residues that have only conservative substitutions between all proteins contained in an alignment of similar or related toxins to the sequences of the invention (e.g., residues that have only conservative substitutions between all proteins contained in the alignment homologous proteins). However, one of skill in the art would understand that functional variants may have minor conserved or non-conserved alterations in the conserved residues.

Alternatively, variant nucleotide sequences can be made by introducing mutations randomly along all or part of the coding sequence, such as by saturation mutagenesis, and the resultant mutants can be screened for ability to confer pesticidal activity to identify mutants that retain activity. Following mutagenesis, the encoded protein can be expressed recombinantly, and the activity of the protein can be determined using standard assay techniques.

Using methods such as PCR, hybridization, and the like corresponding pesticidal sequences can be identified, such sequences having substantial identity to the sequences of the invention (e.g., at least about 70%, at least about 75%, 80%, 85%, 90%, 95% or more sequence identity across the entirety of the reference sequence) and having or conferring pesticidal activity. See, for example, Sambrook and Russell (2001) *Molecular Cloning: A Laboratory Manual.* (Cold Spring Harbor Laboratory Press, Cold Spring Harbor, NY) and Innis, et al. (1990) *PCR Protocols: A Guide to Methods and Applications* (Academic Press, NY).

In a hybridization method, all or part of the pesticidal nucleotide sequence can be used to screen cDNA or genomic libraries. Methods for construction of such cDNA and genomic libraries are generally known in the art and are disclosed in Sambrook and Russell, 2001, supra. The so-called hybridization probes may be genomic DNA fragments, cDNA fragments, RNA fragments, or other oligonucleotides, and may be labeled with a detectable group such as $^{32}P$, or any other detectable marker, such as other radioisotopes, a fluorescent compound, an enzyme, or an enzyme co-factor. Probes for hybridization can be made by labeling synthetic oligonucleotides based on the known pesticidal protein-encoding nucleotide sequence disclosed herein. Degenerate primers designed on the basis of conserved nucleotides or amino acid residues in the nucleotide sequence or encoded amino acid sequence can additionally be used. The probe typically comprises a region of nucleotide sequence that hybridizes under stringent conditions to at least about 12, at least about 25, at least about 50, 75, 100, 125, 150, 175, or 200 consecutive nucleotides of nucleotide sequence encoding a pesticidal protein of the invention or a fragment or variant thereof. Methods for the preparation of probes for hybridization are generally known in the art and are disclosed in Sambrook and Russell, 2001, supra herein incorporated by reference.

For example, an entire pesticidal sequence disclosed herein, or one or more portions thereof, may be used as a probe capable of specifically hybridizing to corresponding pesticidal protein-like sequences and messenger RNAs. To achieve specific hybridization under a variety of conditions, such probes include sequences that are unique and are preferably at least about 10 nucleotides in length, or at least about 20 nucleotides in length. Such probes may be used to amplify corresponding pesticidal sequences from a chosen organism or sample by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Cold Spring Harbor, New York).

Thus, the present invention encompasses probes for hybridization, as well as nucleotide sequences capable of hybridization to all or a portion of a nucleotide sequence of the invention (e.g., at least about 10, 25, 50, 100, 150, 200, 250, 300, 350, 400, 450, 500, or up to the full length of a nucleotide sequence disclosed herein). Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m=81.5°$ C.$+16.6$ (log M)$+0.41$ (% GC)$-0.61$ (% form)$-500/L$; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes,* Part I, Chapter 2 (Elsevier, New York); and Ausubel et al., eds. (1995) *Current Protocols in Molecular Biology,* Chapter 2 (Greene Publishing and Wiley-Interscience, New York). See Sambrook et al. (1989) *Molecular Cloning: A*

*Laboratory Manual* (2d ed., Cold Spring Harbor Laboratory Press, Cold Spring Harbor, New York).

Isolated Proteins and Variants and Fragments Thereof

Pesticidal proteins are also encompassed within the present invention. By "pesticidal protein" is intended a protein having the amino acid sequence set forth in any of SEQ ID NO:16 to 30. Fragments, biologically active portions, and variants thereof are also provided, and may be used to practice the methods of the present invention. An "isolated protein" or a "recombinant protein" is used to refer to a protein that is no longer in its natural environment, for example in vitro or in a recombinant bacterial or plant host cell. In some embodiments, the recombinant protein is a variant of any of SEQ ID NO: 16 to 30, wherein the variant comprises at least one amino acid substitution, deletion, or insertion relative to any of SEQ ID NO: 16 to 30.

"Fragments" or "biologically active portions" include polypeptide fragments comprising amino acid sequences sufficiently identical to the amino acid sequence set forth in any of SEQ ID NO: 16 to 30, and that exhibit pesticidal activity. A biologically active portion of a pesticidal protein can be a polypeptide that is, for example, 10, 25, 50, 100, 150, 200, 250, or more amino acids in length. Such biologically active portions can be prepared by recombinant techniques and evaluated for pesticidal activity. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety. As used here, a fragment comprises at least 8 contiguous amino acids of any of SEQ ID NO: 16 to 30. The invention encompasses other fragments, however, such as any fragment in the protein greater than about 10, 20, 30, 50, 100, 150, 200, 250 or more amino acids in length.

By "variants" is intended proteins or polypeptides having an amino acid sequence that is at least about 60%, 65%, about 70%, 75%, about 80%, 85%, about 90%, 91%, 92%, 93%, 94%, 95%, 96%, 97%, 98% or 99% identical to the amino acid sequence of any of SEQ ID NO: 16 to 30. Variants also include polypeptides encoded by a nucleic acid molecule that hybridizes to the nucleic acid molecule of any of SEQ ID NO: 16 to 30, or a complement thereof, under stringent conditions. Variants include polypeptides that differ in amino acid sequence due to mutagenesis. Variant proteins encompassed by the present invention are biologically active, that is they continue to possess the desired biological activity of the native protein, that is, retaining pesticidal activity. In some embodiments, the variants have improved activity relative to the native protein. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

Bacterial genes, such as the genes of this invention, quite often possess multiple methionine initiation codons in proximity to the start of the open reading frame. Often, translation initiation at one or more of these start codons will lead to generation of a functional protein. These start codons can include ATG codons. However, bacteria such as *Bacillus* sp. also recognize the codon GTG as a start codon, and proteins that initiate translation at GTG codons contain a methionine at the first amino acid. On rare occasions, translation in bacterial systems can initiate at a TTG codon, though in this event the TTG encodes a methionine. Furthermore, it is not often determined a priori which of these codons are used naturally in the bacterium. Thus, it is understood that use of one of the alternate methionine codons may also lead to generation of pesticidal proteins. These pesticidal proteins are encompassed in the present invention and may be used in the methods of the present invention. It will be understood that, when expressed in plants, it will be necessary to alter the alternate start codon to ATG for proper translation.

In various embodiments of the present invention, pesticidal proteins include amino acid sequences deduced from the full-length nucleotide sequences disclosed herein, and amino acid sequences that are shorter than the full-length sequences due to the use of an alternate downstream start site. Thus, the nucleotide sequence of the invention and/or vectors, host cells, and plants comprising the nucleotide sequence of the invention (and methods of making and using the nucleotide sequence of the invention) may comprise a nucleotide sequence encoding the amino acid sequence corresponding to any of SEQ ID NO: 16 to 30.

Antibodies to the polypeptides of the present invention, or to variants or fragments thereof, are also encompassed. Methods for producing antibodies are well known in the art (see, for example, Harlow and Lane (1988) *Antibodies: A Laboratory Manual*, Cold Spring Harbor Laboratory, Cold Spring Harbor, NY; U.S. Pat. No. 4,196,265).

Thus, one aspect of the invention concerns antibodies, single-chain antigen binding molecules, or other proteins that specifically bind to one or more of the protein or peptide molecules of the invention and their homologs, fusions or fragments. In a particularly preferred embodiment, the antibody specifically binds to a protein having the amino acid sequence set forth in any of SEQ ID NO: 16 to 30 or a fragment thereof. In another embodiment, the antibody specifically binds to a fusion protein comprising an amino acid sequence selected from the amino acid sequence set forth in any of SEQ ID NO: 16 to 30 or a fragment thereof. In various embodiments, the antibody that specifically binds to the protein of the invention or a fusion protein comprising the protein of the invention is a non-naturally occurring antibody.

Antibodies of the invention may be used to quantitatively or qualitatively detect the protein or peptide molecules of the invention, or to detect post translational modifications of the proteins. As used herein, an antibody or peptide is said to "specifically bind" to a protein or peptide molecule of the invention if such binding is not competitively inhibited by the presence of non-related molecules.

The antibodies of the invention may be contained within a kit useful for detection of the protein or peptide molecules of the invention. The invention further comprises a method of detecting the protein or peptide molecule of the invention (particularly a protein encoded by the amino acid sequence set forth in any of SEQ ID NO: 16 to 30, including variants or fragments thereof that are capable of specifically binding to the antibody of the invention) comprising contacting a sample with the antibody of the invention and determining whether the sample contains the protein or peptide molecule of the invention. Methods for utilizing antibodies for the detection of a protein or peptide of interest are known in the art.

Altered or Improved Variants

It is recognized that DNA sequences of a pesticidal protein may be altered by various methods, and that these alterations may result in DNA sequences encoding proteins with amino acid sequences different than that encoded by a pesticidal protein of the present invention. This protein may be altered in various ways including amino acid substitutions, deletions, truncations, and insertions of one or more amino acids of any of SEQ ID NO:16 to 30, including up to about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 100, about 105, about 110, about 115, about 120, about 125, about 130, about 135, about 140, about 145, about 150, about 155, or more amino acid substitutions, deletions or insertions. Methods for such manipulations are generally known in the art. For example, amino acid sequence variants of a pesticidal protein can be prepared by mutations in the DNA. This may also be accomplished by one of several forms of mutagenesis and/or in directed evolution. In some aspects, the changes encoded in the amino acid sequence will not substantially affect the function of the protein. Such variants will possess the desired pesticidal activity. However, it is understood that the ability of a pesticidal protein to confer pesticidal activity may be improved by the use of such techniques upon the compositions of this invention. For example, one may express a pesticidal protein in host cells that exhibit high rates of base misincorporation during DNA replication, such as XL-1 Red (Stratagene, La Jolla, CA). After propagation in such strains, one can isolate the DNA (for example by preparing plasmid DNA, or by amplifying by PCR and cloning the resulting PCR fragment into a vector), culture the pesticidal protein mutations in a non-mutagenic strain, and identify mutated genes with pesticidal activity, for example by performing an assay to test for pesticidal activity. Generally, the protein is mixed and used in feeding assays or the toxin is exposed directly to the insect. See, for example Marrone et al. (1985) *J. of Economic Entomology* 78:290-293 and Cira et al. (2017) *J Pest Sci* 90:1257-1268. Such assays can include contacting plants with one or more pests and determining the plant's ability to survive and/or cause the death of the pests. Examples of mutations that result in increased toxicity are found in Schnepf et al. (1998) *Microbiol. Mol. Biol. Rev.* 62:775-806.

Alternatively, alterations may be made to the protein sequence of many proteins at the amino or carboxy terminus without substantially affecting activity. This can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity, or epitope to facilitate either protein purification, protein detection, or other experimental uses known in the art (3) target secretion or translation of a protein to a subcellular organelle, such as the periplasmic space of Gram-negative bacteria, or the endoplasmic reticulum of eukaryotic cells, the latter of which often results in glycosylation of the protein.

Variant nucleotide and amino acid sequences of the present invention also encompass sequences derived from mutagenic and recombinogenic procedures such as DNA shuffling. With such a procedure, one or more different pesticidal protein coding regions can be used to create a new pesticidal protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a pesticidal gene of the invention and other known pesticidal genes to obtain a new gene coding for a protein with an improved property of interest, such as an increased insecticidal activity. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

Domain swapping or shuffling is another mechanism for generating altered pesticidal proteins. Domains may be swapped between pesticidal proteins, resulting in hybrid or chimeric toxins with improved pesticidal activity or target spectrum. Methods for generating recombinant proteins and testing them for pesticidal activity are well known in the art (see, for example, Naimov et al. (2001) *Appl. Environ. Microbiol.* 67:5328-5330; de Maagd et al. (1996) *Appl. Environ. Microbiol.* 62:1537-1543; Ge et al. (1991) *J. Biol. Chem.* 266:17954-17958; Schnepf et al. (1990) *J. Biol. Chem.* 265:20923-20930; Rang et al. 91999) *Appl. Environ. Microbiol.* 65:2918-2925).

In yet another embodiment, variant nucleotide and/or amino acid sequences can be obtained using one or more of error-prone PCR, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, gene site saturation mutagenesis, permutational mutagenesis, synthetic ligation reassembly (SLR), recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation, and the like.

Vectors

A pesticidal sequence of the invention may be provided in an expression cassette for expression in a host cell of interest, e.g. a plant cell or a microbe. By "plant expression cassette" is intended a DNA construct that is capable of resulting in the expression of a protein from an open reading frame in a plant cell. Typically, these contain a promoter and a coding sequence. Often, such constructs will also contain a 3' untranslated region. Such constructs may contain a "signal sequence" or "leader sequence" to facilitate co-translational or post-translational transport of the peptide to certain intracellular structures such as the chloroplast (or other plastid), endoplasmic reticulum, or Golgi apparatus.

By "signal sequence" is intended a sequence that is known or suspected to result in co-translational or post-translational peptide transport across the cell membrane. In eukaryotes, this typically involves secretion into the Golgi apparatus, with some resulting glycosylation. Insecticidal toxins of bacteria are often synthesized as protoxins, which are protolytically activated in the gut of the target pest (Chang (1987) *Methods Enzymol.* 153:507-516). In some embodiments of the present invention, the signal sequence is located in the native sequence, or may be derived from a sequence of the invention. By "leader sequence" is intended any sequence that when translated, results in an amino acid sequence sufficient to trigger co-translational transport of the peptide chain to a subcellular organelle. Thus, this includes leader sequences targeting transport and/or glycosylation by passage into the endoplasmic reticulum, passage to vacuoles, plastids including chloroplasts, mitochondria, and the like. Thus, further provided herein is a polypeptide comprising an amino acid sequence of the present invention that is operably linked to a heterologous leader or signal sequence.

By "plant transformation vector" is intended a DNA molecule that is necessary for efficient transformation of a plant cell. Such a molecule may consist of one or more plant expression cassettes, and may be organized into more than one "vector" DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451). "Vector" refers to a nucleic acid construct designed for transfer between different host cells. "Expression vector" refers to a vector that has the ability to incorporate, integrate and express heterologous DNA sequences or fragments in a foreign cell. The cassette will include 5' and/or 3' regulatory sequences operably linked to a sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. In some embodiments, the nucleotide sequence is operably linked to a heterologous promoter capable of directing expression of said nucleotide sequence in a host cell, such as a microbial host cell or a plant host cell. The cassette may additionally contain at least one additional gene to be co-transformed into the organism. Alternatively, the additional gene(s) can be provided on multiple expression cassettes.

In various embodiments, the nucleotide sequence of the invention is operably linked to a heterologous promoter capable of directing expression of the nucleotide sequence in a cell, e.g., in a plant cell or a microbe. "Promoter" refers to a nucleic acid sequence that functions to direct transcription of a downstream coding sequence. The promoter together with other transcriptional and translational regulatory nucleic acid sequences (also termed "control sequences") are necessary for the expression of a DNA sequence of interest.

Such an expression cassette is provided with a plurality of restriction sites for insertion of the pesticidal sequence to be under the transcriptional regulation of the regulatory regions.

The expression cassette will include in the 5'-3' direction of transcription, a transcriptional and translational initiation region (i.e., a promoter), a DNA sequence of the invention, and a translational and transcriptional termination region (i.e., termination region) functional in plants. The promoter may be native or analogous, or foreign or heterologous, to the plant host and/or to the DNA sequence of the invention. Additionally, the promoter may be the natural sequence or alternatively a synthetic sequence. Where the promoter is "native" or "homologous" to the plant host, it is intended that the promoter is found in the native plant into which the promoter is introduced. Where the promoter is "foreign" or "heterologous" to the DNA sequence of the invention, it is intended that the promoter is not the native or naturally occurring promoter for the operably linked DNA sequence of the invention. The promoter may be inducible or constitutive. It may be naturally-occurring, may be composed of portions of various naturally-occurring promoters, or may be partially or totally synthetic. Guidance for the design of promoters is provided by studies of promoter structure, such as that of Harley and Reynolds (1987) *Nucleic Acids Res.* 15:2343-2361. Also, the location of the promoter relative to the transcription start may be optimized. See, e.g., Roberts et al. (1979) *Proc. Natl. Acad. Sci. USA*, 76:760-764. Many suitable promoters for use in plants are well known in the art.

For instance, suitable constitutive promoters for use in plants include: the promoters from plant viruses, such as the peanut chlorotic streak caulimovirus (PClSV) promoter (U.S. Pat. No. 5,850,019); the 35S promoter from cauliflower mosaic virus (CaMV) (Odell et al. (1985) *Nature* 313:810-812); the 35S promoter described in Kay et al. (1987) *Science* 236: 1299-1302; promoters of *Chlorella* virus methyltransferase genes (U.S. Pat. No. 5,563,328) and the full-length transcript promoter from figwort mosaic virus (FMV) (U.S. Pat. No. 5,378,619); the promoters from such genes as rice actin (McElroy et al. (1990) *Plant Cell* 2:163-171 and U.S. Pat. No. 5,641,876); ubiquitin (Christensen et al. (1989) *Plant Mol. Biol.* 12:619-632 and Christensen et al. (1992) *Plant Mol. Biol.* 18:675-689) and Grefen et al. (2010) *Plant J*, 64:355-365; pEMU (Last et al. (1991) *Theor. Appl. Genet.* 81:581-588); MAS (Velten et al. (1984) *EMBO J.* 3:2723-2730 and U.S. Pat. No. 5,510,474); maize H3 histone (Lepetit et al. (1992) *Mol. Gen. Genet.* 231:276-285 and Atanassova et al. (1992) *Plant J.* 2(3):291-300); *Brassica napus* ALS3 (PCT application WO97/41228); a plant ribulose-biscarboxylase/oxygenase (RuBisCO) small subunit gene; the circovirus (AU 689 311) or the Cassava vein mosaic virus (CsVMV, U.S. Pat. No. 7,053,205); promoters from soybean (Pbdc6 or Pbdc7, described in WO/2014/150449 or ubiquitin 3 promoter described in U.S. Pat. Nos. 7,393,948 and 8,395,021); and promoters of various *Agrobacterium* genes (see U.S. Pat. Nos. 4,771,002; 5,102,796; 5,182,200; and 5,428,147).

Suitable inducible promoters for use in plants include: the promoter from the ACE1 system which responds to copper (Mett et al. (1993) *PNAS* 90:4567-4571); the promoter of the maize In2 gene which responds to benzenesulfonamide herbicide safeners (Hershey et al. (1991) *Mol. Gen. Genetics* 227:229-237 and Gatz et al. (1994) *Mol. Gen. Genetics* 243:32-38); and the promoter of the Tet repressor from Tn10 (Gatz et al. (1991) *Mol. Gen. Genet.* 227:229-237). Another inducible promoter for use in plants is one that responds to an inducing agent to which plants do not normally respond. An exemplary inducible promoter of this type is the inducible promoter from a steroid hormone gene, the transcriptional activity of which is induced by a glucocorticosteroid hormone (Schena et al. (1991) *Proc. Natl. Acad. Sci. USA* 88:10421) or the recent application of a chimeric transcription activator, XVE, for use in an estrogen receptor-based inducible plant expression system activated by estradiol (Zuo et al. (2000) *Plant J.,* 24:265-273). Other inducible promoters for use in plants are described in EP 332104, PCT WO 93/21334 and PCT WO 97/06269 which are herein incorporated by reference in their entirety. Promoters composed of portions of other promoters and partially or totally synthetic promoters can also be used. See, e.g., Ni et al. (1995) *Plant J.* 7:661-676 and PCT WO 95/14098 describing such promoters for use in plants.

In one embodiment of this invention, a promoter sequence specific for particular regions or tissues of plants can be used to express the pesticidal proteins of the invention, such as promoters specific for seeds (Datla, R. et al., 1997, Biotechnology Ann. Rev. 3, 269-296), especially the napin promoter (EP 255 378 A1), the phaseolin promoter, the glutenin promoter, the helianthinin promoter (WO92/17580), the albumin promoter (WO98/45460), the oleosin promoter (WO98/45461), the SAT1 promoter or the SAT3 promoter (PCT/US98/06978).

Use may also be made of an inducible promoter advantageously chosen from the phenylalanine ammonia lyase (PAL), HMG-CoA reductase (HMG), chitinase, glucanase, proteinase inhibitor (PI), PR1 family gene, nopaline synthase (nos) and vspB promoters (U.S. Pat. No. 5,670,349, Table 3), the HMG2 promoter (U.S. Pat. No. 5,670,349), the apple beta-galactosidase (ABG1) promoter and the apple aminocyclopropane carboxylate synthase (ACC synthase) promoter (WO98/45445). Multiple promoters can be used in the constructs of the invention, including in succession.

The promoter may include, or be modified to include, one or more enhancer elements. In some embodiments, the promoter may include a plurality of enhancer elements. Promoters containing enhancer elements provide for higher levels of transcription as compared to promoters that do not include them. Suitable enhancer elements for use in plants include the PClSV enhancer element (U.S. Pat. No. 5,850,019), the CaMV 35S enhancer element (U.S. Pat. Nos. 5,106,739 and 5,164,316) and the FMV enhancer element (Maiti et al. (1997) *Transgenic Res.* 6:143-156); the translation activator of the tobacco mosaic virus (TMV) described in Application WO87/07644, or of the tobacco etch virus (TEV) described by Carrington & Freed 1990, J. Virol. 64: 1590-1597, for example, or introns such as the adh1 intron of maize or intron 1 of rice actin. See also PCT WO96/23898, WO2012/021794, WO2012/021797, WO2011/084370, and WO2011/028914.

Often, such constructs can contain 5' and 3' untranslated regions. Such constructs may contain a "signal sequence" or "leader sequence" to facilitate co-translational or post-translational transport of the peptide of interest to certain intracellular structures such as the chloroplast (or other plastid), endoplasmic reticulum, or Golgi apparatus, or to be secreted. For example, the construct can be engineered to contain a signal peptide to facilitate transfer of the peptide to the endoplasmic reticulum. By "signal sequence" is intended a sequence that is known or suspected to result in co-translational or post-translational peptide transport across the cell membrane. In eukaryotes, this typically involves secretion into the Golgi apparatus, with some resulting glycosylation. By "leader sequence" is intended any sequence that, when translated, results in an amino acid sequence sufficient to trigger co-translational transport of the peptide chain to a sub-cellular organelle. Thus, this includes leader sequences targeting transport and/or glycosylation by passage into the endoplasmic reticulum, passage to vacuoles, plastids including chloroplasts, mitochondria, and the like. It may also be preferable to engineer the plant expression cassette to contain an intron, such that mRNA processing of the intron is required for expression.

By "3' untranslated region" is intended a polynucleotide located downstream of a coding sequence. Polyadenylation signal sequences and other sequences encoding regulatory signals capable of affecting the addition of polyadenylic acid tracts to the 3' end of the mRNA precursor are 3' untranslated regions. By "5' untranslated region" is intended a polynucleotide located upstream of a coding sequence.

Other upstream or downstream untranslated elements include enhancers. Enhancers are polynucleotides that act to increase the expression of a promoter region. Enhancers are well known in the art and include, but are not limited to, the SV40 enhancer region and the 35S enhancer element.

The termination region may be native with the transcriptional initiation region, may be native with the operably linked DNA sequence of interest, may be native with the plant host, or may be derived from another source (i.e., foreign or heterologous to the promoter, the DNA sequence of interest, the plant host, or any combination thereof). Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed host cell (synthetic DNA sequence). That is, the genes can be synthesized using host cell-preferred codons for improved expression, or may be synthesized using codons at a host-preferred codon usage frequency. Expression of the open reading frame of the synthetic DNA sequence in a cell results in production of the polypeptide of the invention. Synthetic DNA sequences can be useful to simply remove unwanted restriction endonuclease sites, to facilitate DNA cloning strategies, to alter or remove any potential codon bias, to alter or improve GC content, to remove or alter alternate reading frames, and/or to alter or remove intron/exon splice recognition sites, polyadenylation sites, Shine-Delgarno sequences, unwanted promoter elements and the like that may be present in a native DNA sequence. Generally, the GC content of the gene will be increased. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, U.S. Patent Publication No. 20090137409, and Murray et al. (1989) *Nucleic Acids Res.* 17:477-498, herein incorporated by reference.

It is also possible that synthetic DNA sequences may be utilized to introduce other improvements to a DNA sequence, such as introduction of an intron sequence, creation of a DNA sequence that in expressed as a protein fusion to organelle targeting sequences, such as chloroplast transit peptides, apoplast/vacuolar targeting peptides, or peptide sequences that result in retention of the resulting peptide in the endoplasmic reticulum. Thus, in one embodiment, the pesticidal protein is targeted to the chloroplast for expression. In this manner, where the pesticidal protein is not directly inserted into the chloroplast, the expression cassette will additionally contain a nucleic acid encoding a transit peptide to direct the pesticidal protein to the chloroplasts. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

The pesticidal gene to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Plant Transformation

Methods of the invention involve introducing a nucleotide construct into a plant. By "introducing" is intended to present to the plant the nucleotide construct in such a manner that the construct gains access to the interior of a cell of the plant. The methods of the invention do not require that a particular method for introducing a nucleotide construct to a plant is used, only that the nucleotide construct gains access to the interior of at least one cell of the plant. Methods for introducing nucleotide constructs into plants are known in the art including, but not limited to, stable transformation methods, transient transformation methods, and virus-mediated methods.

By "plant" is intended whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen).

"Transgenic plants" or "transformed plants" or "stably transformed" plants or cells or tissues refers to plants that have incorporated or integrated exogenous nucleic acid sequences or DNA fragments into the plant cell. These nucleic acid sequences include those that are exogenous, or not present in the untransformed plant cell, as well as those that may be endogenous, or present in the untransformed plant cell. "Heterologous" generally refers to the nucleic acid sequences that are not endogenous to the cell or part of the native genome in which they are present, and have been added to the cell by infection, transfection, microinjection, electroporation, microprojection, or the like.

The transgenic plants of the invention express one or more of the novel toxin sequences disclosed herein. In some embodiments, the protein or nucleotide sequence of the invention is advantageously combined in plants with other genes which encode proteins or RNAs that confer useful agronomic properties to such plants. Among the genes which encode proteins or RNAs that confer useful agronomic properties on the transformed plants, mention can be made of the DNA sequences encoding proteins which confer tolerance to one or more herbicides, and others which confer tolerance to certain insects, those which confer tolerance to certain diseases, DNAs that encodes RNAs that provide nematode or insect control, and the like. Such genes are in particular described in published PCT Patent Applications WO91/02071 and WO95/06128 and in U.S. Pat. No. 7,923, 602 and US Patent Application Publication No. 20100166723, each of which is herein incorporated by reference in its entirety.

Among the DNA sequences encoding proteins which confer tolerance to certain herbicides on the transformed plant cells and plants, mention can be made of a bar or PAT gene or the *Streptomyces coelicolor* gene described in WO2009/152359 which confers tolerance to glufosinate herbicides, a gene encoding a suitable EPSPS which confers tolerance to herbicides having EPSPS as a target, such as glyphosate and its salts (U.S. Pat. Nos. 4,535,060, 4,769, 061, 5,094,945, 4,940,835, 5,188,642, 4,971,908, 5,145,783, 5,310,667, 5,312,910, 5,627,061, 5,633,435), a gene encoding glyphosate-n-acetyltransferase (for example, U.S. Pat. Nos. 8,222,489, 8,088,972, 8,044,261, 8,021,857, 8,008, 547, 7,999,152, 7,998,703, 7,863,503, 7,714,188, 7,709,702, 7,666,644, 7,666,643, 7,531,339, 7,527,955, and 7,405, 074), a gene encoding glyphosate oxydoreductase (for example, U.S. Pat. No. 5,463,175), or a gene encoding an HPPD inhibitor-tolerant protein (for example, the HPPD inhibitor tolerance genes described in WO 2004/055191, WO 199638567, U.S. Pat. No. 6,791,014, WO2011/068567, WO2011/076345, WO2011/085221, WO2011/094205, WO2011/068567, WO2011/094199, WO2011/094205, WO2011/145015, WO2012/056401, and WO2014/043435).

Among the DNA sequences encoding a suitable EPSPS which confer tolerance to the herbicides which have EPSPS as a target, mention will more particularly be made of the gene which encodes a plant EPSPS, in particular maize EPSPS, particularly a maize EPSPS which comprises two mutations, particularly a mutation at amino acid position 102 and a mutation at amino acid position 106 (WO2004/074443), and which is described in Patent Application U.S. Pat. No. 6,566,587, hereinafter named double mutant maize EPSPS or 2mEPSPS, or the gene which encodes an EPSPS isolated from *Agrobacterium* and which is described by sequence ID No. 2 and sequence ID No. 3 of U.S. Pat. No. 5,633,435, also named CP4.

Among the DNA sequences encoding a suitable EPSPS which confer tolerance to the herbicides which have EPSPS as a target, mention will more particularly be made of the gene which encodes an EPSPS GRG23 from *Arthrobacter globiformis*, but also the mutants GRG23 ACE1, GRG23 ACE2, or GRG23 ACE3, particularly the mutants or variants of GRG23 as described in WO2008/100353, such as GRG23 (ace3)R173K of SEQ ID No. 29 in WO2008/100353.

In the case of the DNA sequences encoding EPSPS, and more particularly encoding the above genes, the sequence encoding these enzymes is advantageously preceded by a sequence encoding a transit peptide, in particular the "optimized transit peptide" described in U.S. Pat. No. 5,510,471 or 5,633,448.

Exemplary herbicide tolerance traits that can be combined with the nucleic acid sequence of the invention further include at least one ALS (acetolactate synthase) inhibitor (WO2007/024782); a mutated *Arabidopsis* ALS/AHAS gene (U.S. Pat. No. 6,855,533); genes encoding 2,4-D-monooxygenases conferring tolerance to 2,4-D (2,4-dichlorophenoxyacetic acid) by metabolization (U.S. Pat. No. 6,153,401); and, genes encoding Dicamba monooxygenases conferring tolerance to dicamba (3,6-dichloro-2-methoxybenzoic acid) by metabolization (US 2008/0119361 and US 2008/0120739).

In various embodiments, the nucleic acid of the invention is stacked with one or more herbicide tolerant genes, including one or more HPPD inhibitor herbicide tolerant genes, and/or one or more genes tolerant to glyphosate and/or glufosinate.

Among the DNA sequences encoding proteins concerning properties of tolerance to insects, mention will more particularly be made of the Bt proteins widely described in the literature and well known to those skilled in the art. Mention will also be made of proteins extracted from bacteria such as *Photorhabdus* (WO97/17432 & WO98/08932).

Among such DNA sequences encoding proteins of interest which confer novel properties of tolerance to insects, mention will more particularly be made of the Bt Cry or VIP proteins widely described in the literature and well known to those skilled in the art. These include the Cry1F protein or hybrids derived from a Cry1F protein (e.g., the hybrid Cry1A-Cry1F proteins described in U.S. Pat. Nos. 6,326, 169; 6,281,016; 6,218,188, or toxic fragments thereof), the Cry1A-type proteins or toxic fragments thereof, preferably the Cry1Ac protein or hybrids derived from the Cry1Ac protein (e.g., the hybrid Cry1Ab-Cry1Ac protein described in U.S. Pat. No. 5,880,275) or the Cry1Ab or Bt2 protein or insecticidal fragments thereof as described in EP451878, the Cry2Ae, Cry2Af or Cry2Ag proteins as described in WO2002/057664 or toxic fragments thereof, the Cry1A.105 protein described in WO 2007/140256 (SEQ ID No. 7) or a toxic fragment thereof, the VIP3Aa19 protein of NCBI accession ABG20428, the VIP3Aa20 protein of NCBI accession ABG20429 (SEQ ID No. 2 in WO 2007/142840), the VIP3A proteins produced in the COT202 or COT203 cotton events (WO2005/054479 and WO2005/054480, respectively), the Cry proteins as described in WO2001/47952, the VIP3Aa protein or a toxic fragment thereof as described in Estruch et al. (1996), Proc Natl Acad Sci USA. 28; 93(11):5389-94 and U.S. Pat. No. 6,291,156, the insecticidal proteins from Xenorhabdus (as described in WO98/50427), Serratia (particularly from *S. entomophila*) or Photorhabdus species strains, such as Tc-proteins from Photorhabdus as described in WO98/08932 (e.g., Waterfield et al., 2001, Appl Environ Microbiol. 67(11):5017-24; Ffrench-Constant and Bowen, 2000, Cell Mol Life Sci.; 57(5):828-33). Also any variants or mutants of any one of these proteins differing in some (1-10, preferably 1-5) amino acids from any of the above sequences, particularly the sequence of their toxic fragment, or which are fused to a transit peptide, such as a plastid transit peptide, or another protein or peptide, is included herein.

In yet another embodiment, the sequences encompassed herein are MTX-like sequences. The term "MTX" is used in the art to delineate a set of pesticidal proteins that are produced by *Bacillus sphaericus*. The first of these, often referred to in the art as MTX1, is synthesized as a parasporal crystal which is toxic to mosquitoes. The major components of the crystal are two proteins of 51 and 42 kDa, Since the presence of both proteins are required for toxicity, MTX1 is considered a "binary" toxin (Baumann et al. (1991) Microbiol. Rev. 55:425-436).

By analysis of different *Bacillus sphaericus* strains with differing toxicities, two new classes of MTX toxins have been identified. MTX2 and MTX3 represent separate, related classes of pesticidal toxins that exhibit pesticidal activity. See, for example, Baumann et al. (1991) Microbiol. Rev. 55:425-436, herein incorporated by reference in its entirety. MTX2 is a 100-kDa toxin. More recently MTX3 has been identified as a separate toxin, though the amino acid sequence of MTX3 from *B. sphaericus* is 38% identical to the MTX2 toxin of *B. sphaericus* SSII-1 (Liu, et al. (1996) Appl. Environ. Microbiol. 62: 2174-2176). Mtx toxins may be useful for both increasing the insecticidal activity of *B. sphaericus* strains and managing the evolution of resistance to the Bin toxins in mosquito populations (Wirth et al. (2007) Appl Environ Microbiol 73(19):6066-6071).

In various embodiments, the MTX-like sequences include the nucleotide sequences set forth in SEQ ID Nos: 1-15, the amino acid sequences set forth in SEQ ID Nos: 16-30, and biologically-active variants and fragments thereof.

In various embodiments, the nucleic acid of the invention can be combined in plants with one or more genes conferring a desirable trait, such as herbicide tolerance, insect tolerance, drought tolerance, nematode control, water use efficiency, nitrogen use efficiency, improved nutritional value, disease resistance, improved photosynthesis, improved fiber quality, stress tolerance, improved reproduction, and the like.

Particularly useful transgenic events which may be combined with the genes of the current invention in plants of the same species (e.g., by crossing or by re-transforming a plant containing another transgenic event with a chimeric gene of the invention), include Event 531/PV-GHBK04 (cotton, insect control, described in WO2002/040677), Event 1143-14A (cotton, insect control, not deposited, described in WO2006/128569); Event 1143-51B (cotton, insect control, not deposited, described in WO2006/128570); Event 1445 (cotton, herbicide tolerance, not deposited, described in US-A 2002-120964 or WO2002/034946 Event 17053 (rice, herbicide tolerance, deposited as PTA-9843, described in WO2010/117737); Event 17314 (rice, herbicide tolerance, deposited as PTA-9844, described in WO2010/117735); Event 281-24-236 (cotton, insect control—herbicide tolerance, deposited as PTA-6233, described in WO2005/103266 or US-A 2005-216969); Event 3006-210-23 (cotton, insect control—herbicide tolerance, deposited as PTA-6233, described in US-A 2007-143876 or WO2005/103266); Event 3272 (corn, quality trait, deposited as PTA-9972, described in WO2006/098952 or US-A 2006-230473); Event 33391 (wheat, herbicide tolerance, deposited as PTA-2347, described in WO2002/027004), Event 40416 (corn, insect control—herbicide tolerance, deposited as ATCC PTA-11508, described in WO 11/075593); Event 43A47 (corn, insect control—herbicide tolerance, deposited as ATCC PTA-11509, described in WO2011/075595); Event 5307 (corn, insect control, deposited as ATCC PTA-9561, described in WO2010/077816); Event ASR-368 (bent grass, herbicide tolerance, deposited as ATCC PTA-4816, described in US-A 2006-162007 or WO2004/053062); Event B16 (corn, herbicide tolerance, not deposited, described in US-A 2003-126634); Event BPS-CV127-9 (soybean, herbicide tolerance, deposited as NCIMB No. 41603, described in WO2010/080829); Event BLR1 (oilseed rape, restoration of male sterility, deposited as NCIMB 41193, described in WO2005/074671), Event CE43-67B (cotton, insect control, deposited as DSM ACC2724, described in US-A 2009-217423 or WO2006/128573); Event CE44-69D (cotton, insect control, not deposited, described in US-A 2010-0024077); Event CE44-69D (cotton, insect control, not deposited, described in WO2006/128571); Event CE46-02A (cotton, insect control, not deposited, described in WO2006/128572); Event COT102 (cotton, insect control, not deposited, described in US-A 2006-130175 or WO2004/039986); Event COT202 (cotton, insect control, not deposited, described in US-A 2007-067868 or WO2005/054479); Event COT203 (cotton, insect control, not deposited, described in WO2005/054480)); Event DAS21606-3/1606 (soybean, herbicide tolerance, deposited as PTA-11028, described in WO2012/033794), Event DAS40278 (corn, herbicide tolerance, deposited as ATCC PTA-10244, described in WO2011/022469); Event DAS-44406-6/pDAB8264.44.06.1 (soybean, herbicide tolerance, deposited as PTA-11336, described in WO2012/075426), Event DAS-14536-7/pDAB8291.45.36.2 (soybean, herbicide tolerance, deposited as PTA-11335, described in WO2012/075429), Event DAS-59122-7 (corn, insect control—herbicide tolerance, deposited as ATCC PTA 11384, described in US-A 2006-070139); Event DAS-59132 (corn, insect control—herbicide tolerance, not deposited, described in WO2009/100188); Event DAS68416 (soybean, herbicide tolerance, deposited as ATCC PTA-10442, described in WO2011/066384 or WO2011/066360); Event DP-098140-6 (corn, herbicide tolerance, deposited as ATCC PTA-8296, described in US-A 2009-137395 or WO 08/112019); Event DP-305423-1 (soybean, quality trait, not deposited, described in US-A 2008-312082 or WO2008/054747); Event DP-32138-1 (corn, hybridization system, deposited as ATCC PTA-9158, described in US-A 2009-0210970 or WO2009/103049); Event DP-356043-5 (soybean, herbicide tolerance, deposited as ATCC PTA-8287, described in US-A 2010-0184079 or WO2008/002872); Event EE-1 (brinjal, insect control, not deposited, described in WO 07/091277); Event FI117 (corn, herbicide tolerance, deposited as ATCC 209031, described in US-A 2006-059581 or WO 98/044140); Event FG72 (soybean, herbicide tolerance, deposited as PTA-11041, described in WO2011/063413), Event GA21 (corn, herbicide tolerance, deposited as ATCC 209033, described in US-A 2005-086719 or WO 98/044140); Event GG25 (corn, herbicide tolerance, deposited as ATCC 209032, described in US-A 2005-188434 or WO 98/044140); Event GHB119 (cotton, insect control—herbicide tolerance, deposited as ATCC PTA-8398, described in WO2008/151780); Event GHB614 (cotton, herbicide tolerance, deposited as ATCC PTA-6878, described in US-A 2010-050282 or WO2007/017186); Event GJ11 (corn, herbicide tolerance, deposited as ATCC 209030, described in US-A 2005-188434 or WO98/044140); Event GM RZ13 (sugar beet, virus resistance, deposited as NCIMB-41601, described in WO2010/076212); Event H7-1 (sugar beet, herbicide tolerance, deposited as NCIMB 41158 or NCIMB 41159, described in US-A 2004-172669 or WO 2004/074492); Event JOPLIN1 (wheat, disease tolerance, not deposited, described in US-A 2008-064032); Event LL27 (soybean, herbicide tolerance, deposited as NCIMB41658, described in WO2006/108674 or US-A 2008-320616); Event LL55 (soybean, herbicide tolerance, deposited as NCIMB 41660, described in WO 2006/108675 or US-A 2008-196127); Event LLcotton25 (cotton, herbicide tolerance, deposited as ATCC PTA-3343, described in WO2003/013224 or US-A 2003-097687); Event LLRICE06 (rice, herbicide tolerance, deposited as ATCC 203353, described in U.S. Pat. No. 6,468,747 or WO2000/026345); Event LLRice62 (rice, herbicide tolerance, deposited as ATCC 203352, described in WO2000/026345), Event LLRICE601 (rice, herbicide tolerance, deposited as ATCC PTA-2600, described in US-A 2008-2289060 or WO2000/026356); Event LY038 (corn, quality trait, deposited as ATCC PTA-5623, described in US-A 2007-028322 or WO2005/061720); Event MIR162 (corn, insect control, deposited as PTA-8166, described in US-A 2009-300784 or WO2007/142840); Event MIR604 (corn, insect control, not deposited, described in US-A 2008-167456 or WO2005/103301); Event MON15985 (cotton, insect control, deposited as ATCC PTA-2516, described in US-A 2004-250317 or WO2002/100163); Event MON810 (corn, insect control, not deposited, described in US-A 2002-102582); Event MON863 (corn, insect control, deposited as ATCC PTA-2605, described in WO2004/011601 or US-A 2006-095986); Event MON87427 (corn, pollination control, deposited as ATCC PTA-7899, described in WO2011/062904); Event MON87460 (corn, stress tolerance, deposited as ATCC PTA-8910, described in WO2009/111263 or US-A 2011-0138504); Event MON87701 (soybean, insect control, deposited as ATCC PTA-8194, described in US-A 2009-130071 or WO2009/064652); Event MON87705 (soybean, quality trait—herbicide tolerance, deposited as ATCC PTA-9241, described in US-A 2010-0080887 or WO2010/037016); Event MON87708 (soybean, herbicide tolerance, deposited as ATCC PTA-9670, described in WO2011/034704); Event MON87712 (soybean, yield, deposited as PTA-10296, described in WO2012/051199), Event MON87754 (soybean, quality trait, deposited as ATCC PTA-9385, described in WO2010/024976); Event MON87769 (soybean, quality trait, deposited as ATCC PTA-8911, described in US-A 2011-0067141 or WO2009/102873); Event MON88017 (corn, insect control—herbicide tolerance, deposited as ATCC PTA-5582, described in US-A 2008-028482 or WO2005/059103); Event MON88913 (cotton, herbicide tolerance, deposited as ATCC PTA-4854, described in WO2004/072235 or US-A 2006-059590); Event MON88302 (oilseed rape, herbicide tolerance, deposited as PTA-10955, described in WO2011/153186), Event MON88701 (cotton, herbicide tolerance, deposited as PTA-11754, described in WO2012/134808), Event MON89034 (corn, insect control, deposited as ATCC PTA-7455, described in WO 07/140256 or US-A 2008-260932); Event MON89788 (soybean, herbicide tolerance, deposited as ATCC PTA-6708, described in US-A 2006-282915 or WO2006/130436); Event MS11 (oilseed rape, pollination control—herbicide tolerance, deposited as ATCC PTA-850 or PTA-2485, described in WO2001/031042); Event MS8 (oilseed rape, pollination control—herbicide tolerance, deposited as ATCC PTA-730, described in WO2001/041558 or US-A 2003-188347); Event NK603 (corn, herbicide tolerance, deposited as ATCC PTA-2478, described in US-A 2007-292854); Event PE-7 (rice, insect control, not deposited, described in WO2008/114282); Event RF3 (oilseed rape, pollination control—herbicide tolerance, deposited as ATCC PTA-730, described in WO2001/041558 or US-A 2003-188347); Event RT73 (oilseed rape, herbicide tolerance, not deposited, described in WO2002/036831 or US-A 2008-070260); Event SYHT0H2/SYN-000H2-5 (soybean, herbicide tolerance, deposited as PTA-11226, described in WO2012/082548), Event T227-1 (sugar beet, herbicide tolerance, not deposited, described in WO2002/44407 or US-A 2009-265817); Event T25 (corn, herbicide tolerance, not deposited, described in US-A 2001-029014 or WO2001/051654); Event T304-40 (cotton, insect control-herbicide tolerance, deposited as ATCC PTA-8171, described in US-A 2010-077501 or WO2008/122406); Event T342-142 (cotton, insect control, not deposited, described in WO2006/128568); Event TC1507 (corn, insect control—herbicide tolerance, not deposited, described in US-A 2005-039226 or WO2004/099447); Event VIP1034 (corn, insect control—herbicide tolerance, deposited as ATCC PTA-3925, described in WO2003/052073), Event 32316 (corn, insect control—herbicide tolerance, deposited as PTA-11507, described in WO2011/084632), Event 4114 (corn, insect control—herbicide tolerance, deposited as PTA-11506, described in WO2011/084621), event EE-GM3/FG72 (soybean, herbicide tolerance, ATCC Accession No PTA-11041) optionally stacked with event EE-GM1/LL27 or event EE-GM2/LL55 (WO2011/063413A2), event DAS-68416-4 (soybean, herbicide tolerance, ATCC Accession No PTA-10442, WO2011/066360A1), event DAS-68416-4 (soybean, herbicide tolerance, ATCC Accession No PTA-10442, WO2011/066384A1), event DP-040416-8 (corn, insect control, ATCC Accession No PTA-11508, WO2011/075593A1), event DP-043A47-3 (corn, insect control, ATCC Accession No PTA-11509, WO2011/075595A1), event DP-004114-3 (corn, insect control, ATCC Accession No PTA-11506, WO2011/084621A1), event DP-032316-8 (corn, insect control, ATCC Accession No PTA-11507, WO2011/084632A1), event MON-88302-9 (oilseed rape, herbicide tolerance, ATCC Accession No PTA-10955, WO2011/153186A1), event DAS-21606-3 (soybean, herbicide tolerance, ATCC Accession No. PTA-11028, WO2012/033794A2), event MON-87712-4 (soybean, quality trait, ATCC Accession No. PTA-10296, WO2012/051199A2), event DAS-44406-6 (soybean, stacked herbicide tolerance, ATCC Accession No. PTA-11336, WO2012/075426A1), event DAS-14536-7 (soybean, stacked herbicide tolerance, ATCC Accession No.

PTA-11335, WO2012/075429A1), event SYN-000H2-5 (soybean, herbicide tolerance, ATCC Accession No. PTA-11226, WO2012/082548A2), event DP-061061-7 (oilseed rape, herbicide tolerance, no deposit No available, WO2012071039A1), event DP-073496-4 (oilseed rape, herbicide tolerance, no deposit No available, US2012131692), event 8264.44.06.1 (soybean, stacked herbicide tolerance, Accession No PTA-11336, WO2012075426A2), event 8291.45.36.2 (soybean, stacked herbicide tolerance, Accession No. PTA-11335, WO2012075429A2), event SYHT0H2 (soybean, ATCC Accession No. PTA-11226, WO2012/082548A2), event MON88701 (cotton, ATCC Accession No PTA-11754, WO2012/134808A1), event KK179-2 (alfalfa, ATCC Accession No PTA-11833, WO2013/003558A1), event pDAB8264.42.32.1 (soybean, stacked herbicide tolerance, ATCC Accession No PTA-11993, WO2013/010094A1), event MZDT09Y (corn, ATCC Accession No PTA-13025, WO2013/012775A1).

Transformation of plant cells can be accomplished by one of several techniques known in the art. The pesticidal gene of the invention may be modified to obtain or enhance expression in plant cells. Typically, a construct that expresses such a protein would contain a promoter to drive transcription of the gene, as well as a 3' untranslated region to allow transcription termination and polyadenylation. The organization of such constructs is well known in the art. In some instances, it may be useful to engineer the gene such that the resulting peptide is secreted, or otherwise targeted within the plant cell. For example, the gene can be engineered to contain a signal peptide to facilitate transfer of the peptide to the endoplasmic reticulum. It may also be preferable to engineer the plant expression cassette to contain an intron, such that mRNA processing of the intron is required for expression.

Typically, this "plant expression cassette" will be inserted into a "plant transformation vector". This plant transformation vector may be comprised of one or more DNA vectors needed for achieving plant transformation. For example, it is a common practice in the art to utilize plant transformation vectors that are comprised of more than one contiguous DNA segment. These vectors are often referred to in the art as "binary vectors." Binary vectors as well as vectors with helper plasmids are most often used for Agrobacterium-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the pesticidal gene are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux (2000) *Trends in Plant Science* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into a mature plant and produces fertile seeds (e.g. Hiei et al. (1994) *The Plant Journal* 6:271-282; Ishida et al. (1996) *Nature Biotechnology* 14:745-750). Explants are typically transferred to a fresh supply of the same medium and cultured routinely. A general description of the techniques and methods for generating transgenic plants are found in Ayres and Park (1994) *Critical Reviews in Plant Science* 13:219-239 and Bommineni and Jauhar (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

Transformation protocols as well as protocols for introducing nucleotide sequences into plants may vary depending on the type of plant or plant cell, i.e., monocot or dicot, targeted for transformation. Generation of transgenic plants may be performed by one of several methods, including, but not limited to, microinjection, electroporation, direct gene transfer, introduction of heterologous DNA by *Agrobacterium* into plant cells (*Agrobacterium*-mediated transformation), bombardment of plant cells with heterologous foreign DNA adhered to particles, ballistic particle acceleration, aerosol beam transformation (U.S. Published Application No. 20010026941; U.S. Pat. No. 4,945,050; International Publication No. WO 91/00915; U.S. Published Application No. 2002015066), Lec1 transformation, and various other non-particle direct-mediated methods to transfer DNA.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

Following integration of heterologous foreign DNA into plant cells, one then applies a maximum threshold level of appropriate selection in the medium to kill the untransformed cells and separate and proliferate the putatively transformed cells that survive from this selection treatment by transferring regularly to a fresh medium. By continuous passage and challenge with appropriate selection, one identifies and proliferates the cells that are transformed with the plasmid vector. Molecular and biochemical methods can then be used to confirm the presence of the integrated heterologous gene of interest into the genome of the transgenic plant.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

Evaluation of Plant Transformation

Following introduction of heterologous foreign DNA into plant cells, the transformation or integration of heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell (2001) *Molecular Cloning: A Laboratory Manual*. Cold Spring Harbor Laboratory Press, Cold Spring Harbor, NY). PCR is carried out using oligonucleotide primers specific to the gene of interest or *Agrobacterium* vector background, etc.

Plant transformation may be confirmed by Southern blot analysis of genomic DNA (Sambrook and Russell, 2001, supra). In general, total DNA is extracted from the transformant, digested with appropriate restriction enzymes, fractionated in an agarose gel and transferred to a nitrocellulose or nylon membrane. The membrane or "blot" is then probed with, for example, radiolabeled $^{32}P$ target DNA fragment to confirm the integration of introduced gene into the plant genome according to standard techniques (Sambrook and Russell, 2001, supra).

In Northern blot analysis, RNA is isolated from specific tissues of transformant, fractionated in a formaldehyde agarose gel, and blotted onto a nylon filter according to standard procedures that are routinely used in the art (Sambrook and Russell, 2001, supra). Expression of RNA encoded by the pesticidal gene is then tested by hybridizing the filter to a radioactive probe derived from a pesticidal gene, by methods known in the art (Sambrook and Russell, 2001, supra).

Western blot, biochemical assays and the like may be carried out on the transgenic plants to confirm the presence of protein encoded by the pesticidal gene by standard procedures (Sambrook and Russell, 2001, supra) using antibodies that bind to one or more epitopes present on the pesticidal protein.

Pesticidal Activity in Plants

In another aspect of the invention, one may generate transgenic plants expressing a pesticidal protein that has pesticidal activity. Methods described above by way of example may be utilized to generate transgenic plants, but the manner in which the transgenic plant cells are generated is not critical to this invention. Methods known or described in the art such as *Agrobacterium*-mediated transformation, biolistic transformation, and non-particle-mediated methods may be used at the discretion of the experimenter. Plants expressing a pesticidal protein may be isolated by common methods described in the art, for example by transformation of callus, selection of transformed callus, and regeneration of fertile plants from such transgenic callus. In such process, one may use any gene as a selectable marker so long as its expression in plant cells confers ability to identify or select for transformed cells.

A number of markers have been developed for use with plant cells, such as resistance to chloramphenicol, the aminoglycoside G418, hygromycin, or the like. Other genes that encode a product involved in chloroplast metabolism may also be used as selectable markers. For example, genes that provide resistance to plant herbicides such as glyphosate, bromoxynil, or imidazolinone may find particular use. Such genes have been reported (Stalker et al. (1985) *J. Biol. Chem.* 263:6310-6314 (bromoxynil resistance nitrilase gene); and Sathasivan et al. (1990) *Nucl. Acids Res.* 18:2188 (AHAS imidazolinone resistance gene). Additionally, the genes disclosed herein are useful as markers to assess transformation of bacterial or plant cells. Methods for detecting the presence of a transgene in a plant, plant organ (e.g., leaves, stems, roots, etc.), seed, plant cell, propagule, embryo or progeny of the same are well known in the art. In one embodiment, the presence of the transgene is detected by testing for pesticidal activity.

Fertile plants expressing a pesticidal protein may be tested for pesticidal activity, and the plants showing optimal activity selected for further breeding. Methods are available in the art to assay for pest activity. Generally, the protein is mixed and used in feeding assays. See, for example Marrone et al. (1985) *J. of Economic Entomology* 78:290-293.

The present invention may be used for transformation of any plant species, including, but not limited to, monocots and dicots. Examples of plants of interest include, but are not limited to, corn (maize), *Sorghum*, wheat, sunflower, tomato, crucifers, peppers, potato, cotton, rice, soybean, sugar beet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, *papaya*, cashew, macadamia, almond, oats, vegetables, ornamentals, and conifers.

Vegetables include, but are not limited to, tomatoes, lettuce, green beans, lima beans, peas, and members of the genus *Curcumis* such as cucumber, cantaloupe, and musk melon. Ornamentals include, but are not limited to, azalea, *hydrangea*, hibiscus, roses, tulips, daffodils, petunias, carnation, poinsettia, and *chrysanthemum*. Preferably, plants of the present invention are crop plants (for example, maize, *Sorghum*, wheat, sunflower, tomato, crucifers, peppers, potato, cotton, rice, soybean, sugar beet, sugarcane, tobacco, barley, oilseed rape, etc.).

Use in Pesticidal Control

General methods for employing strains comprising a nucleotide sequence of the present invention, or a variant thereof, in pest control or in engineering other organisms as pesticidal agents are known in the art. See, for example U.S. Pat. No. 5,039,523 and EP 0480762A2.

The *Bacillus* strains containing a nucleotide sequence of the present invention, or a variant thereof, or the microorganisms that have been genetically altered to contain a pesticidal gene of the invention and protein may be used for protecting agricultural crops and products from pests. In one aspect of the invention, whole, i.e., unlysed, cells of a toxin (pesticide)-producing organism are treated with reagents that prolong the activity of the toxin produced in the cell when the cell is applied to the environment of target pest(s).

Alternatively, the pesticide is produced by introducing a pesticidal gene into a cellular host. Expression of the pesticidal gene results, directly or indirectly, in the intracellular production and maintenance of the pesticide. In one aspect of this invention, these cells are then treated under conditions that prolong the activity of the toxin produced in the cell when the cell is applied to the environment of the target pest(s). The resulting product retains the toxicity of the toxin. These naturally encapsulated pesticides may then be formulated in accordance with conventional techniques for application to the environment hosting a target pest, e.g., soil, water, and foliage of plants. See, for example EPA 0192319, and the references cited therein. Alternatively, one may formulate the cells expressing a gene of this invention such as to allow application of the resulting material as a pesticide.

The active ingredients of the present invention are normally applied in the form of compositions and can be applied to the crop area or plant to be treated, simultaneously or in succession, with other compounds. These compounds can be fertilizers, weed killers, cryoprotectants, surfactants, detergents, pesticidal soaps, dormant oils, polymers, and/or time-release or biodegradable carrier formulations that permit long-term dosing of a target area following a single application of the formulation. They can also be selective herbicides, chemical insecticides, virucides, microbicides, amoebicides, pesticides, fungicides, bacteriocides, nematocides, molluscicides or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. Likewise, the formulations may be prepared into edible "baits" or fashioned into pest "traps" to permit feeding or ingestion by a target pest of the pesticidal formulation.

Methods of applying an active ingredient of the present invention or an agrochemical composition of the present invention that contains at least one of the pesticidal proteins produced by the bacterial strains of the present invention include leaf application, seed coating and soil application. The number of applications and the rate of application depend on the intensity of infestation by the corresponding pest.

The composition may be formulated as a powder, dust, pellet, granule, spray, emulsion, colloid, solution, or such like, and may be prepared by such conventional means as desiccation, lyophilization, homogenation, extraction, filtration, centrifugation, sedimentation, or concentration of a culture of cells comprising the polypeptide. In all such compositions that contain at least one such pesticidal polypeptide, the polypeptide may be present in a concentration of from about 1% to about 99% by weight.

Lepidopteran, hemipteran, dipteran, or coleopteran pests may be killed or reduced in numbers in a given area by the methods of the invention or may be prophylactically applied to an environmental area to prevent infestation by a susceptible pest. Preferably the pest ingests, or is contacted with, a pesticidally-effective amount of the polypeptide. By "pesticidally-effective amount" is intended an amount of the pesticide that is able to bring about death to at least one pest, or to noticeably reduce pest growth, feeding, or normal physiological development. For example, the pesticide may result in reduced egg hatching, mortality at any stage of development of the insect, reduced molting, and/or reduced feeding of the pest on a target organisms (e.g., reduced number of feeding sites a plant or plant cell and/or reduced damage to a plant or plant cell). This amount will vary depending on such factors as, for example, the specific target pests to be controlled, the specific environment, location, plant, crop, or agricultural site to be treated, the environmental conditions, and the method, rate, concentration, stability, and quantity of application of the pesticidally-effective polypeptide composition. The formulations may also vary with respect to climatic conditions, environmental considerations, and/or frequency of application and/or severity of pest infestation.

The pesticide compositions described may be made by formulating either the bacterial cell, the crystal and/or the spore suspension, or the isolated protein component with the desired agriculturally-acceptable carrier. The compositions may be formulated prior to administration in an appropriate means such as lyophilized, freeze-dried, desiccated, or in an aqueous carrier, medium or suitable diluent, such as saline or other buffer. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term "agriculturally-acceptable carrier" covers all adjuvants, inert components, dispersants, surfactants, tackifiers, binders, etc. that are ordinarily used in pesticide formulation technology; these are well known to those skilled in pesticide formulation. The formulations may be mixed with one or more solid or liquid adjuvants and prepared by various means, e.g., by homogeneously mixing, blending and/or grinding the pesticidal composition with suitable adjuvants using conventional formulation techniques. Suitable formulations and application methods are described in U.S. Pat. No. 6,468,523, herein incorporated by reference.

"Pest" includes but is not limited to, insects, fungi, bacteria, nematodes, mites, ticks, and the like. Insect pests include insects selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc., particularly Coleoptera, Lepidoptera, and Diptera.

The order Coleoptera includes the suborders Adephaga and Polyphaga. Suborder Adephaga includes the superfamilies Caraboidea and Gyrinoidea, while suborder Polyphaga includes the superfamilies Hydrophiloidea, Staphylinoidea, Cantharoidea, Cleroidea, Elateroidea, Dascilloidea, Dryopoidea, Byrrhoidea, Cucujoidea, Meloidea, Mordelloidea, Tenebrionoidea, Bostrichoidea, Scarabaeoidea, Cerambycoidea, Chrysomeloidea, and Curculionoidea. Superfamily Caraboidea includes the families Cicindelidae, Carabidae, and Dytiscidae. Superfamily Gyrinoidea includes the family Gyrinidae. Superfamily Hydrophiloidea includes the family Hydrophilidae. Superfamily Staphylinoidea includes the families Silphidae and Staphylinidae. Superfamily Cantharoidea includes the families Cantharidae and Lampyridae. Superfamily Cleroidea includes the families Cleridae and Dermestidae. Superfamily Elateroidea includes the families Elateridae and Buprestidae. Superfamily Cucujoidea includes the family Coccinellidae. Superfamily Meloidea includes the family Meloidae. Superfamily Tenebrionoidea includes the family Tenebrionidae. Superfamily Scarabaeoidea includes the families Passalidae and Scarabaeidae. Superfamily Cerambycoidea includes the family Cerambycidae. Superfamily Chrysomeloidea includes the family Chrysomelidae. Superfamily Curculionoidea includes the families Curculionidae and Scolytidae.

The order Diptera includes the Suborders Nematocera, Brachycera, and Cyclorrhapha. Suborder Nematocera includes the families Tipulidae, Psychodidae, Culicidae, Ceratopogonidae, Chironomidae, Simuliidae, Bibionidae, and Cecidomyiidae. Suborder Brachycera includes the families Stratiomyidae, Tabanidae, Therevidae, Asilidae, Mydidae, Bombyliidae, and Dolichopodidae. Suborder Cyclorrhapha includes the Divisions Aschiza and Aschiza. Division Aschiza includes the families Phoridae, Syrphidae, and Conopidae. Division Aschiza includes the Sections Acalyptratae and Calyptratae. Section Acalyptratae includes the families Otitidae, Tephritidae, Agromyzidae, and Drosophilidae. Section Calyptratae includes the families Hippoboscidae, Oestridae, Tachinidae, Anthomyiidae, Muscidae, Calliphoridae, and Sarcophagidae.

The order Lepidoptera includes the families Papilionidae, Pieridae, Lycaenidae, Nymphalidae, Danaidae, Satyridae, Hesperiidae, Sphingidae, Saturniidae, Geometridae, Arctiidae, Noctuidae, Lymantriidae, Sesiidae, and Tineidae.

Nematodes include parasitic nematodes such as root-knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include *Pratylenchus* spp.

Hemipteran pests (which include species that are designated as Hemiptera, Homoptera, or Heteroptera) include, but are not limited to, *Lygus* spp., such as Western tarnished plant bug (*Lygus hesperus*), the tarnished plant bug (*Lygus lineolaris*), and green plant bug (*Lygus elisus*); aphids, such as the green peach aphid (*Myzus persicae*), cotton aphid (*Aphis gossypii*), cherry aphid or black cherry aphid (*Myzus cerasi*), soybean aphid (*Aphis glycines* Matsumura); brown plant hopper (*Nilaparvata lugens*), and rice green leafhopper (*Nephotettix* spp.); and stink bugs, such as green stink bug (*Acrosternum hilare*), brown marmorated stink bug (*Halyomorpha halys*), southern green stink bug (*Nezara viridula*), rice stink bug (*Oebalus pugnax*), forest bug (*Pentatoma rufipes*), European stink bug (*Rhaphigaster nebulosa*), and the shield bug *Troilus luridus*.

Insect pests of the invention for the major crops include: Maize: *Ostrinia nubilalis*, European corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, surgarcane borer; *Diabrotica virgifera*, western corn rootworm; *Diabrotica longicornis barberi*, northern corn rootworm; *Diabrotica undecimpunctata howardi*, southern corn rootworm; *Melanotus* spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blot leafminer; *Anaphothrips obscrurus*, grass Thrips; *Solenopsis milesta*, thief ant; *Tetranychus urticae*, twospotted spider mite; Sorghum: *Chilo partellus*, Sorghum borer; *Spodoptera frugiperda*, fall armyworm; *Spodoptera cosmioides*; *Spodoptera eridania*; *Helicoverpa zea*, corn earworm; *Elasmopalpus lignosellus*, lesser cornstalk borer; *Feltia subterranea*, granulate cutworm; *Phyllophaga crinita*, white grub; *Eleodes, Conoderus,* and *Aeolus* spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus leucopterus*, chinch bug; *Contarinia sorghicola*, Sorghum midge; *Tetranychus cinnabarinus*, carmine spider mite; *Tetranychus urticae*, twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco Thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *Zygogramma exclamationis*, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion Thrips; *Franklinkiella fusca*, tobacco Thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Spodoptera cosmioides*; *Spodoptera eridania*; *Helicoverpa zea*, corn earworm; *Colaspis brunnea*, grape *Colaspis*; *Lissorhoptrus oryzophilus*, rice water weevil; *Sitophilus oryzae*, rice weevil; *Nephotettix nigropictus*, rice leafhopper; *Blissus leucopterus leucopterus*, chinch bug; *Acrosternum hilare*, green stink bug; *Chilu suppressalis*, Asiatic rice borer; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Spodoptera cosmioides*; *Spodoptera eridania*; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean Thrips; *Thrips tabaci*, onion Thrips; *Tetranychus turkestani*, strawberry spider mite; *Tetranychus urticae*, twospotted spider mite; Barley: *Ostrinia nubilalis*, European corn borer; *Agro-*

*tis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Euschistus heros*, neotropical brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; *Delia* ssp., Root maggots.

Methods for Increasing Plant Yield

Methods for increasing plant yield are provided. The methods comprise providing a plant or plant cell expressing a polynucleotide encoding the pesticidal polypeptide sequence disclosed herein and growing the plant or a seed thereof in a field infested with (or susceptible to infestation by) a pest against which said polypeptide has pesticidal activity. In some embodiments, the polypeptide has pesticidal activity against a lepidopteran, coleopteran, dipteran, hemipteran, or nematode pest, and said field is infested with a lepidopteran, hemipteran, coleopteran, dipteran, or nematode pest. As defined herein, the "yield" of the plant refers to the quality and/or quantity of biomass produced by the plant. By "biomass" is intended any measured plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase in yield compared to a plant not expressing the pesticidal sequence. In specific methods, plant yield is increased as a result of improved pest resistance of a plant expressing a pesticidal protein disclosed herein. Expression of the pesticidal protein results in a reduced ability of a pest to infest or feed.

The plants can also be treated with one or more chemical compositions, including one or more herbicide, insecticides, or fungicides. Exemplary chemical compositions include: Fruits/Vegetables Herbicides: Atrazine, Bromacil, Diuron, Glyphosate, Linuron, Metribuzin, Simazine, Trifluralin, Fluazifop, Glufosinate, Halosulfuron Gowan, Paraquat, Propyzamide, Sethoxydim, Butafenacil, Halosulfuron, Indaziflam; Fruits/Vegetables Insecticides: Aldicarb, *Bacillus thuringiensis*, Carbaryl, Carbofuran, Chlorpyrifos, Cypermethrin, Deltamethrin, Abamectin, Cyfluthrin/beta-cyfluthrin, Esfenvalerate, Lambda-cyhalothrin, Acequinocyl, Bifenazate, Methoxyfenozide, Novaluron, Chromafenozide, Thiacloprid, Dinotefuran, Fluacrypyrim, Spirodiclofen, Gamma-cyhalothrin, Spiromesifen, Spinosad, Rynaxypyr, Cyazypyr, Triflumuron, Spirotetramat, Imidacloprid, Flubendiamide, Thiodicarb, Metaflumizone, Sulfoxaflor, Cyflumetofen, Cyanopyrafen, Clothianidin, Thiamethoxam, Spinotoram, Thiodicarb, Flonicamid, Methiocarb, Emamectin-benzoate, Indoxacarb, Fenamiphos, Pyriproxifen, Fenbutatin-oxid; Fruits/Vegetables Fungicides: Ametoctradin, Azoxystrobin, Benthiavalicarb, Boscalid, Captan, Carbendazim, Chlorothalonil, Copper, Cyazofamid, Cyflufenamid, Cymoxanil, Cyproconazole, Cyprodinil, Difenoconazole, Dimetomorph, Dithianon, Fenamidone, Fenhexamid, Fluazinam, Fludioxonil, Fluopicolide, Fluopyram, Fluoxastrobin, Fluxapyroxad, Folpet, Fosetyl, Iprodione, Iprovalicarb, Isopyrazam, Kresoxim-methyl, Mancozeb, Mandipropamid, Metalaxyl/mefenoxam, Metiram, Metrafenone, Myclobutanil, Penconazole, Penthiopyrad, Picoxystrobin, Propamocarb, Propiconazole, Propineb, Proquinazid, Prothioconazole, Pyraclostrobin, Pyrimethanil, Quinoxyfen, Spiroxamine, Sulphur, Tebuconazole, Thiophanate-methyl, Trifloxystrobin; Cereals Herbicides: 2.4-D, Amidosulfuron, Bromoxynil, Carfentrazone-E, Chlorotoluron, Chlorsulfuron, Clodinafop-P, Clopyralid, Dicamba, Diclofop-M, Diflufenican, Fenoxaprop, Florasulam, Flucarbazone-NA, Flufenacet, Flupyrosulfuron-M, Fluroxypyr, Flurtamone, Glyphosate, Iodosulfuron, Ioxynil, Isoproturon, MCPA, Mesosulfuron, Metsulfuron, Pendimethalin, Pinoxaden, Propoxycarbazone, Prosulfocarb, Pyroxsulam, Sulfosulfuron, Thifensulfuron, Tralkoxydim, Triasulfuron, Tribenuron, Trifluralin, Tritosulfuron; Cereals Fungicides: Azoxystrobin, Bixafen, Boscalid, Carbendazim, Chlorothalonil, Cyflufenamid, Cyproconazole, Cyprodinil, Dimoxystrobin, Epoxiconazole, Fenpropidin, Fenpropimorph, Fluopyram, Fluoxastrobin, Fluquinconazole, Fluxapyroxad, Isopyrazam, Kresoxim-methyl, Metconazole, Metrafenone, Penthiopyrad, Picoxystrobin, Prochloraz, Propiconazole, Proquinazid, Prothioconazole, Pyraclostrobin, Quinoxyfen, Spiroxamine, Tebuconazole, Thiophanate-methyl, Trifloxystrobin; Cereals Insecticides: Dimethoate, Lambda-cyhalothrin, Deltamethrin, alpha-Cypermethrin, β-cyfluthrin, Bifenthrin, Imidacloprid, Clothianidin, Thiamethoxam, Thiacloprid, Acetamiprid, Dinetofuran, Clorphyriphos, Pirimicarb, Methiocarb, Sulfoxaflor; Maize Herbicides: Atrazine, Alachlor, Bromoxynil, Acetochlor, Dicamba, Clopyralid, (S-)Dimethenamid, Glufosinate, Glyphosate, Isoxaflutole, (S-)Metolachlor, Mesotrione, Nicosulfuron, Primisulfuron, Rimsulfuron, Sulcotrione, Foramsulfuron, Topramezone, Tembotrione, Saflufenacil, Thiencarbazone, Flufenacet, Pyroxasulfon; Maize Insecticides: Carbofuran, Chlorpyrifos, Bifenthrin, Fipronil, Imidacloprid, Lambda-Cyhalothrin, Tefluthrin, Terbufos, Thiamethoxam, Clothianidin, Spiromesifen, Flubendiamide, Triflumuron, Rynaxypyr, Deltamethrin, Thiodicarb, β-Cyfluthrin, Cypermethrin, Bifenthrin, Lufenuron, Tebupirimphos, Ethiprole, Cyazypyr, Thiacloprid, Acetamiprid, Dinetofuran, Avermectin; Maize Fungicides: Azoxystrobin, Bixafen, Boscalid, Cyproconazole, Dimoxystrobin, Epoxiconazole, Fenitropan, Fluopyram, Fluoxastrobin, Fluxapyroxad, Isopyrazam, Metconazole, Penthiopyrad, Picoxystrobin, Propiconazole, Prothioconazole, Pyraclostrobin, Tebuconazole, Trifloxystrobin; Rice Herbicides: Butachlor, Propanil, Azimsulfuron, Bensulfuron, Cyhalofop, Daimuron, Fentrazamide, Imazosulfuron, Mefenacet, Oxaziclomefone, Pyrazosulfuron, Pyributicarb, Quinclorac, Thiobencarb, Indanofan, Flufenacet, Fentrazamide, Halosulfuron, Oxaziclomefone, Benzobicyclon, Pyriftalid, Penoxsulam, Bispyribac, Oxadiargyl, Ethoxysulfuron, Pretilachlor, Mesotrione, Tefuryltrione, Oxadiazone, Fenoxaprop, Pyrimisulfan; Rice Insecticides: Diazinon, Fenobucarb, Benfuracarb, Buprofezin, Dinotefuran, Fipronil, Imidacloprid, Isoprocarb, Thiacloprid, Chromafenozide, Clothianidin, Ethiprole, Flubendiamide, Rynaxypyr, Deltamethrin, Acetamiprid, Thiamethoxam, Cyazypyr, Spinosad, Spinotoram, Emamectin-Benzoate, Cypermethrin, Chlorpyriphos, Etofenprox, Carbofuran, Benfuracarb, Sulfoxaflor; Rice Fungicides: Azoxystrobin, Carbendazim, Carpropamid, Diclocymet, Difenoconazole, Edifenphos, Ferimzone, Gentamycin, Hexaconazole, Hymexazol, Iprobenfos (IBP), Isoprothiolane, Isotianil, Kasugamycin, Mancozeb, Metominostrobin, Orysastrobin, Pencycuron, Probenazole, Propiconazole, Propineb, Pyroquilon, Tebuconazole, Thiophanate-methyl, Tiadinil, Tricyclazole, Trifloxystrobin, Validamycin; Cotton Herbicides: Diuron, Fluometuron, MSMA, Oxyfluorfen, Prometryn, Trifluralin, Carfentrazone, Clethodim, Fluazifop-butyl, Glyphosate, Norflurazon, Pendimethalin, Pyrithiobac-sodium, Trifloxysulfuron, Tepraloxydim, Glufosinate, Flumioxazin, Thidiazuron; Cotton Insecticides: Acephate, Aldicarb, Chlorpyrifos, Cypermethrin, Deltamethrin, Abamectin, Acetamiprid, Emamectin Benzoate, Imidacloprid, Indoxacarb, Lambda-Cyhalothrin, Spinosad, Thiodicarb, Gamma-Cyhalothrin, Spiromesifen, Pyridalyl, Flonicamid Flubendiamide, Triflumuron, Rynaxypyr, Beta-Cyfluthrin, Spirotetramat, Clothianidin, Thiamethoxam, Thiacloprid, Dinetofuran, Flubendiamide, Cyazypyr, Spinosad, Spinotoram, gamma Cyhalothrin, 4-[[(6-Chlorpyridin-3-yl)methyl](2,2-difluorethyl)amino]furan-2(5H)-on, Thiodicarb, Avermectin, Flonicamid, Pyridalyl, Spiromesifen, Sulfoxaflor; Cotton Fungicides: Azoxystrobin, Bixafen, Boscalid, Carbendazim, Chlorothalonil, Copper, Cyproconazole, Difenoconazole, Dimoxystrobin, Epoxiconazole, Fenamidone, Fluazinam, Fluopyram, Fluoxastrobin, Fluxapyroxad, Iprodione, Isopyrazam, Isotianil, Mancozeb, Maneb, Metominostrobin, Penthiopyrad, Picoxystrobin, Propineb, Prothioconazole, Pyraclostrobin, Quintozene, Tebuconazole, Tetraconazole, Thiophanate-methyl, Trifloxystrobin; Soybean Herbicides: Alachlor, Bentazone, Trifluralin, Chlorimuron-Ethyl, Cloransulam-Methyl, Fenoxaprop, Fomesafen, Fluazifop, Glyphosate, Imazamox, Imazaquin, Imazethapyr, (S-)Metolachlor, Metribuzin, Pendimethalin, Tepraloxydim, Glufosinate; Soybean Insecticides: Lambda-cyhalothrin, Methomyl, Imidacloprid, Clothianidin, Thiamethoxam, Thiacloprid, Acetamiprid, Dinetofuran, Flubendiamide, Rynaxypyr, Cyazypyr, Spinosad, Spinotoram, Emamectin-Benzoate, Fipronil, Ethiprole, Deltamethrin, β-Cyfluthrin, gamma and lambda Cyhalothrin, 4-[[(6-Chlorpyridin-3-yl)methyl](2,2-difluorethyl)amino]furan-2(5H)-on, Spirotetramat, Spinodiclofen, Triflumuron, Flonicamid, Thiodicarb, beta-Cyfluthrin; Soybean Fungicides: Azoxystrobin, Bixafen, Boscalid, Carbendazim, Chlorothalonil, Copper, Cyproconazole, Difenoconazole, Dimoxystrobin, Epoxiconazole, Fluazinam, Fluopyram, Fluoxastrobin, Flutriafol, Fluxapyroxad, Isopyrazam, Iprodione, Isotianil, Mancozeb, Maneb, Metconazole, Metominostrobin, Myclobutanil, Penthiopyrad, Picoxystrobin, Propiconazole, Propineb, Prothioconazole, Pyraclostrobin, Tebuconazole, Tetraconazole, Thiophanate-methyl, Trifloxystrobin; Sugar beet Herbicides: Chloridazon, Desmedipham, Ethofumesate, Phenmedipham, Triallate, Clopyralid, Fluazifop, Lenacil, Metamitron, Quinmerac, Cycloxydim, Triflusulfuron, Tepraloxydim, Quizalofop; Sugar beet Insecticides: Imidacloprid, Clothianidin, Thiamethoxam, Thiacloprid, Acetamiprid, Dinetofuran, Deltamethrin, β-Cyfluthrin, gamma/lambda Cyhalothrin, 4-[[(6-Chlorpyridin-3-yl)methyl](2,2-difluorethyl)amino]furan-2(5H)-on, Tefluthrin, Rynaxypyr, Cyaxypyr, Fipronil, Carbofuran; Canola Herbicides: Clopyralid, Diclofop, Fluazifop, Glufosinate, Glyphosate, Metazachlor, Trifluralin Ethametsulfuron, Quinmerac, Quizalofop, Clethodim, Tepraloxydim; Canola Fungicides: Azoxystrobin, Bixafen, Boscalid, Carbendazim, Cyproconazole, Difenoconazole, Dimoxystrobin, Epoxiconazole, Fluazinam, Fluopyram, Fluoxastrobin, Flusilazole, Fluxapyroxad, Iprodione, Isopyrazam, Mepiquat-chloride, Metconazole, Metominostrobin, Paclobutrazole, Penthiopyrad, Picoxystrobin, Prochloraz, Prothioconazole, Pyraclostrobin, Tebuconazole, Thiophanate-methyl, Trifloxystrobin, Vinclozolin; Canola Insecticides: Carbofuran, Thiacloprid, Deltamethrin, Imidacloprid, Clothianidin, Thiamethoxam, Acetamiprid, Dinetofuran, β-Cyfluthrin, gamma and lambda Cyhalothrin, tau-Fluvaleriate, Ethiprole, Spinosad, Spinotoram, Flubendiamide, Rynaxypyr, Cyazypyr, 4-[[(6-Chlorpyridin-3-yl)methyl](2,2-difluorethyl)amino]furan-2(5H)-on.

Methods of Introducing Gene of the Invention into Another Plant

Also provided herein are methods of introducing the nucleic acid of the invention into another plant. The nucleic acid of the invention, or a fragment thereof, can be introduced into second plant by recurrent selection, backcrossing, pedigree breeding, line selection, mass selection, mutation breeding and/or genetic marker enhanced selection.

Thus, in one embodiment, the methods of the invention comprise crossing a first plant comprising a nucleic acid of the invention with a second plant to produce F1 progeny plants and selecting F1 progeny plants that comprise the nucleic acid of the invention. The methods may further comprise crossing the selected progeny plants with the first plant comprising the nucleic acid of the invention to produce backcross progeny plants and selecting backcross progeny plants that comprise the nucleic acid of the invention. Methods for evaluating pesticidal activity are provided elsewhere herein. The methods may further comprise repeating these steps one or more times in succession to produce selected second or higher backcross progeny plants that comprise the nucleic acid of the invention.

Any breeding method involving selection of plants for the desired phenotype can be used in the method of the present invention. In some embodiments, The F1 plants may be self-pollinated to produce a segregating F2 generation. Individual plants may then be selected which represent the desired phenotype (e.g., pesticidal activity) in each generation (F3, F4, F5, etc.) until the traits are homozygous or fixed within a breeding population.

The second plant can be a plant having a desired trait, such as herbicide tolerance, insect tolerance, drought tolerance, nematode control, water use efficiency, nitrogen use efficiency, improved nutritional value, disease resistance, improved photosynthesis, improved fiber quality, stress tolerance, improved reproduction, and the like. The second plant may be an elite event as described elsewhere herein In various embodiments, plant parts (whole plants, plant organs (e.g., leaves, stems, roots, etc.), seeds, plant cells, propagules, embryos, and the like) can be harvested from the resulting cross and either propagated or collected for downstream use (such as food, feed, biofuel, oil, flour, meal, etc).

Methods of Obtaining a Plant Product

The present invention also relates to a process for obtaining a commodity product, comprising harvesting and/or milling the grains from a crop comprising a nucleic acid of the invention to obtain the commodity product. Agronomically and commercially important products and/or compositions of matter including but not limited to animal feed, commodities, and plant products and by-products that are intended for use as food for human consumption or for use in compositions and commodities that are intended for human consumption, particularly devitalized seed/grain products, including a (semi-)processed products produced from such grain/seeds, wherein said product is or comprises whole or processed seeds or grain, animal feed, corn or soy meal, corn or soy flour, corn, corn starch, soybean meal, soy flour, flakes, soy protein concentrate, soy protein isolates, texturized soy protein concentrate, cosmetics, hair care products, soy nut butter, natto, tempeh, hydrolyzed soy protein, whipped topping, shortening, lecithin, edible whole soybeans (raw, roasted, or as edamame), soy yogurt, soy cheese, tofu, yuba, as well as cooked, polished, steamed, baked or parboiled grain, and the like are intended to be within the scope of the present invention if these products and compositions of matter contain detectable amounts of the nucleotide and/or amino acid sequences set forth herein as being diagnostic for any plant containing such nucleotide sequences.

The following examples are offered by way of illustration and not by way of limitation.

EXPERIMENTAL EXAMPLES

Example 1. Discovery of Novel Pesticidal Genes

Axmi486 was identified from a *Bacillus thuringiensis* ATX65002 strain using the steps as described in US Patent Publication US 20180371032 (herein incorporated by reference in its entirety) and was selected for further modifications. As shown previously, Axmi486 showed activity against *Plutella xylostella, Anticarsia gemmatalis, Diatraea grandiosella, Diatraea saccharalis, Heliothis virescens, Helicoverpa zea* and *Pseudoplusia includens* (Herein, "Target Insects"; see Table 7 of US 20180371032). It was further desired to create Axmi486 variants that show increased resistance, mortality and/or tolerance towards insects belonging to the species *Spodoptera* (e.g. *Spodoptera eridania* (herein, "SAW")) while maintaining effectiveness against the pests previously observed.

Example 2. Protein Engineering of Toxin Gene Axmi486 for Improved Bioactivity Against Soybean Pest SAW/

The selection of the positions targeted for the mutagenesis was done based on Axmi486's protein structure, internal function information, as well as experimental data from alanine scanning mutagenesis studies. A key objective for this experiment was to create Axmi Variants with increased resistance to SAW as compared to Axmi486 while at the same time ensuring that Axmi Variants did not display a reduced resistance to Target Insects as compared to Axmi486. Approximately, 3600 mutants were created for screening against SAW. Alanine mutants were identified and tested for activity against Hz and their stability against Hz gut juice. Mutants that did not disrupt activity and that retained the wild type activity were further screened for improved SAW activity. The outcome of these experiments allowed us to prioritize and select amino acids for targeted site-saturation mutagenesis. 47 relevant positions were targeted.

Mutant Library Creation

Mutagenesis was used to create single position mutation saturation libraries. Combinations of primers containing degenerate codons (NDT/VHG/TGG) were used to reduce redundancy at codon level. Axmi486_1Pb plasmid DNA template and Agilent Technologies Quick-Change Lightning Site-Directed Mutagenesis kit was used to create libraries. Mutant libraries were transformed in T7 Express competent cells and DNA sequencing of random colonies was done to confirm mutations.

Example 3. A Bioassay Screening for SAW Activity

For expression in *E. coli*, T7 Express competent cells are transformed with individual plasmids of the 47 relevant positions and plated onto LB agar carbenicillin plates. Single colonies from each library are inoculated in Instant TB supplemented with carbenicillin and glycerol and grown for 24 hours at 37° C. with 250 rpm shaking until cell saturation was reached.

Screening for SAW resistance was done with whole culture expressing variants identified in Example 2 inoculated from freshly transformed single bacterial colony libraries and wild type Axmi486. 47 single site saturation libraries were screened in SAW bioassay. Variants performing better than wild type Axmi486 were selected as preliminary hits for activity improvement confirmations with whole culture. Glycerol stocks of preliminary hits were streaked out onto LB agar carbenicillin plates. These selected hits were inoculated in fresh Instant TB media supplemented with carbenicillin and glycerol and grown at 37° C. for 24 hours with 250 rpm shaking. Once saturation was reached, a whole culture sample was aliquoted from each variant culture and mixed with appropriate LDS Sample Buffer and boiled for 10 minutes at 95° C. Densitometry was performed using a 4-12% bis-tris SDS-PAGE to quantitate Axmi486 protein band of interest at 79 kDa. A range of protein concentrations (1 mg/ml, 0.1 mg/ml, 0.03 mg/ml, 0.02 mg/ml) with multiple replicates were used to determine SAW activity improvement (See FIGS. 1*a*-1*e*). Improvement in SAW activity was confirmed in at least three independent biological replicates for five variants including three single position variants and two stacked/combined variants. Whole culture bioassays for SAW improved mutants were conducted against *Helicoverpa zea* (Hz)(see FIGS. 2*a* and 2*b*), *Anticarsia gemmatalis* (VBC) (See FIGS. 3*a* and 3*b*), *Spodoptera frugiperda* (FAW) (See FIGS. 4*a* and 4*b*), *Chrysodeixis includens* (SBL) (See FIG. 5), and *Heliothis virescens* (Hv) (See FIG. 6) to determine impact of mutation on the activity.

Example 3b. Assay Description

Lemnatec Imaging of bioassay plates was done to score for insecticidal activity. The Lemnatec takes an image of the plate and a trained algorithm gives a pixel score to each treated larvae infested well. The average size is the average object area of the larvae in pixels after treatment with protein. A larger average object area indicates that the larvae are growing and developing while a smaller average object area means the larvae are stunted and/or not growing or developing. Thus, the smaller the average object area, the greater the insecticidal activity of the protein.

TABLE 1a

Axmi486 Variants Identified to have increased Resistance to SAW while maintaining Resistance against Target Insects

| Gene name | Molecular weight (kDa) | Nucleotide SEQ ID NO | Amino acid SEQ ID NO |
|---|---|---|---|
| Axmi Variant 1 | 35.333 | 1 | 16 |
| Axmi Variant 2 | 35.347 | 2 | 17 |
| Axmi Variant 3 | 35.388 | 3 | 18 |
| Axmi Variant 4 | 35.319 | 4 | 19 |
| Axmi Variant 5 | 35.333 | 5 | 20 |
| Axmi Variant 6 | 35.304 | 6 | 21 |
| Axmi Variant 7 | 35.318 | 7 | 22 |
| Axmi Variant 8 | 35.359 | 8 | 23 |
| Axmi Variant 9 | 35.290 | 9 | 24 |
| Axmi Variant 10 | 35.304 | 10 | 25 |
| Axmi Variant 11 | 35.328 | 11 | 26 |
| Axmi Variant 12 | 35.342 | 12 | 27 |
| Axmi Variant 13 | 35.383 | 13 | 28 |

TABLE 1a-continued

Axmi486 Variants Identified to have increased Resistance to SAW while maintaining Resistance against Target Insects

| Gene name | Molecular weight (kDa) | Nucleotide SEQ ID NO | Amino acid SEQ ID NO |
|---|---|---|---|
| Axmi Variant 14 | 35.314 | 14 | 29 |
| Axmi Variant 15 | 35.328 | 15 | 30 |

TABLE 1b

References between internal names and sequence ID numbers

| Internal Name | DNA SEQ ID NO | Amino Acid SEQ ID NO |
|---|---|---|
| WT | N/A | N/A |
| R60S | 1 | 16 |
| R60T | 2 | 17 |
| E275D | 3 | 18 |
| R60S E275D | 4 | 19 |
| R60T E275D | 5 | 20 |
| R60S H97L T100N D96P | 6 | 21 |
| R60T H97L T100N D96P | 7 | 22 |
| E275D H97L T100N D96P | 8 | 23 |
| R60S E275D H97L T100N D96P | 9 | 24 |
| R60T E275D H97L T100N D96P | 10 | 25 |
| R60S T100N D96P | 11 | 26 |
| R60T T100N D96P | 12 | 27 |
| E275D T100N D96P | 13 | 28 |
| R60S E275D T100N D96P | 14 | 29 |
| R60T E275D T100N D96P | 15 | 30 |

TABLE 2

Bioassay results

| Mutation | SEQ ID NO | SAW Stunting % compared to WT |
|---|---|---|
| WT | | 0% |
| R60S | 16 | 75% |
| R60T | 17 | 78% |
| E275D | 18 | 69% |
| R60S E275D | 19 | 87% |
| R60T E275D | 20 | 83% |

Percentages based on treatment of 1 mg/ml fusion Axmi486 whole culture. Stunting percentage equals percentage of how much smaller the pest is compared to WT size.

Example 4. Vectoring of Genes for Plant Expression

Hz Improved Versions
Native and improved insecticidal activity variants of Axmi486 were nominated for plant testing. Plant transformation vectors and transgenic events were generated using techniques consistent with typical practices by those skilled in the art.
Synthetic sequences encoding the essential regions of the insecticidal trait were designed and created as a vital component of the described invention. The synthetic sequences were created with the intent of satisfactory protein expression in selected target plant species when compared with use of the native bacterial sequences. The synthetic versions are composed of altered nucleotide sequences that conserve the native protein sequence or introduce targeted mutations altering specific amino acids associated with improved pest control. The following versions were generated:

Version encoding the 315 amino acid sequence for the native axmi486 gene from *Bacillus thuringiensis*

Version encoding the 315 amino acid sequence for axmi486 gene from *Bacillus thuringiensis* including the single point mutation at position 96 (Aspartic acid to Proline)

Version encoding the 315 amino acid sequence for axmi486 gene from *Bacillus thuringiensis* including the single point mutation at position 97 (Histidine to Aspartic acid)

Version encoding the 315 amino acid sequence for axmi486 gene from *Bacillus thuringiensis* including the single point mutation at position 97 (Histidine to Leucine)

Version encoding the 315 amino acid sequence for axmi486 gene from *Bacillus thuringiensis* including the dual point mutations at position 96 (Aspartic acid to Proline) and position 100 (Threonine to Asparagine)

Version encoding the 315 amino acid sequence for axmi486 gene from *Bacillus thuringiensis* including the dual point mutations at position 96 (Aspartic acid to Proline) and 97 (Histidine to Aspartic acid)

Version encoding the 315 amino acid sequence for axmi486 gene from *Bacillus thuringiensis* including the dual point mutations at position 96 (Aspartic acid to Proline) and 97 (Histidine to Leucine)

Version encoding the 315 amino acid sequence for axmi486 gene from *Bacillus thuringiensis* including the triple point mutations at position 96 (Aspartic acid to Proline), 97 (Histidine to Leucine), and position 100 (Threonine to Asparagine)

The coding regions described were configured with appropriate promoter and terminator sequences required for plant expression of the desired transgene. An example for expression in dicots may include a promoter region of the ubiquitin 10 (UBQ10) of *A. thaliana* (Grefen et al., 2010) and the 3' untranslated region of the nopaline synthase gene (3' nos) of *A. tumefaciens* (Depicker A. et al., 1982) combined functionally with one of the described insecticidal synthetic sequences. Successful configurations would not be limited to the described example for expression in either dicots or monocot plants. Methods and techniques combining regulatory sequences with coding regions are well known in the art.

To generate the desired transgenic plants, the described or a similar pest control cassette would need to be combined with a suitable selectable marker cassette in an appropriate plant transformation vector. The resulting complete vector could be utilized with multiple transformation technologies including but not limited to *Agrobacterium*-mediated or biolistics by one skilled in the art.

SAW Improved Versions
Native and improved insecticidal activity variants of Axmi486 were nominated for plant testing. Plant transformation vectors and transgenic events were generated using techniques consistent with typical practices by those skilled in the art.
Synthetic sequences encoding the essential regions of the insecticidal trait were designed and created as a vital component of the described invention. The synthetic sequences were created with the intent of satisfactory protein expression in selected target plant species when compared with use of the native bacterial sequences. The synthetic versions are composed of altered nucleotide sequences that conserve the native protein sequence or introduce targeted mutations altering specific amino acids associated with improved pest control. The following versions were generated:

Version encoding the 315 amino acid sequence for the native axmi486 gene from *Bacillus thuringiensis*

Version encoding the 315 amino acid sequence for axmi486 gene from *Bacillus thuringiensis* including the single point mutation at position 60 (Arginine to Serine)

Version encoding the 315 amino acid sequence for axmi486 gene from *Bacillus thuringiensis* including the single point mutation at position 60 (Arginine to Threonine)

Version encoding the 315 amino acid sequence for axmi486 gene from *Bacillus thuringiensis* including the single point mutation at position 275 (Glutamic acid to Aspartic acid)

Version encoding the 315 amino acid sequence for axmi486 gene from *Bacillus thuringiensis* including the dual point mutations at position 60 (Arginine to Serine) and position 275 (Glutamic acid to Aspartic acid)

Version encoding the 315 amino acid sequence for axmi486 gene from *Bacillus thuringiensis* including the dual point mutations at position 60 (Arginine to Threonine) and position 275 (Glutamic acid to Aspartic acid)

The coding regions described were configured with appropriate promoter and terminator sequences required for plant expression of the desired transgene. An example for expression in dicots may include a promoter region of the ubiquitin 10 (UBQ10) of *A. thaliana* (Grefen et al., 2010) and the 3' untranslated region of the nopaline synthase gene (3' nos) of *A. tumefaciens* (Depicker A. et al., 1982) combined functionally with one of the described insecticidal synthetic sequences. Successful configurations would not be limited to the described example for expression in either dicots or monocot plants. Methods and techniques combining regulatory sequences with coding regions are well known in the art.

To generate the desired transgenic plants, the described or a similar pest control cassette would need to be combined with a suitable selectable marker cassette in an appropriate plant transformation vector. The resulting complete vector could be utilized with multiple transformation technologies including but not limited to *Agrobacterium*-mediated or biolistics by one skilled in the art.

Hz+SAW Improved Versions

Native and improved insecticidal activity variants of Axmi486 were nominated for plant testing. Plant transformation vectors and transgenic events were generated using techniques consistent with typical practices by those skilled in the art.

Synthetic sequences encoding the essential regions of the insecticidal trait were designed and created as a vital component of the described invention. The synthetic sequences were created with the intent of satisfactory protein expression in selected target plant species when compared with use of the native bacterial sequences. The synthetic versions are composed of altered nucleotide sequences that conserve the native protein sequence or introduce targeted mutations altering specific amino acids associated with improved pest control. The following versions were generated:

Version encoding the 315 amino acid sequence for the native axmi486 gene from *Bacillus thuringiensis*

Version encoding the 315 amino acid sequence for axmi486 gene from *Bacillus thuringiensis* including the quadruple point mutations at position 60 (Arginine to Serine), position 96 (Aspartic acid to Proline), position 97 (Histidine to Leucine), and position 100 (Threonine to Asparagine)

Version encoding the 315 amino acid sequence for axmi486 gene from *Bacillus thuringiensis* including the quadruple point mutations at position 96 (Aspartic acid to Proline), position 97 (Histidine to Leucine), position 100 (Threonine to Asparagine), and position 275 (Glutamic acid to Aspartic acid)

Version encoding the 315 amino acid sequence for axmi486 gene from *Bacillus thuringiensis* including the quintuple point mutations at position 60 (Arginine to Serine), position 96 (Aspartic acid to Proline), position 97 (Histidine to Leucine), position 100 (Threonine to Asparagine), and position 275 (Glutamic acid to Aspartic acid)

Version encoding the 315 amino acid sequence for axmi486 gene from *Bacillus thuringiensis* including the quintuple point mutations at position 60 (Arginine to Threonine), position 96 (Aspartic acid to Proline), position 97 (Histidine to Leucine), position 100 (Threonine to Asparagine), and position 275 (Glutamic acid to Aspartic acid)

The coding regions described were configured with appropriate promoter and terminator sequences required for plant expression of the desired transgene. An example for expression in dicots may include a promoter region of the ubiquitin 10 (UBQ10) of *A. thaliana* (Grefen et al., 2010) and the 3' untranslated region of the nopaline synthase gene (3' nos) of *A. tumefaciens* (Depicker A. et al., 1982) combined functionally with one of the described insecticidal synthetic sequences. Successful configurations would not be limited to the described example for expression in either dicots or monocot plants. Methods and techniques combining regulatory sequences with coding regions are well known in the art.

To generate the desired transgenic plants, the described or a similar pest control cassette would need to be combined with a suitable selectable marker cassette in an appropriate plant transformation vector. The resulting complete vector could be utilized with multiple transformation technologies including but not limited to *Agrobacterium*-mediated or biolistics by one skilled in the art.

Examples of General Components for Pesticidal Cassette:

UBQ10:
Promoter region of the ubiquitin 10 (UBQ10) of *Arabidopsis thaliana* (Grefen et al., 2010)

Axmi486 WT:
Coding sequence of the axmi486 gene of *Bacillus thuringiensis*
A variant of axmi486-1Pb with a silent mutation introduced to remove an allergen hit. axmi486 encodes a novel pesticidal protein, ~49% similar to MTX3. axmi486-1Pb is a variant of axmi486 optimized for soybean expression (JCeasar 46%).

3' Nos:
3' untranslated region of the nopaline synthase gene of *Agrobacterium tumefaciens* (Depicker A. et al., 1982)

Example 5. Soybean Transformation

Soybean transformation is achieved using methods well known in the art, such as the one described using the *Agrobacterium tumefaciens* mediated transformation soybean half-seed explants using essentially the method described by Paz et al. (2006), Plant cell Rep. 25:206. Transformants are identified using tembotrione as selection marker. The appearance of green shoots was observed and documented as an indicator of tolerance to the herbicide isoxaflutole or tembotrione. The tolerant transgenic shoots will show normal greening comparable to wild-type soybean shoots not treated with isoxaflutole or tembotrione, whereas wild-type soybean shoots treated with the same amount of isoxaflutole or tembotrione will be entirely bleached. This indicates that the presence of the HPPD protein enables the tolerance to HPPD inhibitor herbicides, like isoxaflutole or tembotrione.

Tolerant green shoots are transferred to rooting media or grafted. Rooted plantlets are transferred to the greenhouse after an acclimation period. Plants containing the transgene are then sprayed with HPPD inhibitor herbicides, as for example with tembotrione at a rate of 100 g AI/ha or with mesotrione at a rate of 300 g AI/ha supplemented with ammonium sulfate methyl ester rapeseed oil. Ten days after the application the symptoms due to the application of the herbicide are evaluated and compared to the symptoms observed on wild type plants under the same conditions.

Example 6. Transformation of Maize Cells with the Pesticidal Protein Genes Described Herein Maize ears are best collected 8-12 days after pollination. Embryos are isolated from the ears, and those embryos 0.8-1.5 mm in size are preferred for use in transformation. Embryos are plated scutellum side-up on a suitable incubation media, such as DN62A5S media (3.98 g/L N6 Salts; 1 mL/L (of 1000× Stock) N6 Vitamins; 800 mg/L L-Asparagine; 100 mg/L Myo-inositol; 1.4 g/L L-Proline; 100 mg/L Casamino acids; 50 g/L sucrose; 1 mL/L (of 1 mg/mL Stock) 2,4-D). However, media and salts other than DN62A5S are suitable and are known in the art. Embryos are incubated overnight at 25° C. in the dark. However, it is not necessary per se to incubate the embryos overnight.

The resulting explants are transferred to mesh squares (30-40 per plate), transferred onto osmotic media for about 30-45 minutes, then transferred to a beaming plate (see, for example, PCT Publication No. WO/0138514 and U.S. Pat. No. 5,240,842).

DNA constructs designed to the genes of the invention in plant cells are accelerated into plant tissue using an aerosol beam accelerator, using conditions essentially as described in PCT Publication No. WO/0138514. After beaming, embryos are incubated for about 30 min on osmotic media and placed onto incubation media overnight at 25° C. in the dark. To avoid unduly damaging beamed explants, they are incubated for at least 24 hours prior to transfer to recovery media. Embryos are then spread onto recovery period media, for about 5 days, 25° C. in the dark, then transferred to a selection media. Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated by methods known in the art. The resulting shoots are allowed to root on rooting media, and the resulting plants are transferred to nursery pots and propagated as transgenic plants.

TABLE 3

Materials, DN62A5S Media

| Components | Per Liter | Source |
|---|---|---|
| Chu's N6 Basal Salt Mixture (Prod. No. C 416) | 3.98 g/L | Phytotechnology Labs |
| Chu's N6 Vitamin Solution (Prod. No. C 149) | 1 mL/L (of 1000× Stock) | Phytotechnology Labs |
| L-Asparagine | 800 mg/L | Phytotechnology Labs |
| Myo-inositol | 100 mg/L | Sigma |
| L-Proline | 1.4 g/L | Phytotechnology Labs |
| Casamino acids | 100 mg/L | Fisher Scientific |
| Sucrose | 50 g/L | Phytotechnology Labs |
| 2,4-D (Prod. No. D-7299) | 1 mL/L (of 1 mg/mL Stock) | Sigma |

The pH of the solution is adjusted to pH 5.8 with 1N KOH/1N KCl, Gelrite (Sigma) is added at a concentration up to 3 g/L, and the media is autoclaved. After cooling to 50° C., 2 ml/L of a 5 mg/ml stock solution of silver nitrate (Phytotechnology Labs) is added.

Example 7. Transformation of Genes of the Invention in Plant Cells by *Agrobacterium*-Mediated Transformation Ears are best collected 8-12 days after pollination. Embryos are isolated from the ears, and those embryos 0.8-1.5 mm in size are preferred for use in transformation. Embryos are plated scutellum side-up on a suitable incubation media and incubated overnight at 25° C. in the dark. However, it is not necessary per se to incubate the embryos overnight. Embryos are contacted with an *Agrobacterium* strain containing the appropriate vectors for Ti plasmid mediated transfer for about 5-10 min, and then plated onto co-cultivation media for about 3 days (22° C. in the dark). After co-cultivation, explants are transferred to recovery period media for 5-10 days (at 25° C. in the dark). Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated as known in the art.

FIG. 7 Protein alignment of all variants against Axmi486 WT.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A recombinant nucleic acid molecule comprising a nucleotide sequence encoding an amino acid sequence having pesticidal activity, wherein said nucleotide sequence is selected from the group consisting of:
   a) the nucleotide sequence set forth in SEQ ID NO: 10; and
   b) a nucleotide sequence that encodes a polypeptide comprising the amino acid sequence of SEQ ID NO: 25.

2. A recombinant nucleic acid sequence that encodes a polypeptide comprising the amino acid sequence of SEQ ID NO:25, encoding an Axmi486 polypeptide having a modified amino acid corresponding to positions 60, 96, 97, 100 and 275, wherein the polypeptide confers increased resistance against Southern armyworm (SAW) as compared to a control not comprising said modifications.

3. The Axmi486 polypeptide according to claim 2, wherein the modified amino acid at is R60T, D96P, H97L, T100N and E275D.

4. The recombinant nucleic acid molecule of claim 1, wherein said recombinant nucleic acid molecule is a synthetic sequence that has been designed for expression in a plant.

5. The recombinant nucleic acid molecule of claim 1, wherein said nucleotide sequence is operably linked to a promoter capable of directing expression of said nucleotide sequence in a plant cell.

6. A vector comprising the recombinant nucleic acid molecule of claim 1.

7. The vector of claim 6, further comprising a nucleic acid molecule encoding a heterologous polypeptide.

8. A host cell that contains the recombinant nucleic acid molecule of claim 1.

9. The host cell of claim 8 that is a bacterial host cell.

10. The host cell of claim 8 that is a plant cell.

11. A transgenic plant comprising the host cell of claim 10.

12. The transgenic plant of claim 11, wherein said plant is selected from the group consisting of maize, Sorghum, wheat, cabbage, sunflower, tomato, crucifers, peppers, potato, cotton, rice, soybean, sugar beet, sugarcane, tobacco, barley, and oilseed rape.

13. A transgenic seed comprising the nucleic acid molecule of claim 1.

14. A recombinant polypeptide with pesticidal activity comprising the amino acid sequence of SEQ ID NO:25.

15. The polypeptide of claim 14 further comprising heterologous amino acid sequences.

16. A composition comprising the polypeptide of claim 14.

17. The composition of claim 16, wherein said composition is selected from the group consisting of a powder, dust, pellet, granule, spray, emulsion, colloid, and solution.

18. A plant or plant cell having stably incorporated into its genome a DNA construct comprising a nucleotide sequence that encodes a protein having pesticidal activity, wherein said nucleotide sequence is selected from the group consisting of:
   a) the nucleotide sequence set forth in SEQ ID NO:10; and
   b) a nucleotide sequence that encodes a polypeptide comprising the amino acid sequence of SEQ ID NO:25.

19. A method for protecting a plant from a pest, comprising expressing in a plant or cell thereof a nucleotide sequence that encodes a pesticidal polypeptide, wherein said nucleotide sequence is selected from the group consisting of:
   a) the nucleotide sequence set forth in SEQ ID NO:10; and
   b) a nucleotide sequence that encodes a polypeptide comprising the amino acid sequence of SEQ ID NO:25.

20. The method of claim 19, wherein said plant produces a pesticidal polypeptide having pesticidal activity against a Spodoptera eridania, lepidopteran, hemipteran, coleopteran, nematode, or dipteran pest.

21. A method for increasing yield in a plant comprising growing in a field a plant of or a seed thereof having stably incorporated into its genome a DNA construct comprising a nucleotide sequence that encodes a protein having pesticidal activity, wherein said nucleotide sequence is selected from the group consisting of:
   a) the nucleotide sequence set forth in SEQ ID NO:10; and
   b) a nucleotide sequence that encodes a polypeptide comprising the amino acid sequence of SEQ ID NO:25;
wherein said field is infested with a pest against which said polypeptide has pesticidal activity.

22. A commodity product comprising the nucleic acid molecule of claim 1, or a protein encoded thereby, wherein said product is selected from the group consisting of whole or processed seeds or grain, animal feed, corn or soy meal, corn or soy flour, corn starch, soybean meal, soy flour, flakes, soy protein concentrate, soy protein isolates, texturized soy protein concentrate, cosmetics, hair care products, soy nut butter, natto, tempeh, hydrolyzed soy protein, whipped topping, shortening, lecithin, edible whole soybeans, soy yogurt, soy cheese, tofu, yuba, and cooked, polished, steamed, baked or parboiled grain.

* * * * *

SEQUENCE LISTING

<160> NUMBER OF SEQ ID NOS: 36

<210> SEQ ID NO 1
<211> LENGTH: 948
<212> TYPE: DNA
<213> ORGANISM: Artificial Sequence
<220> FEATURE:
<223> OTHER INFORMATION: Variant: Axmi486-R60S

<400> SEQUENCE: 1

```
atgctggctg ttgctgccaa gacagagaac aacaaggagc agcaagtgat cacccacttc      60
aaccagaggg agaacaagtt ccctgatgtt ggccaaggaa tccaatggct ctctcagttc     120
tatgggaaat cattgaagaa caatggagaa ggatattctc ttggccaaga tgtgatgagt     180
tacttcttgg aggtgaagaa cagctatggg cagcttgcaa tggagcctca ggtcatctca     240
acaactcctc tctgggctgg ccaaagtgat ttggagaatg caacagatca tgagcaaacc     300
ctcaactcaa cagagttcaa gaagacatac agcaacacca caacaacctc cacagagaat     360
ggcttcatga ttggccaaga aacagaaggg aaggttggga ttccctttgt tgctgaaggg     420
aaggtcacca tcaagacaga gtacaacttc aatcacacca tggctatgaa aacttcagag     480
agtgtggaat atattgctcc aagccaaagc atcaaggttc ctcctcacac cattgcaagg     540
gtgactgctc tgctggatgt gaagaagatc aaggggaaga tgcacctcta ttcagagatt     600
ggcttgaaca aggattatgg ctatgacatg gtgccactgg tgtacaagta tggaggcccc     660
ttcaagtatg tcacccttgg aaccctctat gatgaaggct acaagcaagc tcagctggat     720
tacttcaaca tggggaatgt gattccagaa gagattgaaa ctgtttcaaa gagcaacaac     780
ccaaaccact tgctggcttc tggtgttggg atctttgaga gtgaatatgg aagtgtcttc     840
aatgtgaagg tggaatacat caacattaac accaagaaga ttgagaagac agagaatctc     900
accattgagc aaccattgt gccagtgaag cagaccaaca ccaagtaa                   948
```

<210> SEQ ID NO 2
<211> LENGTH: 948
<212> TYPE: DNA
<213> ORGANISM: Artificial Sequence
<220> FEATURE:
<223> OTHER INFORMATION: Variant: Axmi486-R60T

<400> SEQUENCE: 2

```
atgctggctg ttgctgccaa gacagagaac aacaaggagc agcaagtgat cacccacttc      60
aaccagaggg agaacaagtt ccctgatgtt ggccaaggaa tccaatggct ctctcagttc     120
tatgggaaat cattgaagaa caatggagaa ggatattctc ttggccaaga tgtgatgacg     180
tacttcttgg aggtgaagaa cagctatggg cagcttgcaa tggagcctca ggtcatctca     240
acaactcctc tctgggctgg ccaaagtgat ttggagaatg caacagatca tgagcaaacc     300
ctcaactcaa cagagttcaa gaagacatac agcaacacca caacaacctc cacagagaat     360
ggcttcatga ttggccaaga aacagaaggg aaggttggga ttccctttgt tgctgaaggg     420
aaggtcacca tcaagacaga gtacaacttc aatcacacca tggctatgaa aacttcagag     480
agtgtggaat atattgctcc aagccaaagc atcaaggttc ctcctcacac cattgcaagg     540
gtgactgctc tgctggatgt gaagaagatc aaggggaaga tgcacctcta ttcagagatt     600
ggcttgaaca aggattatgg ctatgacatg gtgccactgg tgtacaagta tggaggcccc     660
ttcaagtatg tcacccttgg aaccctctat gatgaaggct acaagcaagc tcagctggat     720
tacttcaaca tggggaatgt gattccagaa gagattgaaa ctgtttcaaa gagcaacaac     780
```

```
ccaaaccact tgctggcttc tggtgttggg atctttgaga gtgaatatgg aagtgtcttc    840
aatgtgaagg tggaatacat caacattaac accaagaaga ttgagaagac agagaatctc    900
accattgagc caaccattgt gccagtgaag cagaccaaca ccaagtaa                 948
```

<210> SEQ ID NO 3
<211> LENGTH: 948
<212> TYPE: DNA
<213> ORGANISM: Artificial Sequence
<220> FEATURE:
<223> OTHER INFORMATION: Variant: Axmi486-E275D

<400> SEQUENCE: 3

```
atgctggctg ttgctgccaa gacagagaac aacaaggagc agcaagtgat cacccacttc     60
aaccagaggg agaacaagtt ccctgatgtt ggccaaggaa tccaatggct ctctcagttc    120
tatgggaaat cattgaagaa caatggagaa ggatattctc ttggccaaga tgtgatgaga    180
tacttcttgg aggtgaagaa cagctatggg cagcttgcaa tggagcctca ggtcatctca    240
acaactcctc tctgggctgg ccaaagtgat ttggagaatg caacagatca tgagcaaacc    300
ctcaactcaa cagagttcaa gaagacatac agcaacacca caacaacctc cacagagaat    360
ggcttcatga ttggccaaga aacagaaggg aaggttggga ttccctttgt tgctgaaggg    420
aaggtcacca tcaagacaga gtacaacttc aatcacacca tggctatga acttcagag     480 agtgtggaat atattgctcc aagccaaagc atcaaggttc ctcctcacac cattgcaagg    540
gtgactgctc tgctggatgt gaagaagatc aaggggaaga tgcacctcta ttcagagatt    600
ggcttgaaca aggattatgg ctatgacatg gtgccactgg tgtacaagta tggaggcccc    660
ttcaagtatg tcacccttgg aaccctctat gatgaaggct acaagcaagc tcagctggat    720
tacttcaaca tggggaatgt gattccagaa gagattgaaa ctgtttcaaa gagcaacaac    780
ccaaaccact gctggcttc tggtgttggg atctttgaga gtgattatgg aagtgtcttc     840
aatgtgaagg tggaatacat caacattaac accaagaaga ttgagaagac agagaatctc    900
accattgagc caaccattgt gccagtgaag cagaccaaca ccaagtaa                 948
```

<210> SEQ ID NO 4
<211> LENGTH: 948
<212> TYPE: DNA
<213> ORGANISM: Artificial Sequence
<220> FEATURE:
<223> OTHER INFORMATION: Variant: Axmi486-R60S E275D

<400> SEQUENCE: 4

```
atgctggctg ttgctgccaa gacagagaac aacaaggagc agcaagtgat cacccacttc     60
aaccagaggg agaacaagtt ccctgatgtt ggccaaggaa tccaatggct ctctcagttc    120
tatgggaaat cattgaagaa caatggagaa ggatattctc ttggccaaga tgtgatgagt    180
tacttcttgg aggtgaagaa cagctatggg cagcttgcaa tggagcctca ggtcatctca    240
acaactcctc tctgggctgg ccaaagtgat ttggagaatg caacagatca tgagcaaacc    300
ctcaactcaa cagagttcaa gaagacatac agcaacacca caacaacctc cacagagaat    360
ggcttcatga ttggccaaga aacagaaggg aaggttggga ttccctttgt tgctgaaggg    420
aaggtcacca tcaagacaga gtacaacttc aatcacacca tggctatga acttcagag     480 agtgtggaat atattgctcc aagccaaagc atcaaggttc ctcctcacac cattgcaagg    540
gtgactgctc tgctggatgt gaagaagatc aaggggaaga tgcacctcta ttcagagatt    600
```

| | |
|---|---|
| ggcttgaaca aggattatgg ctatgacatg gtgccactgg tgtacaagta tggaggcccc | 660 |
| ttcaagtatg tcacccttgg aaccctctat gatgaaggct acaagcaagc tcagctggat | 720 |
| tacttcaaca tggggaatgt gattccagaa gagattgaaa ctgtttcaaa gagcaacaac | 780 |
| ccaaaccact tgctggcttc tggtgttggg atctttgaga gtgattatgg aagtgtcttc | 840 |
| aatgtgaagg tggaatacat caacattaac accaagaaga ttgagaagac agagaatctc | 900 |
| accattgagc aaccattgt gccagtgaag cagaccaaca ccaagtaa | 948 |

```
<210> SEQ ID NO 5
<211> LENGTH: 948
<212> TYPE: DNA
<213> ORGANISM: Artificial Sequence
<220> FEATURE:
<223> OTHER INFORMATION: Variant: Axmi486-R60T E275D

<400> SEQUENCE: 5
```

| | |
|---|---|
| atgctggctg ttgctgccaa gacagagaac aacaaggagc agcaagtgat cacccacttc | 60 |
| aaccagaggg agaacaagtt ccctgatgtt ggccaaggaa tccaatggct ctctcagttc | 120 |
| tatgggaaat cattgaagaa caatggagaa ggatattctc ttggccaaga tgtgatgacg | 180 |
| tacttcttgg aggtgaagaa cagctatggg cagcttgcaa tggagcctca ggtcatctca | 240 |
| acaactcctc tctgggctgg ccaaagtgat ttggagaatg caacagatca tgagcaaacc | 300 |
| ctcaactcaa cagagttcaa gaagacatac agcaacacca caacaacctc cacagagaat | 360 |
| ggcttcatga ttggccaaga aacagaaggg aaggttggga ttcccttgt tgctgaaggg | 420 |
| aaggtcacca tcaagacaga gtacaacttc aatcacacca tggctatga aacttcagag | 480 |
| agtgtggaat atattgctcc aagccaaagc atcaaggttc ctcctcacac cattgcaagg | 540 |
| gtgactgctc tgctggatgt gaagaagatc aaggggaaga tgcacctcta ttcagagatt | 600 |
| ggcttgaaca aggattatgg ctatgacatg gtgccactgg tgtacaagta tggaggcccc | 660 |
| ttcaagtatg tcacccttgg aaccctctat gatgaaggct acaagcaagc tcagctggat | 720 |
| tacttcaaca tggggaatgt gattccagaa gagattgaaa ctgtttcaaa gagcaacaac | 780 |
| ccaaaccact tgctggcttc tggtgttggg atctttgaga gtgattatgg aagtgtcttc | 840 |
| aatgtgaagg tggaatacat caacattaac accaagaaga ttgagaagac agagaatctc | 900 |
| accattgagc aaccattgt gccagtgaag cagaccaaca ccaagtaa | 948 |

```
<210> SEQ ID NO 6
<211> LENGTH: 948
<212> TYPE: DNA
<213> ORGANISM: Artificial Sequence
<220> FEATURE:
<223> OTHER INFORMATION: Variant: Axmi486-R60S H97L T100N D96P

<400> SEQUENCE: 6
```

| | |
|---|---|
| atgctggctg ttgctgccaa gacagagaac aacaaggagc agcaagtgat cacccacttc | 60 |
| aaccagaggg agaacaagtt ccctgatgtt ggccaaggaa tccaatggct ctctcagttc | 120 |
| tatgggaaat cattgaagaa caatggagaa ggatattctc ttggccaaga tgtgatgagt | 180 |
| tacttcttgg aggtgaagaa cagctatggg cagcttgcaa tggagcctca ggtcatctca | 240 |
| acaactcctc tctgggctgg ccaaagtgat ttggagaatg caacaccgct ggagcaaaat | 300 |
| ctcaactcaa cagagttcaa gaagacatac agcaacacca caacaacctc cacagagaat | 360 |
| ggcttcatga ttggccaaga aacagaaggg aaggttggga ttcccttgt tgctgaaggg | 420 |
| aaggtcacca tcaagacaga gtacaacttc aatcacacca tggctatga aacttcagag | 480 |

```
agtgtggaat atattgctcc aagccaaagc atcaaggttc ctcctcacac cattgcaagg    540
gtgactgctc tgctggatgt gaagaagatc aaggggaaga tgcacctcta ttcagagatt    600
ggcttgaaca aggattatgg ctatgacatg gtgccactgg tgtacaagta tggaggcccc    660
ttcaagtatg tcacccttgg aaccctctat gatgaaggct acaagcaagc tcagctggat    720
tacttcaaca tggggaatgt gattccagaa gagattgaaa ctgtttcaaa gagcaacaac    780
ccaaaccact tgctggcttc tggtgttggg atctttgaga gtgaatatgg aagtgtcttc    840
aatgtgaagg tggaatacat caacattaac accaagaaga ttgagaagac agagaatctc    900
accattgagc caaccattgt gccagtgaag cagaccaaca ccaagtaa                  948

<210> SEQ ID NO 7
<211> LENGTH: 948
<212> TYPE: DNA
<213> ORGANISM: Artificial Sequence
<220> FEATURE:
<223> OTHER INFORMATION: Variant: Axmi486-R60T H97L T100N D96P

<400> SEQUENCE: 7
atgctggctg ttgctgccaa gacagagaac aacaaggagc agcaagtgat cacccacttc     60
aaccagaggg agaacaagtt ccctgatgtt ggccaaggaa tccatggct ctctcagttc    120 tatgggaaat cattgaagaa caatggagaa ggatattctc ttggccaaga tgtgatgacg    180
tacttcttgg aggtgaagaa cagctatggg cagcttgcaa tggagcctca ggtcatctca    240
acaactcctc tctgggctgg ccaaagtgat ttggagaatg caacaccgct ggagcaaaat    300
ctcaactcaa cagagttcaa gaagacatac agcaacacca caacaacctc cacagagaat    360
ggcttcatga ttggccaaga aacagaaggg aaggttggga ttcccttgt tgctgaaggg    420 aaggtcacca tcaagacaga gtacaacttc aatcacacca atggctatga aacttcagag    480
agtgtggaat atattgctcc aagccaaagc atcaaggttc ctcctcacac cattgcaagg    540
gtgactgctc tgctggatgt gaagaagatc aaggggaaga tgcacctcta ttcagagatt    600
ggcttgaaca aggattatgg ctatgacatg gtgccactgg tgtacaagta tggaggcccc    660
ttcaagtatg tcacccttgg aaccctctat gatgaaggct acaagcaagc tcagctggat    720
tacttcaaca tggggaatgt gattccagaa gagattgaaa ctgtttcaaa gagcaacaac    780
ccaaaccact tgctggcttc tggtgttggg atctttgaga gtgaatatgg aagtgtcttc    840
aatgtgaagg tggaatacat caacattaac accaagaaga ttgagaagac agagaatctc    900
accattgagc caaccattgt gccagtgaag cagaccaaca ccaagtaa                  948

<210> SEQ ID NO 8
<211> LENGTH: 948
<212> TYPE: DNA
<213> ORGANISM: Artificial Sequence
<220> FEATURE:
<223> OTHER INFORMATION: Variant: Axmi486-E275D H97L T100N D96P

<400> SEQUENCE: 8
atgctggctg ttgctgccaa gacagagaac aacaaggagc agcaagtgat cacccacttc     60
aaccagaggg agaacaagtt ccctgatgtt ggccaaggaa tccatggct ctctcagttc    120 tatgggaaat cattgaagaa caatggagaa ggatattctc ttggccaaga tgtgatgaga    180
tacttcttgg aggtgaagaa cagctatggg cagcttgcaa tggagcctca ggtcatctca    240
acaactcctc tctgggctgg ccaaagtgat ttggagaatg caacaccgct ggagcaaaat    300
```

| | | |
|---|---|---|
| ctcaactcaa cagagttcaa gaagacatac agcaacacca caacaacctc cacagagaat | 360 | |
| ggcttcatga ttggccaaga acagaaggg aaggttggga ttcccttgt tgctgaaggg | 420 | |
| aaggtcacca tcaagacaga gtacaacttc aatcacacca atggctatga aacttcagag | 480 | |
| agtgtggaat atattgctcc aagccaaagc atcaaggttc ctcctcacac cattgcaagg | 540 | |
| gtgactgctc tgctggatgt gaagaagatc aaggggaaga tgcacctcta ttcagagatt | 600 | |
| ggcttgaaca aggattatgg ctatgacatg gtgccactgg tgtacaagta tggaggcccc | 660 | |
| ttcaagtatg tcacccttgg aaccctctat gatgaaggct acaagcaagc tcagctggat | 720 | |
| tacttcaaca tggggaatgt gattccagaa gagattgaaa ctgtttcaaa gagcaacaac | 780 | |
| ccaaaccact tgctggcttc tggtgttggg atctttgaga gtgattatgg aagtgtcttc | 840 | |
| aatgtgaagg tggaatacat caacattaac accaagaaga ttgagaagac agagaatctc | 900 | |
| accattgagc caaccattgt gccagtgaag cagaccaaca ccaagtaa | 948 | |

<210> SEQ ID NO 9
<211> LENGTH: 948
<212> TYPE: DNA
<213> ORGANISM: Artificial Sequence
<220> FEATURE:
<223> OTHER INFORMATION: Variant: Axmi486-R60S E275D H97L T100N D96P

<400> SEQUENCE: 9

| | | |
|---|---|---|
| atgctggctg ttgctgccaa gacagagaac aacaaggagc agcaagtgat cacccacttc | 60 | |
| aaccagaggg agaacaagtt ccctgatgtt ggccaaggaa tccaatggct ctctcagttc | 120 | |
| tatgggaaat cattgaagaa caatggagaa ggatattctc ttggccaaga tgtgatgagt | 180 | |
| tacttcttgg aggtgaagaa cagctatggg cagcttgcaa tggagcctca ggtcatctca | 240 | |
| acaactcctc tctgggctgg ccaaagtgat ttggagaatg caacaccgct ggagcaaaat | 300 | |
| ctcaactcaa cagagttcaa gaagacatac agcaacacca caacaacctc cacagagaat | 360 | |
| ggcttcatga ttggccaaga acagaaggg aaggttggga ttcccttgt tgctgaaggg | 420 | |
| aaggtcacca tcaagacaga gtacaacttc aatcacacca atggctatga aacttcagag | 480 | |
| agtgtggaat atattgctcc aagccaaagc atcaaggttc ctcctcacac cattgcaagg | 540 | |
| gtgactgctc tgctggatgt gaagaagatc aaggggaaga tgcacctcta ttcagagatt | 600 | |
| ggcttgaaca aggattatgg ctatgacatg gtgccactgg tgtacaagta tggaggcccc | 660 | |
| ttcaagtatg tcacccttgg aaccctctat gatgaaggct acaagcaagc tcagctggat | 720 | |
| tacttcaaca tggggaatgt gattccagaa gagattgaaa ctgtttcaaa gagcaacaac | 780 | |
| ccaaaccact tgctggcttc tggtgttggg atctttgaga gtgattatgg aagtgtcttc | 840 | |
| aatgtgaagg tggaatacat caacattaac accaagaaga ttgagaagac agagaatctc | 900 | |
| accattgagc caaccattgt gccagtgaag cagaccaaca ccaagtaa | 948 | |

<210> SEQ ID NO 10
<211> LENGTH: 948
<212> TYPE: DNA
<213> ORGANISM: Artificial Sequence
<220> FEATURE:
<223> OTHER INFORMATION: Variant: Axmi486-R60T E275D H97L T100N D96P

<400> SEQUENCE: 10

| | | |
|---|---|---|
| atgctggctg ttgctgccaa gacagagaac aacaaggagc agcaagtgat cacccacttc | 60 | |
| aaccagaggg agaacaagtt ccctgatgtt ggccaaggaa tccaatggct ctctcagttc | 120 | |
| tatgggaaat cattgaagaa caatggagaa ggatattctc ttggccaaga tgtgatgacg | 180 | |

```
tacttcttgg aggtgaagaa cagctatggg cagcttgcaa tggagcctca ggtcatctca      240
acaactcctc tctgggctgg ccaaagtgat ttggagaatg caacaccgct ggagcaaaat      300
ctcaactcaa cagagttcaa gaagacatac agcaacacca caacaacctc cacagagaat      360
ggcttcatga ttggccaaga aacagaaggg aaggttggga ttcccttttgt tgctgaaggg     420 aaggtcacca tcaagacaga gtacaacttc aatcacacca atggctatga aacttcagag      480
agtgtggaat atattgctcc aagccaaagc atcaaggttc ctcctcacac cattgcaagg      540
gtgactgctc tgctggatgt gaagaagatc aaggggaaga tgcacctcta ttcagagatt      600
ggcttgaaca aggattatgg ctatgacatg gtgccactgg tgtacaagta tggaggcccc      660
ttcaagtatg tcacccttgg aaccctctat gatgaaggct acaagcaagc tcagctggat      720
tacttcaaca tggggaatgt gattccagaa gagattgaaa ctgtttcaaa gagcaacaac      780
ccaaaccact tgctggcttc tggtgttggg atctttgaga gtgattatgg aagtgtcttc      840
aatgtgaagg tggaatacat caacattaac accaagaaga ttgagaagac agagaatctc      900
accattgagc aaccattgt gccagtgaag cagaccaaca ccaagtaa                     948
```

<210> SEQ ID NO 11
<211> LENGTH: 948
<212> TYPE: DNA
<213> ORGANISM: Artificial Sequence
<220> FEATURE:
<223> OTHER INFORMATION: Variant: Axmi486-R60S T100N D96P

<400> SEQUENCE: 11

```
atgctggctg ttgctgccaa gacagagaac aacaaggagc agcaagtgat cacccacttc      60
aaccagaggg agaacaagtt ccctgatgtt ggccaaggaa tccaatggct ctctcagttc     120
tatgggaaat cattgaagaa caatggagaa ggatattctc ttggccaaga tgtgatgagt     180
tacttcttgg aggtgaagaa cagctatggg cagcttgcaa tggagcctca ggtcatctca     240
acaactcctc tctgggctgg ccaaagtgat ttggagaatg caacaccgca tgagcaaaat     300
ctcaactcaa cagagttcaa gaagacatac agcaacacca caacaacctc cacagagaat     360
ggcttcatga ttggccaaga aacagaaggg aaggttggga ttcccttttgt tgctgaaggg    420 aaggtcacca tcaagacaga gtacaacttc aatcacacca atggctatga aacttcagag     480
agtgtggaat atattgctcc aagccaaagc atcaaggttc ctcctcacac cattgcaagg     540
gtgactgctc tgctggatgt gaagaagatc aaggggaaga tgcacctcta ttcagagatt     600
ggcttgaaca aggattatgg ctatgacatg gtgccactgg tgtacaagta tggaggcccc     660
ttcaagtatg tcacccttgg aaccctctat gatgaaggct acaagcaagc tcagctggat     720
tacttcaaca tggggaatgt gattccagaa gagattgaaa ctgtttcaaa gagcaacaac     780
ccaaaccact tgctggcttc tggtgttggg atctttgaga gtgaatatgg aagtgtcttc     840
aatgtgaagg tggaatacat caacattaac accaagaaga ttgagaagac agagaatctc     900
accattgagc aaccattgt gccagtgaag cagaccaaca ccaagtaa                     948
```

<210> SEQ ID NO 12
<211> LENGTH: 948
<212> TYPE: DNA
<213> ORGANISM: Artificial Sequence
<220> FEATURE:
<223> OTHER INFORMATION: Variant: Axmi486-R60T T100N D96P

<400> SEQUENCE: 12

| | |
|---|---|
| atgctggctg ttgctgccaa gacagagaac aacaaggagc agcaagtgat cacccacttc | 60 |
| aaccagaggg agaacaagtt ccctgatgtt ggccaaggaa tccaatggct ctctcagttc | 120 |
| tatgggaaat cattgaagaa caatggagaa ggatattctc ttggccaaga gtgatgacg | 180 |
| tacttcttgg aggtgaagaa cagctatggg cagcttgcaa tggagcctca ggtcatctca | 240 |
| acaactcctc tctgggctgg ccaaagtgat ttggagaatg caacaccgca tgagcaaaat | 300 |
| ctcaactcaa cagagttcaa gaagacatac agcaacacca caacaacctc cacagagaat | 360 |
| ggcttcatga ttggccaaga aacagaaggg aaggttggga ttccctttgt tgctgaaggg | 420 |
| aaggtcacca tcaagacaga gtacaacttc aatcacacca tggctatga aacttcagag | 480 |
| agtgtggaat atattgctcc aagccaaagc atcaaggttc ctcctcacac cattgcaagg | 540 |
| gtgactgctc tgctggatgt gaagaagatc aaggggaaga tgcacctcta ttcagagatt | 600 |
| ggcttgaaca aggattatgg ctatgacatg gtgccactgg tgtacaagta tggaggcccc | 660 |
| ttcaagtatg tcacccttgg aaccctctat gatgaaggct acaagcaagc tcagctggat | 720 |
| tacttcaaca tggggaatgt gattccagaa gagattgaaa ctgtttcaaa gagcaacaac | 780 |
| ccaaaccact tgctggcttc tggtgttggg atctttgaga gtgaatatgg aagtgtcttc | 840 |
| aatgtgaagg tggaatacat caacattaac accaagaaga ttgagaagac agagaatctc | 900 |
| accattgagc caaccattgt gccagtgaag cagaccaaca ccaagtaa | 948 |

<210> SEQ ID NO 13
<211> LENGTH: 948
<212> TYPE: DNA
<213> ORGANISM: Artificial Sequence
<220> FEATURE:
<223> OTHER INFORMATION: Variant: Axmi486-E275D T100N D96P

<400> SEQUENCE: 13

| | |
|---|---|
| atgctggctg ttgctgccaa gacagagaac aacaaggagc agcaagtgat cacccacttc | 60 |
| aaccagaggg agaacaagtt ccctgatgtt ggccaaggaa tccaatggct ctctcagttc | 120 |
| tatgggaaat cattgaagaa caatggagaa ggatattctc ttggccaaga gtgatgaga | 180 |
| tacttcttgg aggtgaagaa cagctatggg cagcttgcaa tggagcctca ggtcatctca | 240 |
| acaactcctc tctgggctgg ccaaagtgat ttggagaatg caacaccgca tgagcaaaat | 300 |
| ctcaactcaa cagagttcaa gaagacatac agcaacacca caacaacctc cacagagaat | 360 |
| ggcttcatga ttggccaaga aacagaaggg aaggttggga ttccctttgt tgctgaaggg | 420 |
| aaggtcacca tcaagacaga gtacaacttc aatcacacca tggctatga aacttcagag | 480 |
| agtgtggaat atattgctcc aagccaaagc atcaaggttc ctcctcacac cattgcaagg | 540 |
| gtgactgctc tgctggatgt gaagaagatc aaggggaaga tgcacctcta ttcagagatt | 600 |
| ggcttgaaca aggattatgg ctatgacatg gtgccactgg tgtacaagta tggaggcccc | 660 |
| ttcaagtatg tcacccttgg aaccctctat gatgaaggct acaagcaagc tcagctggat | 720 |
| tacttcaaca tggggaatgt gattccagaa gagattgaaa ctgtttcaaa gagcaacaac | 780 |
| ccaaaccact tgctggcttc tggtgttggg atctttgaga gtgattatgg aagtgtcttc | 840 |
| aatgtgaagg tggaatacat caacattaac accaagaaga ttgagaagac agagaatctc | 900 |
| accattgagc caaccattgt gccagtgaag cagaccaaca ccaagtaa | 948 |

<210> SEQ ID NO 14
<211> LENGTH: 948
<212> TYPE: DNA
<213> ORGANISM: Artificial Sequence
<220> FEATURE:
<223> OTHER INFORMATION: Variant: Axmi486-R60S E275D T100N D96P

<400> SEQUENCE: 14

```
atgctggctg ttgctgccaa gacagagaac aacaaggagc agcaagtgat cacccacttc      60
aaccagaggg agaacaagtt ccctgatgtt ggccaaggaa tccaatggct ctctcagttc     120
tatgggaaat cattgaagaa caatggagaa ggatattctc ttggccaaga tgtgatgagt     180
tacttcttgg aggtgaagaa cagctatggg cagcttgcaa tggagcctca ggtcatctca     240
acaactcctc tctgggctgg ccaaagtgat ttggagaatg caacaccgca tgagcaaaat     300
ctcaactcaa cagagttcaa gaagacatac agcaacacca caacaacctc cacagagaat     360
ggcttcatga ttggccaaga aacagaaggg aaggttggga ttccctttgt tgctgaaggg     420
aaggtcacca tcaagacaga gtacaacttc aatcacacca tggctatgaa acttcagag      480
agtgtggaat atattgctcc aagccaaagc atcaaggttc ctcctcacac cattgcaagg     540
gtgactgctc tgctggatgt gaagaagatc aaggggaaga tgcacctcta ttcagagatt     600
ggcttgaaca aggattatgg ctatgacatg gtgccactgg tgtacaagta tggaggcccc     660
ttcaagtatg tcacccttgg aaccctctat gatgaaggct acaagcaagc tcagctggat     720
tacttcaaca tggggaatgt gattccagaa gagattgaaa ctgtttcaaa gagcaacaac     780
ccaaaccact tgctggcttc tggtgttggg atctttgaga gtgattatgg aagtgtcttc     840
aatgtgaagg tggaatacat caacattaac accaagaaga ttgagaagac agagaatctc     900
accattgagc caaccattgt gccagtgaag cagaccaaca ccaagtaa                   948
```

<210> SEQ ID NO 15
<211> LENGTH: 948
<212> TYPE: DNA
<213> ORGANISM: Artificial Sequence
<220> FEATURE:
<223> OTHER INFORMATION: Variant: Axmi486-R60T E275D T100N D96P

<400> SEQUENCE: 15

```
atgctggctg ttgctgccaa gacagagaac aacaaggagc agcaagtgat cacccacttc      60
aaccagaggg agaacaagtt ccctgatgtt ggccaaggaa tccaatggct ctctcagttc     120
tatgggaaat cattgaagaa caatggagaa ggatattctc ttggccaaga tgtgatgacg     180
tacttcttgg aggtgaagaa cagctatggg cagcttgcaa tggagcctca ggtcatctca     240
acaactcctc tctgggctgg ccaaagtgat ttggagaatg caacaccgca tgagcaaaat     300
ctcaactcaa cagagttcaa gaagacatac agcaacacca caacaacctc cacagagaat     360
ggcttcatga ttggccaaga aacagaaggg aaggttggga ttccctttgt tgctgaaggg     420
aaggtcacca tcaagacaga gtacaacttc aatcacacca tggctatgaa acttcagag      480
agtgtggaat atattgctcc aagccaaagc atcaaggttc ctcctcacac cattgcaagg     540
gtgactgctc tgctggatgt gaagaagatc aaggggaaga tgcacctcta ttcagagatt     600
ggcttgaaca aggattatgg ctatgacatg gtgccactgg tgtacaagta tggaggcccc     660
ttcaagtatg tcacccttgg aaccctctat gatgaaggct acaagcaagc tcagctggat     720
tacttcaaca tggggaatgt gattccagaa gagattgaaa ctgtttcaaa gagcaacaac     780
ccaaaccact tgctggcttc tggtgttggg atctttgaga gtgattatgg aagtgtcttc     840
aatgtgaagg tggaatacat caacattaac accaagaaga ttgagaagac agagaatctc     900
accattgagc caaccattgt gccagtgaag cagaccaaca ccaagtaa                   948
```

<210> SEQ ID NO 16
<211> LENGTH: 315
<212> TYPE: PRT
<213> ORGANISM: Artificial Sequence
<220> FEATURE:
<223> OTHER INFORMATION: Variant: Axmi486-R60S

<400> SEQUENCE: 16

```
Met Leu Ala Val Ala Ala Lys Thr Glu Asn Asn Lys Glu Gln Gln Val
1               5                   10                  15

Ile Thr His Phe Asn Gln Arg Glu Asn Lys Phe Pro Asp Val Gly Gln
            20                  25                  30

Gly Ile Gln Trp Leu Ser Gln Phe Tyr Gly Lys Ser Leu Lys Asn Asn
        35                  40                  45

Gly Glu Gly Tyr Ser Leu Gly Gln Asp Val Met Ser Tyr Phe Leu Glu
    50                  55                  60

Val Lys Asn Ser Tyr Gly Gln Leu Ala Met Glu Pro Gln Val Ile Ser
65                  70                  75                  80

Thr Thr Pro Leu Trp Ala Gly Gln Ser Asp Leu Glu Asn Ala Thr Asp
                85                  90                  95

His Glu Gln Thr Leu Asn Ser Thr Glu Phe Lys Lys Thr Tyr Ser Asn
            100                 105                 110

Thr Thr Thr Thr Ser Thr Glu Asn Gly Phe Met Ile Gly Gln Glu Thr
        115                 120                 125

Glu Gly Lys Val Gly Ile Pro Phe Val Ala Glu Gly Lys Val Thr Ile
    130                 135                 140

Lys Thr Glu Tyr Asn Phe Asn His Thr Asn Gly Tyr Glu Thr Ser Glu
145                 150                 155                 160

Ser Val Glu Tyr Ile Ala Pro Ser Gln Ser Ile Lys Val Pro Pro His
                165                 170                 175

Thr Ile Ala Arg Val Thr Ala Leu Leu Asp Val Lys Lys Ile Lys Gly
            180                 185                 190

Lys Met His Leu Tyr Ser Glu Ile Gly Leu Asn Lys Asp Tyr Gly Tyr
        195                 200                 205

Asp Met Val Pro Leu Val Tyr Lys Tyr Gly Gly Pro Phe Lys Tyr Val
    210                 215                 220

Thr Leu Gly Thr Leu Tyr Asp Glu Gly Tyr Lys Gln Ala Gln Leu Asp
225                 230                 235                 240

Tyr Phe Asn Met Gly Asn Val Ile Pro Glu Glu Ile Glu Thr Val Ser
                245                 250                 255

Lys Ser Asn Asn Pro Asn His Leu Leu Ala Ser Gly Val Gly Ile Phe
            260                 265                 270

Glu Ser Glu Tyr Gly Ser Val Phe Asn Val Lys Val Gly Tyr Ile Asn
        275                 280                 285

Ile Asn Thr Lys Lys Ile Glu Lys Thr Glu Asn Leu Thr Ile Glu Pro
    290                 295                 300

Thr Ile Val Pro Val Lys Gln Thr Asn Thr Lys
305                 310                 315
```

<210> SEQ ID NO 17
<211> LENGTH: 315
<212> TYPE: PRT
<213> ORGANISM: Artificial Sequence
<220> FEATURE:
<223> OTHER INFORMATION: Variant: Axmi486-R60T

<400> SEQUENCE: 17

Met Leu Ala Val Ala Ala Lys Thr Glu Asn Asn Lys Glu Gln Gln Val
1               5                   10                  15

Ile Thr His Phe Asn Gln Arg Glu Asn Lys Phe Pro Asp Val Gly Gln
                20                  25                  30

Gly Ile Gln Trp Leu Ser Gln Phe Tyr Gly Lys Ser Leu Lys Asn Asn
            35                  40                  45

Gly Glu Gly Tyr Ser Leu Gly Gln Asp Val Met Thr Tyr Phe Leu Glu
50                  55                  60

Val Lys Asn Ser Tyr Gly Gln Leu Ala Met Glu Pro Gln Val Ile Ser
65                  70                  75                  80

Thr Thr Pro Leu Trp Ala Gly Gln Ser Asp Leu Glu Asn Ala Thr Asp
                85                  90                  95

His Glu Gln Thr Leu Asn Ser Thr Glu Phe Lys Lys Thr Tyr Ser Asn
                100                 105                 110

Thr Thr Thr Thr Ser Thr Glu Asn Gly Phe Met Ile Gly Gln Glu Thr
            115                 120                 125

Glu Gly Lys Val Gly Ile Pro Phe Val Ala Glu Gly Lys Val Thr Ile
130                 135                 140

Lys Thr Glu Tyr Asn Phe Asn His Thr Asn Gly Tyr Glu Thr Ser Glu
145                 150                 155                 160

Ser Val Glu Tyr Ile Ala Pro Ser Gln Ser Ile Lys Val Pro Pro His
                165                 170                 175

Thr Ile Ala Arg Val Thr Ala Leu Leu Asp Val Lys Lys Ile Lys Gly
                180                 185                 190

Lys Met His Leu Tyr Ser Glu Ile Gly Leu Asn Lys Asp Tyr Gly Tyr
                195                 200                 205

Asp Met Val Pro Leu Val Tyr Lys Tyr Gly Gly Pro Phe Lys Tyr Val
210                 215                 220

Thr Leu Gly Thr Leu Tyr Asp Glu Gly Tyr Lys Gln Ala Gln Leu Asp
225                 230                 235                 240

Tyr Phe Asn Met Gly Asn Val Ile Pro Glu Glu Ile Glu Thr Val Ser
                245                 250                 255

Lys Ser Asn Asn Pro Asn His Leu Leu Ala Ser Gly Val Gly Ile Phe
                260                 265                 270

Glu Ser Glu Tyr Gly Ser Val Phe Asn Val Lys Val Glu Tyr Ile Asn
                275                 280                 285

Ile Asn Thr Lys Lys Ile Glu Lys Thr Glu Asn Leu Thr Ile Glu Pro
                290                 295                 300

Thr Ile Val Pro Val Lys Gln Thr Asn Thr Lys
305                 310                 315

<210> SEQ ID NO 18
<211> LENGTH: 315
<212> TYPE: PRT
<213> ORGANISM: Artificial Sequence
<220> FEATURE:
<223> OTHER INFORMATION: Variant: Axmi486-E275D

<400> SEQUENCE: 18

Met Leu Ala Val Ala Ala Lys Thr Glu Asn Asn Lys Glu Gln Gln Val
1               5                   10                  15

Ile Thr His Phe Asn Gln Arg Glu Asn Lys Phe Pro Asp Val Gly Gln
                20                  25                  30

Gly Ile Gln Trp Leu Ser Gln Phe Tyr Gly Lys Ser Leu Lys Asn Asn
            35                  40                  45

Gly Glu Gly Tyr Ser Leu Gly Gln Asp Val Met Arg Tyr Phe Leu Glu
            50                  55                  60

Val Lys Asn Ser Tyr Gly Gln Leu Ala Met Glu Pro Gln Val Ile Ser
 65                  70                  75                  80

Thr Thr Pro Leu Trp Ala Gly Gln Ser Asp Leu Glu Asn Ala Thr Asp
                 85                  90                  95

His Glu Gln Thr Leu Asn Ser Thr Glu Phe Lys Lys Thr Tyr Ser Asn
            100                 105                 110

Thr Thr Thr Thr Ser Thr Glu Asn Gly Phe Met Ile Gly Gln Glu Thr
            115                 120                 125

Glu Gly Lys Val Gly Ile Pro Phe Val Ala Glu Gly Lys Val Thr Ile
130                 135                 140

Lys Thr Glu Tyr Asn Phe Asn His Thr Asn Gly Tyr Glu Thr Ser Glu
145                 150                 155                 160

Ser Val Glu Tyr Ile Ala Pro Ser Gln Ser Ile Lys Val Pro Pro His
                165                 170                 175

Thr Ile Ala Arg Val Thr Ala Leu Leu Asp Val Lys Lys Ile Lys Gly
            180                 185                 190

Lys Met His Leu Tyr Ser Glu Ile Gly Leu Asn Lys Asp Tyr Gly Tyr
            195                 200                 205

Asp Met Val Pro Leu Val Tyr Lys Tyr Gly Gly Pro Phe Lys Tyr Val
210                 215                 220

Thr Leu Gly Thr Leu Tyr Asp Glu Gly Tyr Lys Gln Ala Gln Leu Asp
225                 230                 235                 240

Tyr Phe Asn Met Gly Asn Val Ile Pro Glu Glu Ile Glu Thr Val Ser
                245                 250                 255

Lys Ser Asn Asn Pro Asn His Leu Leu Ala Ser Gly Val Gly Ile Phe
            260                 265                 270

Glu Ser Asp Tyr Gly Ser Val Phe Asn Val Lys Val Glu Tyr Ile Asn
            275                 280                 285

Ile Asn Thr Lys Lys Ile Glu Lys Thr Glu Asn Leu Thr Ile Glu Pro
290                 295                 300

Thr Ile Val Pro Val Lys Gln Thr Asn Thr Lys
305                 310                 315

<210> SEQ ID NO 19
<211> LENGTH: 315
<212> TYPE: PRT
<213> ORGANISM: Artificial Sequence
<220> FEATURE:
<223> OTHER INFORMATION: Variant: Axmi486-R60S E275D

<400> SEQUENCE: 19

Met Leu Ala Val Ala Ala Lys Thr Glu Asn Asn Lys Glu Gln Gln Val
 1               5                  10                  15

Ile Thr His Phe Asn Gln Arg Glu Asn Lys Phe Pro Asp Val Gly Gln
            20                  25                  30

Gly Ile Gln Trp Leu Ser Gln Phe Tyr Gly Lys Ser Leu Lys Asn Asn
        35                  40                  45

Gly Glu Gly Tyr Ser Leu Gly Gln Asp Val Met Ser Tyr Phe Leu Glu
    50                  55                  60

Val Lys Asn Ser Tyr Gly Gln Leu Ala Met Glu Pro Gln Val Ile Ser
 65                  70                  75                  80

Thr Thr Pro Leu Trp Ala Gly Gln Ser Asp Leu Glu Asn Ala Thr Asp
                 85                  90                  95

```
His Glu Gln Thr Leu Asn Ser Thr Glu Phe Lys Lys Thr Tyr Ser Asn
                100                 105                 110
Thr Thr Thr Thr Ser Thr Glu Asn Gly Phe Met Ile Gly Gln Glu Thr
            115                 120                 125
Glu Gly Lys Val Gly Ile Pro Phe Val Ala Glu Gly Lys Val Thr Ile
        130                 135                 140
Lys Thr Glu Tyr Asn Phe Asn His Thr Asn Gly Tyr Glu Thr Ser Glu
145                 150                 155                 160
Ser Val Glu Tyr Ile Ala Pro Ser Gln Ser Ile Lys Val Pro Pro His
                165                 170                 175
Thr Ile Ala Arg Val Thr Ala Leu Leu Asp Val Lys Lys Ile Lys Gly
            180                 185                 190
Lys Met His Leu Tyr Ser Glu Ile Gly Leu Asn Lys Asp Tyr Gly Tyr
        195                 200                 205
Asp Met Val Pro Leu Val Tyr Lys Tyr Gly Gly Pro Phe Lys Tyr Val
    210                 215                 220
Thr Leu Gly Thr Leu Tyr Asp Glu Gly Tyr Lys Gln Ala Gln Leu Asp
225                 230                 235                 240
Tyr Phe Asn Met Gly Asn Val Ile Pro Glu Glu Ile Glu Thr Val Ser
                245                 250                 255
Lys Ser Asn Asn Pro Asn His Leu Leu Ala Ser Gly Val Gly Ile Phe
            260                 265                 270
Glu Ser Asp Tyr Gly Ser Val Phe Asn Val Lys Val Glu Tyr Ile Asn
        275                 280                 285
Ile Asn Thr Lys Lys Ile Glu Lys Thr Glu Asn Leu Thr Ile Glu Pro
    290                 295                 300
Thr Ile Val Pro Val Lys Gln Thr Asn Thr Lys
305                 310                 315

<210> SEQ ID NO 20
<211> LENGTH: 315
<212> TYPE: PRT
<213> ORGANISM: Artificial Sequence
<220> FEATURE:
<223> OTHER INFORMATION: Variant: Axmi486-R60T E275D

<400> SEQUENCE: 20

Met Leu Ala Val Ala Ala Lys Thr Glu Asn Asn Lys Glu Gln Gln Val
1               5                   10                  15
Ile Thr His Phe Asn Gln Arg Glu Asn Lys Phe Pro Asp Val Gly Gln
            20                  25                  30
Gly Ile Gln Trp Leu Ser Gln Phe Tyr Gly Lys Ser Leu Lys Asn Asn
        35                  40                  45
Gly Glu Gly Tyr Ser Leu Gly Gln Asp Val Met Thr Tyr Phe Leu Glu
    50                  55                  60
Val Lys Asn Ser Tyr Gly Gln Leu Ala Met Glu Pro Gln Val Ile Ser
65                  70                  75                  80
Thr Thr Pro Leu Trp Ala Gly Gln Ser Asp Leu Glu Asn Ala Thr Asp
                85                  90                  95
His Glu Gln Thr Leu Asn Ser Thr Glu Phe Lys Lys Thr Tyr Ser Asn
            100                 105                 110
Thr Thr Thr Thr Ser Thr Glu Asn Gly Phe Met Ile Gly Gln Glu Thr
        115                 120                 125
Glu Gly Lys Val Gly Ile Pro Phe Val Ala Glu Gly Lys Val Thr Ile
    130                 135                 140
```

```
Lys Thr Glu Tyr Asn Phe Asn His Thr Asn Gly Tyr Glu Thr Ser Glu
145                 150                 155                 160

Ser Val Glu Tyr Ile Ala Pro Ser Gln Ser Ile Lys Val Pro Pro His
                165                 170                 175

Thr Ile Ala Arg Val Thr Ala Leu Leu Asp Val Lys Lys Ile Lys Gly
            180                 185                 190

Lys Met His Leu Tyr Ser Glu Ile Gly Leu Asn Lys Asp Tyr Gly Tyr
        195                 200                 205

Asp Met Val Pro Leu Val Tyr Lys Tyr Gly Gly Pro Phe Lys Tyr Val
    210                 215                 220

Thr Leu Gly Thr Leu Tyr Asp Glu Gly Tyr Lys Gln Ala Gln Leu Asp
225                 230                 235                 240

Tyr Phe Asn Met Gly Asn Val Ile Pro Glu Glu Ile Glu Thr Val Ser
                245                 250                 255

Lys Ser Asn Asn Pro Asn His Leu Leu Ala Ser Gly Val Gly Ile Phe
                260                 265                 270

Glu Ser Asp Tyr Gly Ser Val Phe Asn Val Lys Val Glu Tyr Ile Asn
            275                 280                 285

Ile Asn Thr Lys Lys Ile Glu Lys Thr Glu Asn Leu Thr Ile Glu Pro
        290                 295                 300

Thr Ile Val Pro Val Lys Gln Thr Asn Thr Lys
305                 310                 315

<210> SEQ ID NO 21
<211> LENGTH: 315
<212> TYPE: PRT
<213> ORGANISM: Artificial Sequence
<220> FEATURE:
<223> OTHER INFORMATION: Variant: Axmi486-R60S H97L T100N D96P

<400> SEQUENCE: 21

Met Leu Ala Val Ala Ala Lys Thr Glu Asn Asn Lys Glu Gln Gln Val
1               5                   10                  15

Ile Thr His Phe Asn Gln Arg Glu Asn Lys Phe Pro Asp Val Gly Gln
            20                  25                  30

Gly Ile Gln Trp Leu Ser Gln Phe Tyr Gly Lys Ser Leu Lys Asn Asn
        35                  40                  45

Gly Glu Gly Tyr Ser Leu Gly Gln Asp Val Met Ser Tyr Phe Leu Glu
    50                  55                  60

Val Lys Asn Ser Tyr Gly Gln Leu Ala Met Glu Pro Gln Val Ile Ser
65                  70                  75                  80

Thr Thr Pro Leu Trp Ala Gly Gln Ser Asp Leu Glu Asn Ala Thr Pro
                85                  90                  95

Leu Glu Gln Asn Leu Asn Ser Thr Glu Phe Lys Lys Thr Tyr Ser Asn
                100                 105                 110

Thr Thr Thr Thr Ser Thr Glu Asn Gly Phe Met Ile Gly Gln Glu Thr
            115                 120                 125

Glu Gly Lys Val Gly Ile Pro Phe Val Ala Glu Gly Lys Val Thr Ile
        130                 135                 140

Lys Thr Glu Tyr Asn Phe Asn His Thr Asn Gly Tyr Glu Thr Ser Glu
145                 150                 155                 160

Ser Val Glu Tyr Ile Ala Pro Ser Gln Ser Ile Lys Val Pro Pro His
                165                 170                 175

Thr Ile Ala Arg Val Thr Ala Leu Leu Asp Val Lys Lys Ile Lys Gly
            180                 185                 190
```

Lys Met His Leu Tyr Ser Glu Ile Gly Leu Asn Lys Asp Tyr Gly Tyr
            195                 200                 205

Asp Met Val Pro Leu Val Tyr Lys Tyr Gly Gly Pro Phe Lys Tyr Val
            210                 215                 220

Thr Leu Gly Thr Leu Tyr Asp Glu Gly Tyr Lys Gln Ala Gln Leu Asp
225                 230                 235                 240

Tyr Phe Asn Met Gly Asn Val Ile Pro Glu Glu Ile Glu Thr Val Ser
                245                 250                 255

Lys Ser Asn Asn Pro Asn His Leu Leu Ala Ser Gly Val Gly Ile Phe
                260                 265                 270

Glu Ser Glu Tyr Gly Ser Val Phe Asn Val Lys Val Glu Tyr Ile Asn
                275                 280                 285

Ile Asn Thr Lys Lys Ile Glu Lys Thr Glu Asn Leu Thr Ile Glu Pro
                290                 295                 300

Thr Ile Val Pro Val Lys Gln Thr Asn Thr Lys
305                 310                 315

<210> SEQ ID NO 22
<211> LENGTH: 315
<212> TYPE: PRT
<213> ORGANISM: Artificial Sequence
<220> FEATURE:
<223> OTHER INFORMATION: Variant: Axmi486-R60T H97L T100N D96P

<400> SEQUENCE: 22

Met Leu Ala Val Ala Ala Lys Thr Glu Asn Asn Lys Glu Gln Gln Val
1               5                   10                  15

Ile Thr His Phe Asn Gln Arg Glu Asn Lys Phe Pro Asp Val Gly Gln
            20                  25                  30

Gly Ile Gln Trp Leu Ser Gln Phe Tyr Gly Lys Ser Leu Lys Asn Asn
        35                  40                  45

Gly Glu Gly Tyr Ser Leu Gly Gln Asp Val Met Thr Tyr Phe Leu Glu
    50                  55                  60

Val Lys Asn Ser Tyr Gly Gln Leu Ala Met Glu Pro Gln Val Ile Ser
65                  70                  75                  80

Thr Thr Pro Leu Trp Ala Gly Gln Ser Asp Leu Glu Asn Ala Thr Pro
                85                  90                  95

Leu Glu Gln Asn Leu Asn Ser Thr Glu Phe Lys Lys Thr Tyr Ser Asn
                100                 105                 110

Thr Thr Thr Thr Ser Thr Glu Asn Gly Phe Met Ile Gly Gln Glu Thr
            115                 120                 125

Glu Gly Lys Val Gly Ile Pro Phe Val Ala Glu Gly Lys Val Thr Ile
        130                 135                 140

Lys Thr Glu Tyr Asn Phe Asn His Thr Asn Gly Tyr Glu Thr Ser Glu
145                 150                 155                 160

Ser Val Glu Tyr Ile Ala Pro Ser Gln Ser Ile Lys Val Pro Pro His
                165                 170                 175

Thr Ile Ala Arg Val Thr Ala Leu Leu Asp Val Lys Lys Ile Lys Gly
            180                 185                 190

Lys Met His Leu Tyr Ser Glu Ile Gly Leu Asn Lys Asp Tyr Gly Tyr
            195                 200                 205

Asp Met Val Pro Leu Val Tyr Lys Tyr Gly Gly Pro Phe Lys Tyr Val
            210                 215                 220

Thr Leu Gly Thr Leu Tyr Asp Glu Gly Tyr Lys Gln Ala Gln Leu Asp
225                 230                 235                 240

```
Tyr Phe Asn Met Gly Asn Val Ile Pro Glu Glu Ile Glu Thr Val Ser
            245                 250                 255

Lys Ser Asn Asn Pro Asn His Leu Leu Ala Ser Gly Val Gly Ile Phe
        260                 265                 270

Glu Ser Glu Tyr Gly Ser Val Phe Asn Val Lys Val Gly Tyr Ile Asn
        275                 280                 285

Ile Asn Thr Lys Lys Ile Glu Lys Thr Glu Asn Leu Thr Ile Glu Pro
        290                 295                 300

Thr Ile Val Pro Val Lys Gln Thr Asn Thr Lys
305                 310                 315
```

<210> SEQ ID NO 23
<211> LENGTH: 315
<212> TYPE: PRT
<213> ORGANISM: Artificial Sequence
<220> FEATURE:
<223> OTHER INFORMATION: Variant: Axmi486-E275D H97L T100N D96P

<400> SEQUENCE: 23

```
Met Leu Ala Val Ala Ala Lys Thr Glu Asn Asn Lys Glu Gln Gln Val
1               5                   10                  15

Ile Thr His Phe Asn Gln Arg Glu Asn Lys Phe Pro Asp Val Gly Gln
            20                  25                  30

Gly Ile Gln Trp Leu Ser Gln Phe Tyr Gly Lys Ser Leu Lys Asn Asn
        35                  40                  45

Gly Glu Gly Tyr Ser Leu Gly Gln Asp Val Met Arg Tyr Phe Leu Glu
    50                  55                  60

Val Lys Asn Ser Tyr Gly Gln Leu Ala Met Glu Pro Gln Val Ile Ser
65              70                  75                  80

Thr Thr Pro Leu Trp Ala Gly Gln Ser Asp Leu Glu Asn Ala Thr Pro
                85                  90                  95

Leu Glu Gln Asn Leu Asn Ser Thr Glu Phe Lys Lys Thr Tyr Ser Asn
            100                 105                 110

Thr Thr Thr Thr Ser Thr Glu Asn Gly Phe Met Ile Gly Gln Glu Thr
        115                 120                 125

Glu Gly Lys Val Gly Ile Pro Phe Val Ala Glu Gly Lys Val Thr Ile
    130                 135                 140

Lys Thr Glu Tyr Asn Phe Asn His Thr Asn Gly Tyr Glu Thr Ser Glu
145                 150                 155                 160

Ser Val Glu Tyr Ile Ala Pro Ser Gln Ser Ile Lys Val Pro Pro His
                165                 170                 175

Thr Ile Ala Arg Val Thr Ala Leu Leu Asp Val Lys Lys Ile Lys Gly
            180                 185                 190

Lys Met His Leu Tyr Ser Glu Ile Gly Leu Asn Lys Asp Tyr Gly Tyr
        195                 200                 205

Asp Met Val Pro Leu Val Tyr Lys Tyr Gly Gly Pro Phe Lys Tyr Val
    210                 215                 220

Thr Leu Gly Thr Leu Tyr Asp Glu Gly Tyr Lys Gln Ala Gln Leu Asp
225                 230                 235                 240

Tyr Phe Asn Met Gly Asn Val Ile Pro Glu Glu Ile Glu Thr Val Ser
                245                 250                 255

Lys Ser Asn Asn Pro Asn His Leu Leu Ala Ser Gly Val Gly Ile Phe
            260                 265                 270

Glu Ser Asp Tyr Gly Ser Val Phe Asn Val Lys Val Glu Tyr Ile Asn
        275                 280                 285
```

Ile Asn Thr Lys Lys Ile Glu Lys Thr Glu Asn Leu Thr Ile Glu Pro
            290                 295                 300

Thr Ile Val Pro Val Lys Gln Thr Asn Thr Lys
305                 310                 315

<210> SEQ ID NO 24
<211> LENGTH: 315
<212> TYPE: PRT
<213> ORGANISM: Artificial Sequence
<220> FEATURE:
<223> OTHER INFORMATION: Variant: Axmi486-R60S E275D H97L T100N D96P

<400> SEQUENCE: 24

Met Leu Ala Val Ala Ala Lys Thr Glu Asn Asn Lys Glu Gln Gln Val
1               5                   10                  15

Ile Thr His Phe Asn Gln Arg Glu Asn Lys Phe Pro Asp Val Gly Gln
                20                  25                  30

Gly Ile Gln Trp Leu Ser Gln Phe Tyr Gly Lys Ser Leu Lys Asn Asn
            35                  40                  45

Gly Glu Gly Tyr Ser Leu Gly Gln Asp Val Met Ser Tyr Phe Leu Glu
    50                  55                  60

Val Lys Asn Ser Tyr Gly Gln Leu Ala Met Glu Pro Gln Val Ile Ser
65                  70                  75                  80

Thr Thr Pro Leu Trp Ala Gly Gln Ser Asp Leu Glu Asn Ala Thr Pro
                85                  90                  95

Leu Glu Gln Asn Leu Asn Ser Thr Glu Phe Lys Lys Thr Tyr Ser Asn
            100                 105                 110

Thr Thr Thr Thr Ser Thr Glu Asn Gly Phe Met Ile Gly Gln Glu Thr
    115                 120                 125

Glu Gly Lys Val Gly Ile Pro Phe Val Ala Glu Gly Lys Val Thr Ile
130                 135                 140

Lys Thr Glu Tyr Asn Phe Asn His Thr Asn Gly Tyr Glu Thr Ser Glu
145                 150                 155                 160

Ser Val Glu Tyr Ile Ala Pro Ser Gln Ser Ile Lys Val Pro Pro His
                165                 170                 175

Thr Ile Ala Arg Val Thr Ala Leu Leu Asp Val Lys Lys Ile Lys Gly
            180                 185                 190

Lys Met His Leu Tyr Ser Glu Ile Gly Leu Asn Lys Asp Tyr Gly Tyr
    195                 200                 205

Asp Met Val Pro Leu Val Tyr Lys Tyr Gly Gly Pro Phe Lys Tyr Val
210                 215                 220

Thr Leu Gly Thr Leu Tyr Asp Glu Gly Tyr Lys Gln Ala Gln Leu Asp
225                 230                 235                 240

Tyr Phe Asn Met Gly Asn Val Ile Pro Glu Glu Ile Glu Thr Val Ser
                245                 250                 255

Lys Ser Asn Asn Pro Asn His Leu Leu Ala Ser Gly Val Gly Ile Phe
            260                 265                 270

Glu Ser Asp Tyr Gly Ser Val Phe Asn Val Lys Val Glu Tyr Ile Asn
    275                 280                 285

Ile Asn Thr Lys Lys Ile Glu Lys Thr Glu Asn Leu Thr Ile Glu Pro
            290                 295                 300

Thr Ile Val Pro Val Lys Gln Thr Asn Thr Lys
305                 310                 315

<210> SEQ ID NO 25

<211> LENGTH: 315
<212> TYPE: PRT
<213> ORGANISM: Artificial Sequence
<220> FEATURE:
<223> OTHER INFORMATION: Variant: Axmi486-R60T E275D H97L T100N D96P

<400> SEQUENCE: 25

```
Met Leu Ala Val Ala Ala Lys Thr Glu Asn Asn Lys Glu Gln Gln Val
1               5                   10                  15

Ile Thr His Phe Asn Gln Arg Glu Asn Lys Phe Pro Asp Val Gly Gln
            20                  25                  30

Gly Ile Gln Trp Leu Ser Gln Phe Tyr Gly Lys Ser Leu Lys Asn Asn
        35                  40                  45

Gly Glu Gly Tyr Ser Leu Gly Gln Asp Val Met Thr Tyr Phe Leu Glu
50                  55                  60

Val Lys Asn Ser Tyr Gly Gln Leu Ala Met Glu Pro Gln Val Ile Ser
65                  70                  75                  80

Thr Thr Pro Leu Trp Ala Gly Gln Ser Asp Leu Glu Asn Ala Thr Pro
                85                  90                  95

Leu Glu Gln Asn Leu Asn Ser Thr Glu Phe Lys Lys Thr Tyr Ser Asn
            100                 105                 110

Thr Thr Thr Thr Ser Thr Glu Asn Gly Phe Met Ile Gly Gln Glu Thr
        115                 120                 125

Glu Gly Lys Val Gly Ile Pro Phe Val Ala Glu Gly Lys Val Thr Ile
130                 135                 140

Lys Thr Glu Tyr Asn Phe Asn His Thr Asn Gly Tyr Glu Thr Ser Glu
145                 150                 155                 160

Ser Val Glu Tyr Ile Ala Pro Ser Gln Ser Ile Lys Val Pro Pro His
                165                 170                 175

Thr Ile Ala Arg Val Thr Ala Leu Leu Asp Val Lys Lys Ile Lys Gly
            180                 185                 190

Lys Met His Leu Tyr Ser Glu Ile Gly Leu Asn Lys Asp Tyr Gly Tyr
        195                 200                 205

Asp Met Val Pro Leu Val Tyr Lys Tyr Gly Gly Pro Phe Lys Tyr Val
210                 215                 220

Thr Leu Gly Thr Leu Tyr Asp Glu Gly Tyr Lys Gln Ala Gln Leu Asp
225                 230                 235                 240

Tyr Phe Asn Met Gly Asn Val Ile Pro Glu Glu Ile Glu Thr Val Ser
                245                 250                 255

Lys Ser Asn Asn Pro Asn His Leu Leu Ala Ser Gly Val Gly Ile Phe
            260                 265                 270

Glu Ser Asp Tyr Gly Ser Val Phe Asn Val Lys Val Glu Tyr Ile Asn
        275                 280                 285

Ile Asn Thr Lys Lys Ile Glu Lys Thr Glu Asn Leu Thr Ile Glu Pro
290                 295                 300

Thr Ile Val Pro Val Lys Gln Thr Asn Thr Lys
305                 310                 315
```

<210> SEQ ID NO 26
<211> LENGTH: 315
<212> TYPE: PRT
<213> ORGANISM: Artificial Sequence
<220> FEATURE:
<223> OTHER INFORMATION: Variant: Axmi486-R60S T100N D96P

<400> SEQUENCE: 26

Met Leu Ala Val Ala Ala Lys Thr Glu Asn Asn Lys Glu Gln Gln Val

```
                1               5                   10                  15
            Ile Thr His Phe Asn Gln Arg Glu Asn Lys Phe Pro Asp Val Gly Gln
                            20                  25                  30

Gly Ile Gln Trp Leu Ser Gln Phe Tyr Gly Lys Ser Leu Lys Asn Asn
                            35                  40                  45

Gly Glu Gly Tyr Ser Leu Gly Gln Asp Val Met Ser Tyr Phe Leu Glu
                            50                  55                  60

Val Lys Asn Ser Tyr Gly Gln Leu Ala Met Glu Pro Gln Val Ile Ser
            65                  70                  75                  80

Thr Thr Pro Leu Trp Ala Gly Gln Ser Asp Leu Glu Asn Ala Thr Pro
                            85                  90                  95

His Glu Gln Asn Leu Asn Ser Thr Glu Phe Lys Lys Thr Tyr Ser Asn
                            100                 105                 110

Thr Thr Thr Thr Ser Thr Glu Asn Gly Phe Met Ile Gly Gln Glu Thr
                            115                 120                 125

Glu Gly Lys Val Gly Ile Pro Phe Val Ala Glu Gly Lys Val Thr Ile
                            130                 135                 140

Lys Thr Glu Tyr Asn Phe Asn His Thr Asn Gly Tyr Glu Thr Ser Glu
            145                 150                 155                 160

Ser Val Glu Tyr Ile Ala Pro Ser Gln Ser Ile Lys Val Pro Pro His
                            165                 170                 175

Thr Ile Ala Arg Val Thr Ala Leu Leu Asp Val Lys Lys Ile Lys Gly
                            180                 185                 190

Lys Met His Leu Tyr Ser Glu Ile Gly Leu Asn Lys Asp Tyr Gly Tyr
                            195                 200                 205

Asp Met Val Pro Leu Val Tyr Lys Tyr Gly Gly Pro Phe Lys Tyr Val
                            210                 215                 220

Thr Leu Gly Thr Leu Tyr Asp Glu Gly Tyr Lys Gln Ala Gln Leu Asp
            225                 230                 235                 240

Tyr Phe Asn Met Gly Asn Val Ile Pro Glu Glu Ile Glu Thr Val Ser
                            245                 250                 255

Lys Ser Asn Asn Pro Asn His Leu Leu Ala Ser Gly Val Gly Ile Phe
                            260                 265                 270

Glu Ser Glu Tyr Gly Ser Val Phe Asn Val Lys Val Glu Tyr Ile Asn
                            275                 280                 285

Ile Asn Thr Lys Lys Ile Glu Lys Thr Glu Asn Leu Thr Ile Glu Pro
                            290                 295                 300

Thr Ile Val Pro Val Lys Gln Thr Asn Thr Lys
            305                 310                 315

<210> SEQ ID NO 27
<211> LENGTH: 315
<212> TYPE: PRT
<213> ORGANISM: Artificial Sequence
<220> FEATURE:
<223> OTHER INFORMATION: Variant: Axmi486-R60T T100N D96P

<400> SEQUENCE: 27

Met Leu Ala Val Ala Ala Lys Thr Glu Asn Asn Lys Glu Gln Gln Val
            1               5                   10                  15

Ile Thr His Phe Asn Gln Arg Glu Asn Lys Phe Pro Asp Val Gly Gln
                            20                  25                  30

Gly Ile Gln Trp Leu Ser Gln Phe Tyr Gly Lys Ser Leu Lys Asn Asn
                            35                  40                  45

Gly Glu Gly Tyr Ser Leu Gly Gln Asp Val Met Thr Tyr Phe Leu Glu
```

```
                50                  55                  60
Val Lys Asn Ser Tyr Gly Gln Leu Ala Met Glu Pro Gln Val Ile Ser
 65                  70                  75                  80

Thr Thr Pro Leu Trp Ala Gly Gln Ser Asp Leu Glu Asn Ala Thr Pro
                 85                  90                  95

His Glu Gln Asn Leu Asn Ser Thr Glu Phe Lys Lys Thr Tyr Ser Asn
            100                 105                 110

Thr Thr Thr Thr Ser Thr Glu Asn Gly Phe Met Ile Gly Gln Glu Thr
        115                 120                 125

Glu Gly Lys Val Gly Ile Pro Phe Val Ala Glu Gly Lys Val Thr Ile
130                 135                 140

Lys Thr Glu Tyr Asn Phe Asn His Thr Asn Gly Tyr Glu Thr Ser Glu
145                 150                 155                 160

Ser Val Glu Tyr Ile Ala Pro Ser Gln Ser Ile Lys Val Pro Pro His
                165                 170                 175

Thr Ile Ala Arg Val Thr Ala Leu Leu Asp Val Lys Lys Ile Lys Gly
            180                 185                 190

Lys Met His Leu Tyr Ser Glu Ile Gly Leu Asn Lys Asp Tyr Gly Tyr
        195                 200                 205

Asp Met Val Pro Leu Val Tyr Lys Tyr Gly Gly Pro Phe Lys Tyr Val
    210                 215                 220

Thr Leu Gly Thr Leu Tyr Asp Glu Gly Tyr Lys Gln Ala Gln Leu Asp
225                 230                 235                 240

Tyr Phe Asn Met Gly Asn Val Ile Pro Glu Glu Ile Glu Thr Val Ser
                245                 250                 255

Lys Ser Asn Asn Pro Asn His Leu Leu Ala Ser Gly Val Gly Ile Phe
            260                 265                 270

Glu Ser Glu Tyr Gly Ser Val Phe Asn Val Lys Val Glu Tyr Ile Asn
        275                 280                 285

Ile Asn Thr Lys Lys Ile Glu Lys Thr Glu Asn Leu Thr Ile Glu Pro
    290                 295                 300

Thr Ile Val Pro Val Lys Gln Thr Asn Thr Lys
305                 310                 315

<210> SEQ ID NO 28
<211> LENGTH: 315
<212> TYPE: PRT
<213> ORGANISM: Artificial Sequence
<220> FEATURE:
<223> OTHER INFORMATION: Variant: Axmi486-E275D T100N D96P

<400> SEQUENCE: 28

Met Leu Ala Val Ala Ala Lys Thr Glu Asn Asn Lys Glu Gln Gln Val
 1               5                  10                  15

Ile Thr His Phe Asn Gln Arg Glu Asn Lys Phe Pro Asp Val Gly Gln
             20                  25                  30

Gly Ile Gln Trp Leu Ser Gln Phe Tyr Gly Lys Ser Leu Lys Asn Asn
         35                  40                  45

Gly Glu Gly Tyr Ser Leu Gly Gln Asp Val Met Arg Tyr Phe Leu Glu
     50                  55                  60

Val Lys Asn Ser Tyr Gly Gln Leu Ala Met Glu Pro Gln Val Ile Ser
 65                  70                  75                  80

Thr Thr Pro Leu Trp Ala Gly Gln Ser Asp Leu Glu Asn Ala Thr Pro
                 85                  90                  95

His Glu Gln Asn Leu Asn Ser Thr Glu Phe Lys Lys Thr Tyr Ser Asn
            100                 105                 110
```

```
                100             105             110
Thr Thr Thr Thr Ser Thr Glu Asn Gly Phe Met Ile Gly Gln Glu Thr
            115                 120                 125
Glu Gly Lys Val Gly Ile Pro Phe Val Ala Glu Gly Lys Val Thr Ile
        130                 135                 140
Lys Thr Glu Tyr Asn Phe Asn His Thr Asn Gly Tyr Glu Thr Ser Glu
145                 150                 155                 160
Ser Val Glu Tyr Ile Ala Pro Ser Gln Ser Ile Lys Val Pro Pro His
                165                 170                 175
Thr Ile Ala Arg Val Thr Ala Leu Leu Asp Val Lys Lys Ile Lys Gly
            180                 185                 190
Lys Met His Leu Tyr Ser Glu Ile Gly Leu Asn Lys Asp Tyr Gly Tyr
        195                 200                 205
Asp Met Val Pro Leu Val Tyr Lys Tyr Gly Pro Phe Lys Tyr Val
    210                 215                 220
Thr Leu Gly Thr Leu Tyr Asp Glu Gly Tyr Lys Gln Ala Gln Leu Asp
225                 230                 235                 240
Tyr Phe Asn Met Gly Asn Val Ile Pro Glu Glu Ile Glu Thr Val Ser
                245                 250                 255
Lys Ser Asn Asn Pro Asn His Leu Leu Ala Ser Gly Val Gly Ile Phe
            260                 265                 270
Glu Ser Asp Tyr Gly Ser Val Phe Asn Val Lys Val Gly Tyr Ile Asn
        275                 280                 285
Ile Asn Thr Lys Lys Ile Glu Lys Thr Glu Asn Leu Thr Ile Glu Pro
    290                 295                 300
Thr Ile Val Pro Val Lys Gln Thr Asn Thr Lys
305                 310                 315

<210> SEQ ID NO 29
<211> LENGTH: 315
<212> TYPE: PRT
<213> ORGANISM: Artificial Sequence
<220> FEATURE:
<223> OTHER INFORMATION: Variant: Axmi486-R60S E275D T100N D96P

<400> SEQUENCE: 29

Met Leu Ala Val Ala Ala Lys Thr Glu Asn Asn Lys Glu Gln Gln Val
1               5                   10                  15
Ile Thr His Phe Asn Gln Arg Glu Asn Lys Phe Pro Asp Val Gly Gln
            20                  25                  30
Gly Ile Gln Trp Leu Ser Gln Phe Tyr Gly Lys Ser Leu Lys Asn Asn
        35                  40                  45
Gly Glu Gly Tyr Ser Leu Gly Gln Asp Val Met Ser Tyr Phe Leu Glu
    50                  55                  60
Val Lys Asn Ser Tyr Gly Gln Leu Ala Met Glu Pro Gln Val Ile Ser
65                  70                  75                  80
Thr Thr Pro Leu Trp Ala Gly Gln Ser Asp Leu Glu Asn Ala Thr Pro
                85                  90                  95
His Glu Gln Asn Leu Asn Ser Thr Glu Phe Lys Lys Thr Tyr Ser Asn
            100                 105                 110
Thr Thr Thr Thr Ser Thr Glu Asn Gly Phe Met Ile Gly Gln Glu Thr
        115                 120                 125
Glu Gly Lys Val Gly Ile Pro Phe Val Ala Glu Gly Lys Val Thr Ile
    130                 135                 140
Lys Thr Glu Tyr Asn Phe Asn His Thr Asn Gly Tyr Glu Thr Ser Glu
```

145             150             155             160

Ser Val Glu Tyr Ile Ala Pro Ser Gln Ser Ile Lys Val Pro Pro His
                165             170             175

Thr Ile Ala Arg Val Thr Ala Leu Leu Asp Val Lys Lys Ile Lys Gly
                180             185             190

Lys Met His Leu Tyr Ser Glu Ile Gly Leu Asn Lys Asp Tyr Gly Tyr
                195             200             205

Asp Met Val Pro Leu Val Tyr Lys Tyr Gly Pro Phe Lys Tyr Val
210             215             220

Thr Leu Gly Thr Leu Tyr Asp Glu Gly Tyr Lys Gln Ala Gln Leu Asp
225             230             235             240

Tyr Phe Asn Met Gly Asn Val Ile Pro Glu Glu Ile Glu Thr Val Ser
                245             250             255

Lys Ser Asn Asn Pro Asn His Leu Leu Ala Ser Gly Val Gly Ile Phe
                260             265             270

Glu Ser Asp Tyr Gly Ser Val Phe Asn Val Lys Val Glu Tyr Ile Asn
                275             280             285

Ile Asn Thr Lys Lys Ile Glu Lys Thr Glu Asn Leu Thr Ile Glu Pro
                290             295             300

Thr Ile Val Pro Val Lys Gln Thr Asn Thr Lys
305             310             315

<210> SEQ ID NO 30
<211> LENGTH: 315
<212> TYPE: PRT
<213> ORGANISM: Artificial Sequence
<220> FEATURE:
<223> OTHER INFORMATION: Variant: Axmi486-R60T E275D T100N D96P

<400> SEQUENCE: 30

Met Leu Ala Val Ala Ala Lys Thr Glu Asn Asn Lys Glu Gln Gln Val
1               5               10              15

Ile Thr His Phe Asn Gln Arg Glu Asn Lys Phe Pro Asp Val Gly Gln
                20              25              30

Gly Ile Gln Trp Leu Ser Gln Phe Tyr Gly Lys Ser Leu Lys Asn Asn
                35              40              45

Gly Glu Gly Tyr Ser Leu Gly Gln Asp Val Met Thr Tyr Phe Leu Glu
                50              55              60

Val Lys Asn Ser Tyr Gly Gln Leu Ala Met Glu Pro Gln Val Ile Ser
65              70              75              80

Thr Thr Pro Leu Trp Ala Gly Gln Ser Asp Leu Glu Asn Ala Thr Pro
                85              90              95

His Glu Gln Asn Leu Asn Ser Thr Glu Phe Lys Lys Thr Tyr Ser Asn
                100             105             110

Thr Thr Thr Thr Ser Thr Glu Asn Gly Phe Met Ile Gly Gln Glu Thr
                115             120             125

Glu Gly Lys Val Gly Ile Pro Phe Val Ala Glu Gly Lys Val Thr Ile
                130             135             140

Lys Thr Glu Tyr Asn Phe Asn His Thr Asn Gly Tyr Glu Thr Ser Glu
145             150             155             160

Ser Val Glu Tyr Ile Ala Pro Ser Gln Ser Ile Lys Val Pro Pro His
                165             170             175

Thr Ile Ala Arg Val Thr Ala Leu Leu Asp Val Lys Lys Ile Lys Gly
                180             185             190

Lys Met His Leu Tyr Ser Glu Ile Gly Leu Asn Lys Asp Tyr Gly Tyr

```
          195                 200                 205
Asp Met Val Pro Leu Val Tyr Lys Tyr Gly Gly Pro Phe Lys Tyr Val
    210                 215                 220

Thr Leu Gly Thr Leu Tyr Asp Glu Gly Tyr Lys Gln Ala Gln Leu Asp
225                 230                 235                 240

Tyr Phe Asn Met Gly Asn Val Ile Pro Glu Ile Glu Thr Val Ser
                245                 250                 255

Lys Ser Asn Asn Pro Asn His Leu Leu Ala Ser Gly Val Gly Ile Phe
                260                 265                 270

Glu Ser Asp Tyr Gly Ser Val Phe Asn Val Lys Val Glu Tyr Ile Asn
                275                 280                 285

Ile Asn Thr Lys Lys Ile Glu Lys Thr Glu Asn Leu Thr Ile Glu Pro
    290                 295                 300

Thr Ile Val Pro Val Lys Gln Thr Asn Thr Lys
305                 310                 315
```

<210> SEQ ID NO 31
<211> LENGTH: 1023
<212> TYPE: DNA
<213> ORGANISM: Bacillus thuringiensis
<220> FEATURE:
<223> OTHER INFORMATION: axmi-486 (Ref: WO/2015/088937)

<400> SEQUENCE: 31

```
gtgagggaga aggatttgaa taaaaaagta acaaaggcag tattaagcat gatagtgggt      60
ataagtgttt tagcatctcc tttagctgta gccgcaaaaa cagagaataa taagaacaa     120
caagtaatta cacattttaa tcagagagaa ataagttcc ctgatgtagg acaggggatt     180
caatggttat ctcaatttta tggaaagtct ttaaagaata atggtgaagg atactcctta     240
ggtcaggatg taatgagata ttttttagaa gtaaagaatt cttacggtca attggcaatg     300
gaacctcaag taataagcac tacacctctt tgggccggcc aaagtgactt ggaaaatgca     360
actgatcatg aacaaacttt aaattccaca gaatttaaaa aacgtattc taacacaaca     420
accacctcta cagaaaatgg atttatgata ggtcaagaga ctgaaggaa agttggtatt     480
cccttgtcg cagaaggaaa agtcaccata aaaactgaat ataactttaa tcatactaat     540
gggtatgaaa catctgaaag tgtagagtat attgctcctt ctcaatctat taggtacca     600
ccgcatacta ttgcccgagt gacagcatta ttagatgtga aaaaaatcaa agggaaaatg     660
catctatatt cagaaattgg gcttaataaa gattatggtt acgatatggt gccacttgtt     720
tataaatatg gaggtccatt taagtatgta accttaggca cattatatga cgagggctat     780
aagcaggcac aattagatta tttcaatatg ggaaatgtta taccggaaga aattgagact     840
gtttcaaaaa gtaacaatcc caaccattta ttagcaagtg gagtaggaat ctttgaatca     900
gaatacggaa gtgtatttaa tgttaaagtt gaatacatta atattaatac gaaaaagatt     960
gaaaaaacag agaatcttac tattgaacct acaatagtcc ctgttaaaca gacgaataca    1020
aaa                                                                  1023
```

<210> SEQ ID NO 32
<211> LENGTH: 341
<212> TYPE: PRT
<213> ORGANISM: Bacillus thuringiensis
<220> FEATURE:
<223> OTHER INFORMATION: axmi-486 (Ref: WO/2015/088937)

<400> SEQUENCE: 32

```
Met Arg Glu Lys Asp Leu Asn Lys Lys Val Thr Lys Ala Val Leu Ser
1               5                   10                  15

Met Ile Val Gly Ile Ser Val Leu Ala Ser Pro Leu Ala Val Ala Ala
                20                  25                  30

Lys Thr Glu Asn Asn Lys Glu Gln Gln Val Ile Thr His Phe Asn Gln
                35                  40                  45

Arg Glu Asn Lys Phe Pro Asp Val Gly Gln Gly Ile Gln Trp Leu Ser
    50                  55                  60

Gln Phe Tyr Gly Lys Ser Leu Lys Asn Asn Gly Glu Gly Tyr Ser Leu
65                  70                  75                  80

Gly Gln Asp Val Met Arg Tyr Phe Leu Glu Val Lys Asn Ser Tyr Gly
                85                  90                  95

Gln Leu Ala Met Glu Pro Gln Val Ile Ser Thr Thr Pro Leu Trp Ala
                100                 105                 110

Gly Gln Ser Asp Leu Glu Asn Ala Thr Asp His Glu Gln Thr Leu Asn
                115                 120                 125

Ser Thr Glu Phe Lys Lys Thr Tyr Ser Asn Thr Thr Thr Ser Thr
                130                 135                 140

Glu Asn Gly Phe Met Ile Gly Gln Glu Thr Glu Gly Lys Val Gly Ile
145                 150                 155                 160

Pro Phe Val Ala Glu Gly Lys Val Thr Ile Lys Thr Glu Tyr Asn Phe
                165                 170                 175

Asn His Thr Asn Gly Tyr Glu Thr Ser Glu Ser Val Glu Tyr Ile Ala
                180                 185                 190

Pro Ser Gln Ser Ile Lys Val Pro Pro His Thr Ile Ala Arg Val Thr
                195                 200                 205

Ala Leu Leu Asp Val Lys Lys Ile Lys Gly Lys Met His Leu Tyr Ser
210                 215                 220

Glu Ile Gly Leu Asn Lys Asp Tyr Gly Tyr Asp Met Val Pro Leu Val
225                 230                 235                 240

Tyr Lys Tyr Gly Gly Pro Phe Lys Tyr Val Thr Leu Gly Thr Leu Tyr
                245                 250                 255

Asp Glu Gly Tyr Lys Gln Ala Gln Leu Asp Tyr Phe Asn Met Gly Asn
                260                 265                 270

Val Ile Pro Glu Glu Ile Glu Thr Val Ser Lys Ser Asn Asn Pro Asn
                275                 280                 285

His Leu Leu Ala Ser Gly Val Gly Ile Phe Glu Ser Glu Tyr Gly Ser
                290                 295                 300

Val Phe Asn Val Lys Val Glu Tyr Ile Asn Ile Asn Thr Lys Lys Ile
305                 310                 315                 320

Glu Lys Thr Glu Asn Leu Thr Ile Glu Pro Thr Ile Val Pro Val Lys
                325                 330                 335

Gln Thr Asn Thr Lys
                340

<210> SEQ ID NO 33
<211> LENGTH: 325
<212> TYPE: PRT
<213> ORGANISM: Bacillus thuringiensis
<220> FEATURE:
<223> OTHER INFORMATION: axmi-486 (alternate start site) (Ref:
      WO/2015/088937)

<400> SEQUENCE: 33

Met Ile Val Gly Ile Ser Val Leu Ala Ser Pro Leu Ala Val Ala Ala
1               5                   10                  15
```

Lys Thr Glu Asn Asn Lys Glu Gln Gln Val Ile Thr His Phe Asn Gln
                20                  25                  30

Arg Glu Asn Lys Phe Pro Asp Val Gly Gln Gly Ile Gln Trp Leu Ser
            35                  40                  45

Gln Phe Tyr Gly Lys Ser Leu Lys Asn Asn Gly Glu Gly Tyr Ser Leu
 50                  55                  60

Gly Gln Asp Val Met Arg Tyr Phe Leu Glu Val Lys Asn Ser Tyr Gly
 65                  70                  75                  80

Gln Leu Ala Met Glu Pro Gln Val Ile Ser Thr Thr Pro Leu Trp Ala
                85                  90                  95

Gly Gln Ser Asp Leu Glu Asn Ala Thr Asp His Glu Gly Thr Leu Asn
            100                 105                 110

Ser Thr Glu Phe Lys Lys Thr Tyr Ser Asn Thr Thr Thr Ser Thr
            115                 120                 125

Glu Asn Gly Phe Met Ile Gly Gln Glu Thr Glu Gly Lys Val Gly Ile
130                 135                 140

Pro Phe Val Ala Glu Gly Lys Val Thr Ile Lys Thr Glu Tyr Asn Phe
145                 150                 155                 160

Asn His Thr Asn Gly Tyr Glu Thr Ser Glu Ser Val Glu Tyr Ile Ala
                165                 170                 175

Pro Ser Gln Ser Ile Lys Val Pro Pro His Thr Ile Ala Arg Val Thr
            180                 185                 190

Ala Leu Leu Asp Val Lys Lys Ile Lys Gly Lys Met His Leu Tyr Ser
            195                 200                 205

Glu Ile Gly Leu Asn Lys Asp Tyr Gly Tyr Asp Met Val Pro Leu Val
210                 215                 220

Tyr Lys Tyr Gly Gly Pro Phe Lys Tyr Val Thr Leu Gly Thr Leu Tyr
225                 230                 235                 240

Asp Glu Gly Tyr Lys Gln Ala Gln Leu Asp Tyr Phe Asn Met Gly Asn
                245                 250                 255

Val Ile Pro Glu Glu Ile Glu Thr Val Ser Lys Ser Asn Asn Pro Asn
            260                 265                 270

His Leu Leu Ala Ser Gly Val Gly Ile Phe Glu Ser Gly Tyr Gly Ser
            275                 280                 285

Val Phe Asn Val Lys Val Glu Tyr Ile Asn Ile Asn Thr Lys Lys Ile
290                 295                 300

Glu Lys Thr Glu Asn Leu Thr Ile Glu Pro Thr Ile Val Pro Val Lys
305                 310                 315                 320

Gln Thr Asn Thr Lys
            325

<210> SEQ ID NO 34
<211> LENGTH: 315
<212> TYPE: PRT
<213> ORGANISM: Bacillus thuringiensis
<220> FEATURE:
<223> OTHER INFORMATION: axmi-486 (alternate start site) (Ref:
      WO/2015/088937)

<400> SEQUENCE: 34

Met Leu Ala Val Ala Ala Lys Thr Glu Asn Asn Lys Glu Gln Gln Val
1               5                   10                  15

Ile Thr His Phe Asn Gln Arg Glu Asn Lys Phe Pro Asp Val Gly Gln
                20                  25                  30

Gly Ile Gln Trp Leu Ser Gln Phe Tyr Gly Lys Ser Leu Lys Asn Asn

```
                 35                  40                  45
Gly Glu Gly Tyr Ser Leu Gly Gln Asp Val Met Arg Tyr Phe Leu Glu
 50                  55                  60

Val Lys Asn Ser Tyr Gly Gln Leu Ala Met Glu Pro Gln Val Ile Ser
 65                  70                  75                  80

Thr Thr Pro Leu Trp Ala Gly Gln Ser Asp Leu Glu Asn Ala Thr Asp
                 85                  90                  95

His Glu Gln Thr Leu Asn Ser Thr Glu Phe Lys Lys Thr Tyr Ser Asn
                 100                 105                 110

Thr Thr Thr Thr Ser Thr Glu Asn Gly Phe Met Ile Gly Gln Glu Thr
                 115                 120                 125

Glu Gly Lys Val Gly Ile Pro Phe Val Ala Glu Gly Lys Val Thr Ile
 130                 135                 140

Lys Thr Glu Tyr Asn Phe Asn His Thr Asn Gly Tyr Glu Thr Ser Glu
 145                 150                 155                 160

Ser Val Glu Tyr Ile Ala Pro Ser Gln Ser Ile Lys Val Pro Pro His
                 165                 170                 175

Thr Ile Ala Arg Val Thr Ala Leu Leu Asp Val Lys Lys Ile Lys Gly
                 180                 185                 190

Lys Met His Leu Tyr Ser Glu Ile Gly Leu Asn Lys Asp Tyr Gly Tyr
                 195                 200                 205

Asp Met Val Pro Leu Val Tyr Lys Tyr Gly Pro Phe Lys Tyr Val
 210                 215                 220

Thr Leu Gly Thr Leu Tyr Asp Glu Gly Tyr Lys Gln Ala Gln Leu Asp
 225                 230                 235                 240

Tyr Phe Asn Met Gly Asn Val Ile Pro Glu Glu Ile Glu Thr Val Ser
                 245                 250                 255

Lys Ser Asn Asn Pro Asn His Leu Leu Ala Ser Gly Val Gly Ile Phe
                 260                 265                 270

Glu Ser Glu Tyr Gly Ser Val Phe Asn Val Lys Val Gly Tyr Ile Asn
                 275                 280                 285

Ile Asn Thr Lys Lys Ile Glu Lys Thr Glu Asn Leu Thr Ile Glu Pro
 290                 295                 300

Thr Ile Val Pro Val Lys Gln Thr Asn Thr Lys
 305                 310                 315
```

<210> SEQ ID NO 35
<211> LENGTH: 257
<212> TYPE: PRT
<213> ORGANISM: Bacillus thuringiensis
<220> FEATURE:
<223> OTHER INFORMATION: axmi-486 (alternate start site) (Ref: WO/2015/088937)

<400> SEQUENCE: 35

```
Met Arg Tyr Phe Leu Glu Val Lys Asn Ser Tyr Gly Gln Leu Ala Met
 1               5                  10                  15

Glu Pro Gln Val Ile Ser Thr Thr Pro Leu Trp Ala Gly Gln Ser Asp
                 20                  25                  30

Leu Glu Asn Ala Thr Asp His Glu Gln Thr Leu Asn Ser Thr Glu Phe
                 35                  40                  45

Lys Lys Thr Tyr Ser Asn Thr Thr Thr Thr Ser Thr Glu Asn Gly Phe
 50                  55                  60

Met Ile Gly Gln Glu Thr Glu Gly Lys Val Gly Ile Pro Phe Val Ala
 65                  70                  75                  80
```

```
Glu Gly Lys Val Thr Ile Lys Thr Glu Tyr Asn Phe Asn His Thr Asn
                85                  90                  95
Gly Tyr Glu Thr Ser Glu Ser Val Glu Tyr Ile Ala Pro Ser Gln Ser
            100                 105                 110
Ile Lys Val Pro Pro His Thr Ile Ala Arg Val Thr Ala Leu Leu Asp
        115                 120                 125
Val Lys Lys Ile Lys Gly Lys Met His Leu Tyr Ser Glu Ile Gly Leu
130                 135                 140
Asn Lys Asp Tyr Gly Tyr Asp Met Val Pro Leu Val Tyr Lys Tyr Gly
145                 150                 155                 160
Gly Pro Phe Lys Tyr Val Thr Leu Gly Thr Leu Tyr Asp Glu Gly Tyr
                165                 170                 175
Lys Gln Ala Gln Leu Asp Tyr Phe Asn Met Gly Asn Val Ile Pro Glu
            180                 185                 190
Glu Ile Glu Thr Val Ser Lys Ser Asn Asn Pro Asn His Leu Leu Ala
        195                 200                 205
Ser Gly Val Gly Ile Phe Glu Ser Glu Tyr Gly Ser Val Phe Asn Val
210                 215                 220
Lys Val Glu Tyr Ile Asn Ile Asn Thr Lys Lys Ile Glu Lys Thr Glu
225                 230                 235                 240
Asn Leu Thr Ile Glu Pro Thr Ile Val Pro Val Lys Gln Thr Asn Thr
                245                 250                 255
Lys

<210> SEQ ID NO 36
<211> LENGTH: 242
<212> TYPE: PRT
<213> ORGANISM: Bacillus thuringiensis
<220> FEATURE:
<223> OTHER INFORMATION: axmi-486 (alternate start site) (Ref:
      WO/2015/088937)

<400> SEQUENCE: 36

Met Glu Pro Gln Val Ile Ser Thr Thr Pro Leu Trp Ala Gly Gln Ser
1               5                   10                  15
Asp Leu Glu Asn Ala Thr Asp His Glu Gln Thr Leu Asn Ser Thr Glu
            20                  25                  30
Phe Lys Lys Thr Tyr Ser Asn Thr Thr Thr Ser Thr Glu Asn Gly
        35                  40                  45
Phe Met Ile Gly Gln Glu Thr Glu Gly Lys Val Gly Ile Pro Phe Val
    50                  55                  60
Ala Glu Gly Lys Val Thr Ile Lys Thr Glu Tyr Asn Phe Asn His Thr
65                  70                  75                  80
Asn Gly Tyr Glu Thr Ser Glu Ser Val Glu Tyr Ile Ala Pro Ser Gln
                85                  90                  95
Ser Ile Lys Val Pro Pro His Thr Ile Ala Arg Val Thr Ala Leu Leu
            100                 105                 110
Asp Val Lys Lys Ile Lys Gly Lys Met His Leu Tyr Ser Glu Ile Gly
        115                 120                 125
Leu Asn Lys Asp Tyr Gly Tyr Asp Met Val Pro Leu Val Tyr Lys Tyr
    130                 135                 140
Gly Gly Pro Phe Lys Tyr Val Thr Leu Gly Thr Leu Tyr Asp Glu Gly
145                 150                 155                 160
Tyr Lys Gln Ala Gln Leu Asp Tyr Phe Asn Met Gly Asn Val Ile Pro
                165                 170                 175
```

-continued

```
Glu Glu Ile Glu Thr Val Ser Lys Ser Asn Asn Pro Asn His Leu Leu
            180                 185                 190

Ala Ser Gly Val Gly Ile Phe Glu Ser Glu Tyr Gly Ser Val Phe Asn
        195                 200                 205

Val Lys Val Glu Tyr Ile Asn Ile Asn Thr Lys Lys Ile Glu Lys Thr
    210                 215                 220

Glu Asn Leu Thr Ile Glu Pro Thr Ile Val Pro Val Lys Gln Thr Asn
225                 230                 235                 240

Thr Lys
```